(12) United States Patent
Abidi et al.

(10) Patent No.: US 12,270,152 B2
(45) Date of Patent: Apr. 8, 2025

(54) DISSOLUTION OF CELLULOSE IN IONIC LIQUIDS

(71) Applicant: Texas Tech University System, Lubbock, TX (US)

(72) Inventors: Noureddine Abidi, Lubbock, TX (US); Edward Quitevis, Lubbock, TX (US); Vidura D. Thalangamaarachchige, Lubbock, TX (US); Niwanthi Dissanayake, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 1103 days.

(21) Appl. No.: 16/961,996

(22) PCT Filed: Jan. 17, 2019

(86) PCT No.: PCT/US2019/013990
§ 371 (c)(1),
(2) Date: Jul. 14, 2020

(87) PCT Pub. No.: WO2019/143802
PCT Pub. Date: Jul. 25, 2019

(65) Prior Publication Data
US 2021/0079593 A1  Mar. 18, 2021

Related U.S. Application Data

(60) Provisional application No. 62/618,274, filed on Jan. 17, 2018.

(51) Int. Cl.
*D21C 3/20* (2006.01)
*C07D 233/58* (2006.01)
*C08B 1/00* (2006.01)
*C08J 3/09* (2006.01)
*D21C 3/26* (2006.01)

(52) U.S. Cl.
CPC ............. *D21C 3/20* (2013.01); *C07D 233/58* (2013.01); *C08B 1/003* (2013.01); *C08J 3/095* (2013.01); *C08J 3/096* (2013.01); *D21C 3/26* (2013.01); *C08J 2301/02* (2013.01)

(58) Field of Classification Search
CPC ............. D21C 3/20; D21C 3/26; D21C 3/222
See application file for complete search history.

(56) References Cited

U.S. PATENT DOCUMENTS

2013/0056165 A1* 3/2013 Kilpelainen ........... D21C 9/007
162/100

FOREIGN PATENT DOCUMENTS

WO  WO-2007006418 A1 *  1/2007 ............... A61K 8/45
WO  WO-2012175584 A1 * 12/2012 ........... C07D 307/46

OTHER PUBLICATIONS

Lan et al., Rapid Dissolution of Cellulose in Ionic Liquid with Different Methods, 2013, Cellulose—Fundamental aspects, chapter 7. (Year: 2013).*

(Continued)

*Primary Examiner* — Anthony Calandra
(74) *Attorney, Agent, or Firm* — Edwin S. Flores; Daniel J. Chalker; Chalker Flores, LLP

(57) ABSTRACT

The present invention includes a method for dissolving cellulose comprising dissolving cellulose in an ionic liquid and a co-solvent, wherein the ionic liquid is an imidazolium-based ionic liquid with, e.g., a halide or acetate as the anion.

19 Claims, 34 Drawing Sheets

(56) References Cited

OTHER PUBLICATIONS

Abe M, et al. (2010) "Extraction of polysaccharides from bran with phosphonate or phosphinate-derived ionic liquids under short mixing time and low temperature" Green Chemistry 12:1274-1280 doi:10.1039/c003976d.

Abidi N et al. (2008) "Evaluating cell wall structure and composition of developing cotton fibers using Fourier transform infrared spectroscopy and thermogravimetric analysis" J Appl Polym Sci 107:476-486 doi:10.1002/app.27100.

Abidi N, et al. (2014) "Changes in the cell wall and cellulose content of developing cotton fibers investigated by FTIR spectroscopy" Carbohydrate Polymers 100:9-16 doi: 10.1016/j.carbpol.2013.01.074.

Bylin, S. et al. "Solvation of cellulose and xylan in the MIM/EMIMAc ionic liquid solvent system: Parameters for small-scale solvation", BioResources, 2014, 9(1), 1038-1054.

Dassanayake RS et al. (2016) "Preparation and adsorption properties of aerocellulose-derived activated carbon monoliths" Cellulose 23:1363-1374 doi:10. 1007/s10570-016-0886-1.

Fukaya, Y., et al. "Cellulose dissolution with polar ionic liquids under mild conditions: required factors for anions." Green Chemistry, 2008. 10(1): p. 44-46.

Gericke M et al. (2012) "Ionic Liquids—Promising but Challenging Solvents for Homogeneous Derivatization of Cellulose" Molecules 17:7458-7502 doi: 10.3390/molecules17067458.

Gupta KM et al. (2015) "Cellulose dissolution and regeneration in ionic liquids: A computational perspective" Chem Eng Sci 121:180-189 doi:10.1016/j.ces.2014.07.025.

Haigler CH et al. (2012) "Cotton fiber: a powerful single-cell model for cell wall and cellulose research" Front Plant Sci 3:7 doi: 10.3389/fpls.2012.00104.

Heinze T et al. (2008) "Interactions of ionic liquids with polysaccharides—2: Cellulose" Macromol Symp 262:8-22 doi:10.1002/masy.200850202.

Ilharco LM et al. (1997) "Infrared approach to the study of adsorption on cellulose: Influence of cellulose crystallinity on the adsorption of benzophenone" Langmuir 13:4126-4132 doi: 10.1021/la962138u.

International Search Report (ISA/AU) PCT/US2019/013990 dated Apr. 17, 2019.

Kosan B et al. (2008) "Dissolution and forming of cellulose with ionic liquids" Cellulose 15:59-66 doi:10.1007/s10570-007-9160-x.

Lan W et al. (2011) "Ultrasound-assisted dissolution of cellulose in ionic liquid" Carbohydrate Polymers 86:672-677 doi:10.1016/j.carbpol.2011.05.013.

Lau RM et al (2004) "Dissolution of Candida antarctica lipase B in ionic liquids: effects on structure and activity" Green Chemistry 6:483-487 doi: 10.1039/b405693k.

Li Y et al. (2015) "Dissolving process of a cellulose bunch in ionic liquids: a molecular dynamics study" Phys Chem Phys 17:17894-17905 doi: 10.1039/c5cp02009c.

Lindman B et al. (2010) "On the mechanism of dissolution of cellulose" J Mol Liq 156:76-81 doi:10.1016/j.molliq.2010.04.016.

Lu BL et al. (2014) "Cation does matter: how cationic structure affects the dissolution of cellulose in ionic liquids" Green Chemistry 16:1326-1335 doi: 10.1039/c3gc41733f.

Mai, N. L. et al. "Efficient pretreatment of lignocellulose in ionic liquids/co-solvent for enzymatic hydrolysis into fermentable sugars" Process Biochemistry, 2014, 49, 1144-1151.

Oh SY et al. (2005a) "Crystalline structure analysis of cellulose treated with sodium hydroxide and carbon dioxide by means of X-ray diffraction and FTIR spectroscopy" Carbohydr Res 340:2376-2391 doi: 10.1016/j.carres.2005.08.007.

Oh SY et al. (2005b) "FTIR analysis of cellulose treated with sodium hydroxide and carbon dioxide" Carbohydr Res 340:417-428 doi:http://dx.doi.org/10.1016/j.carres.2004.11.027.

Olsson C, et al. (2013) "Direct Dissolution of Cellulose: Background, Means and Applications" Cellulose—Fundamental Aspects: 143-178 doi: 10.5772/52144.

"Phillips DM et al. (2004) "Dissolution and regeneration of Bombyx mori Silk fibroinusing ionic liquids" J Am Chem Soc 126:14350-14351 doi: 10.1021/ja046079f".

Pinkert A et al. (2009) "Ionic Liquids and Their Interaction with Cellulose" Chem Rev 109:6712-6728 doi:10.1021/cr9001947.

Rabideau BD et al. (2014) "The Role of the Cation in the Solvation of Cellulose by Imidazolium-Based Ionic Liquids" J Phys Chem B 118:1621-1629 doi:10.1021/jp4115755.

"Ragauskas AJ et al. (2006) "The path forward for biofuels and biomaterials"" Science311:484-489 doi:10.1126/science.1114736.

Remsing RC et al. (2006) "Mechanism of cellulose dissolution in the ionic liquid 1-n-butyl-3-methylimidazolium chloride: a C-13 and Cl-35/37 NMR relaxation study on model systems" Chem Commun: 1271-1273 doi: 10.1039/b600586c.

Remsing RC et al. (2008) "Solvation of carbohydrates in N,N'-dialkylimidazolium ionic liquids: A multinuclear NMR spectroscopy study" J Phys Chem B 112:11071-11078 doi:10.1021/jp8042895.

Rogers R et al. (2003) "Ionic liquids—Solvents of the future?" Science 302:792-793 doi: 10.1126/science.1090313.

Salmen L et al. (2009) "Cellulose structural arrangement in relation to spectralchanges in tensile loading" FTIR Cellulose 16:975-982 doi:10.1007/s10570-009-9331-z.

Samir M et al. (2005) "Review of recent research into cellulosic whiskers, their properties and their application in hanocomposite field" Biomacromolecules 6:612-626 doi:10.1021/bm0493685.

Schwanninger M et al. (2004) "Effects of short-time vibratory ball milling on the shape of FT-IR spectra of wood and cellulose" Vibrational Spectroscopy 36:23-40 doi:http://dx.doi.org/10.1016/j.vibspec.2004.02.003.

Sun N et al. (2011) "Where are ionic liquid strategies most suited in the pursuit of chemicals and energy from ignocellulosic biomass?" Chem Commun 47:1405-1421 doi:10.1039/c0cc03990j.

Swatloski RP et al. (2002) "Dissolution of cellose with ionic liquids" J Am Chem Soc 124:4974-4975 doi:10.1021/ia025790m.

Tywabi, Z. et al. "Study of cellulose-rich materials recovered after dissolution of sulphite pulp from South African Eucalyptus Wood in [C2mim][OAc]/co-solvent mixtures", Journal of Scientific & Industrial Research, 2017, 76, 540-544.

Vitz J et al. (2009) "Extended dissolution studies of cellulose in imidazolium based ionic liquids" Green Chemistry 11:417-424 doi:10.1039/b818061j.

Welton T (1999) "Room-temperature ionic liquids. Solvents for synthesis and catalysis" Chem Rev 99:2071-2083 doi:10.1021/cr980032t.

Xu AR et al. (2010) "Effects of anionic structure and lithium salts addition on the dissolution of cellulose in 1-butyl-3-methylimidazolium-based ionic liquid solvent systems" Green Chemistry 12:268-275 doi: 10.1039/b916882f.

Xu H et al. (2012) "Understanding the mechanism of cellulose dissolution in 1-butyl-3-methylimidazolium chloride ionic liquid via quantum chemistry calculations and molecular dynamics simulations" J Comput-Aided Mol Des 26:329-337 doi:10.1007/s10822-012-9559-9.

Xu, A et al. "Disslution behaviour of cellulose in IL + DMSO solvent: Effect of alkyl length in imidazolium cation on cellulose dissolution", Advances in Materials Science and Engineering, 2015, vol. 2015, Article ID 406470, 4 pages; url: http://dx.doi.org/10.1155/2015/406470.

Xu, A et al. "Cellulose dissolution at ambient temperature: Role of preferential solvation cations of ionic liquids by a cosolvent", Carbohydrate Polymers, 2013, 92, 540-544.

Yao YY et al. (2015) "Mechanistic study on the cellulose dissolution in ionic liquids by density functional theory" Chin J Chem Eng 23:1894-1906 doi:10.1016/j.cjche.2015.07.018.

Youngs TGA et al. (2007) "Glucose solvation by the ionic liquid 1,3-dimethylimidazolium chloride: A simulation study" J Phys Chem B 111:13765-13774 doi:10.1021/Jp076728k.

(56) References Cited

OTHER PUBLICATIONS

"Youngs TGA et al. (2011) "Neutron diffraction, NMR and molecular dynamics study of glucose dissolved in the ionic liquid 1-ethyl-3-methylimidazolium acetate" Chem Sci 2:1594-1605 doi:10.1039/c1sc00241d".

Zhang H et al. (2005) "1-Allyl-3-methylimidazolium chloride room temperature ionic liquid: A new and powerful nonderivatizing solvent for cellulose" Macromolecules 38:8272-8277 doi:10.1021/ma0505676.

Zhang SJ et al. (2006) "Physical properties of ionic liquids: Database and evaluation" J Phys Chem Ref Data 35:1475-1517 doi:10.1063/1.2204959.

* cited by examiner

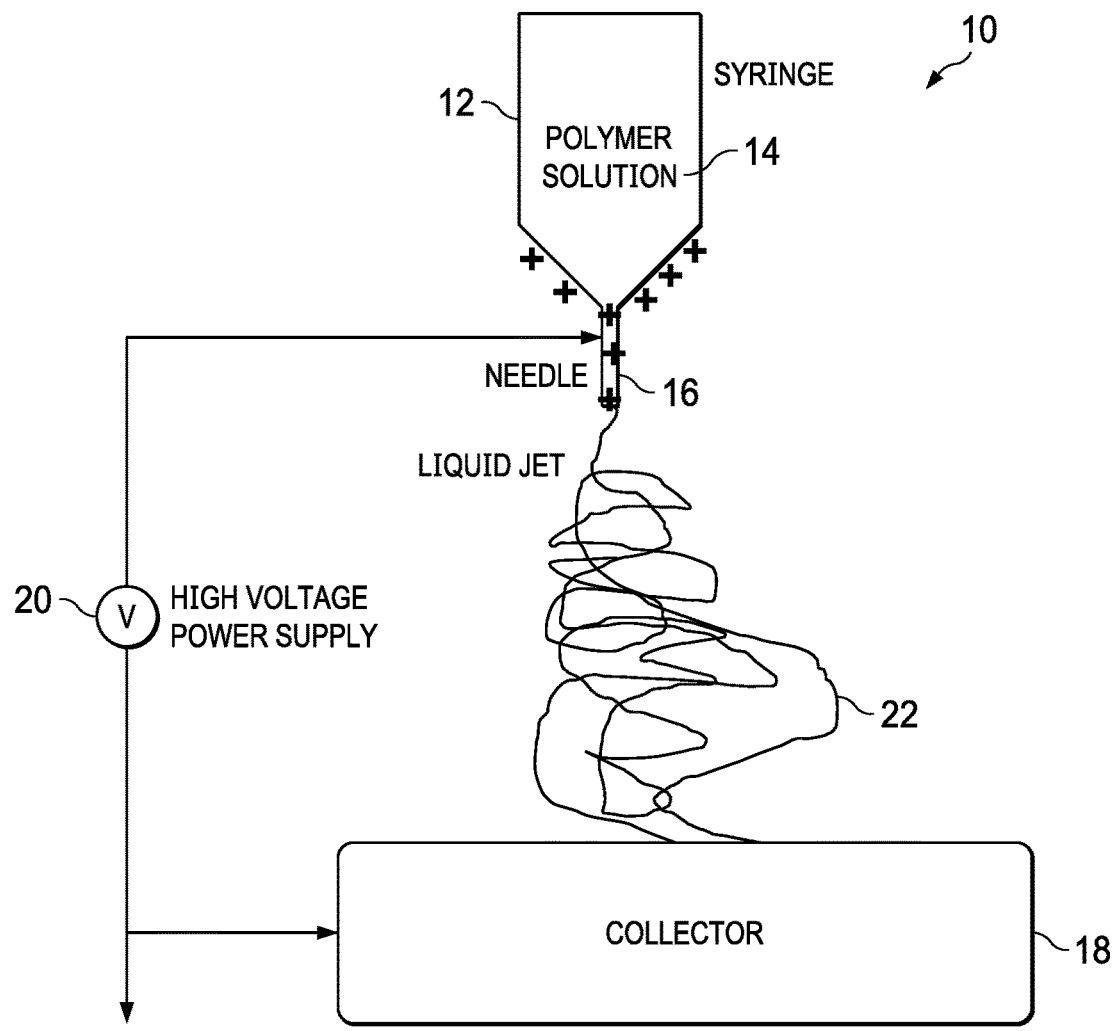
FIG. 35
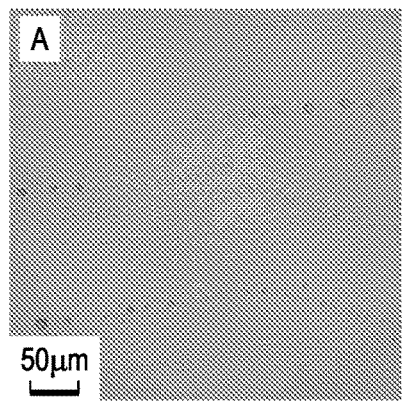 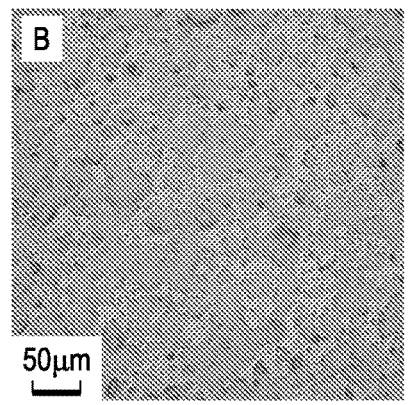
FIG. 36A  FIG. 36B

DISSOLUTION OF CELLULOSE IN IONIC LIQUIDS

CROSS-REFERENCE TO RELATED APPLICATIONS

This application is the National Stage of International Application No. PCT/US2019/013990, filed on Jan. 17, 2019 claiming the priority of U.S. Provisional Application No. 62/618,274, filed on Jan. 17, 2018, the content of each of which is incorporated by reference herein.

TECHNICAL FIELD OF THE INVENTION

The present invention relates in general to the field of cellulose dissolution using novel agents.

BACKGROUND OF THE INVENTION

Without limiting the scope of the invention, its background is described in connection with dissolving various types of cellulose.

Cellulose is the most abundant, natural, renewable and biodegradable polymer on earth. Cellulose can be obtained from various sources such as rice, wheat, sugar cane, and other agricultural products, as well as from bacteria. Cellulose can be a useful material when dissolved and reformed into another physical form. However, cellulose is difficult to dissolve due to its high degree of polymerization, extensive hydrogen bonding, and high crystallinity. For this reason, most studies published to date have described dissolution of cellulose with a low degree of polymerization (DP), which is easier to achieve than dissolution of high DP cellulose. Generally speaking, when the DP is <700, cellulose is considered low DP, while when the DP is >700 cellulose is considered high DP.

Cotton is the most cellulose-rich plant species. Mature cotton fiber contains >90% (w/w) crystalline cellulose, including its cellulosic secondary wall, which is surrounded by the cuticulated primary wall (Hailger 2012) and is therefore a high DP cellulose. Cellulose in the cotton fiber has numerous applications. However, many of these applications require the cotton to be dissolved first (Gericke et al. 2012; Ragauskas et al. 2006). The crystalline structure and the strong hydrogen-bond network make it thermally and chemically stable. As a result, cotton (or any high DP) cellulose is particularly difficult to dissolve in water or common organic solvents.

Most of the available information on cellulose dissolution is based on work with low DP cellulose, which is generally easier to dissolve than high DP cellulose, such as cotton cellulose. In recent years, ionic liquids (ILs) have been proposed as solvents for biopolymers (Lau et al. 2004; Phillips et al. 2004). Compared to conventional organic solvents, ILs have unique features such as negligible vapor pressure, non-flammability, high chemical and thermal stability, and the ability to dissolve many organic and inorganic materials (Pinkert et al. 2009; Rogers and Seddon 2003; Sun et al. 2011; Welton 1999). Rogers and coworkers first showed that imidazolium-based ILs with strong hydrogen-bonding anions are able to dissolve low DP cellulose upon heating (Rogers and Seddon 2003). In case of the IL, 1-butyl-3-methylimidazolium chloride ([$C_4C_1$im][Cl]), the rate of low DP cellulose dissolution was greatly improved when heated in a microwave oven with pulsing at full power (Swatloski et al. 2002). Recent studies also found that some ILs can dissolve low DP cellulose at lower temperatures and that the ILs can be easily recovered by a recycling process (Abe et al. 2010; Kosan et al. 2008; Lan et al. 2011; Vitz et al. 2009; Xu et al. 2010; Zhang et al. 2005). One of the advantages of using ILs to dissolve cellulose is the ability to tune the chemical and physical properties of ILs by varying the structures of the cations and anions (Zhang et al. 2006). However, it is not currently understood exactly how the cation affects cellulose dissolution or how the cations and anions interact with each other in a given IL during cellulose dissolution, nor is it understood how ILs would work in dissolution with high DP cellulose, which is more difficult to dissolve than low DP cellulose.

It is generally accepted that the interaction of anions of ILs with the hydroxyl groups of cellulose to form hydrogen bonds plays a key role in the dissolution of cellulose. However, the mechanism of cellulose dissolution is still not well understood (Yao et al. 2015). In particular, despite the various studies to date on the dissolution of low DP cellulose by ILs, there are conflicting explanations for the role of the cation in the dissolution of low DP cellulose (Lu et al. 2014; Xu et al. 2012). For example, the mechanism of carbohydrate dissolution in acetate and chloride anion containing ILs was examined by utilizing $^{13}$C and $^{35/37}$Cl relaxation rates of the corresponding anions (Remsing et al. 2008; Remsing et al. 2006). These studies indicate that the relaxation time depends strongly on the cellulose content, but only slight variations of relaxation time were observed when the cation was varied. This result suggests that the cation plays a minor role in cellulose dissolution. Youngs et al. utilized $^1$H NMR and molecular dynamics (MD) simulations to study the interactions between glucose and ILs such as 1-ethyl-3-methylimidazolium acetate and 1,3-dimethylimidazolium chloride (Youngs et al. 2007; Youngs et al. 2011). They found that the major interaction was between the anion of the IL and the hydrogens of the hydroxyl groups on the glucose units, whereas there were only minor interactions between the cation and the sugar. In contrast, a study of the interaction of 1-butyl-3-methylimidazolium acetate ([$C_4C_1$im][OAc]) with cellobiose by Zhang et al. revealed that both the cation and anion were required in the dissolution process (Zhang et al. 2005). A study by Lindman et al. reported that the hydrophobic interactions between cations of ILs and cellulose were the main driving forces in dissolution (Lindman et al. 2010). Another study by Olsson and Westman confirmed that the anion of the IL penetrates the cellulose and dissembles the cellulose structure by competitive hydrogen bonding (Olsson and Westman 2013). Lu et al. proposed that the cation plays a more prominent role than had been previously thought. They hypothesized that the cation and anion should be sufficiently small enough to reach hydroxyl groups of cellulose (Lu et al. 2014). They further proposed electron donor-acceptors also play a role in cellulose dissolution by breaking up cellulose-cellulose hydrogen bonding interactions. The computational studies performed by Gupta and Jiang indicated that the dissolution of cellulose in ILs is initiated by the disruption of hydrogen bonds in cellulose (Gupta and Jiang 2015). This was mainly through the formation of hydrogen bonds between the anions and cellulose and the hydrophobic interactions with cations.

Although experiments to date show that the anions play an important role in the dissolution of cellulose in ionic liquids, there is still not a clear understanding of the role of the cation and the mechanism of dissolution. Two recent MD simulations by Rabideau et al. and Li et al. have provided molecular-level insights into the interactions of ionic species in ILs with cellulose and the possible mechanism for cellulose dissolution in ILs (Li et al. 2015; Rabideau et al. 2014).

Rabideau et al. performed a systematic MD simulation study of the dissolution of cellulose in three ILs: $[C_2C_1im][OAc]$, $[C_4C_1im][Cl]$, and $[C_2C_2im][DMP]$, where $[DMP]^-$ is the dimethyl phosphate anion. In their study, the breakup of small bundles of cellulose $I_\alpha$ and $I_\beta$ in the ILs $[C_4C_1im][Cl]$, $[C_2C_1im][OAc]$, and $[C_1C_1im][DMP]$ were investigated. According to their results, anions first bind strongly to the hydroxyl groups of the exterior strands of the bundle, forming negatively charged complexes. The binding of anions to hydroxyl groups deteriorates the intrastrand hydrogen bonds present in the cellulose strands, reducing the rigidity of the strands. Then, due to charge imbalances, cations intercalate between strands. This provides the bulk to push the individual moieties apart and initiates the separation. Rabideau et al. observed the peeling of an individual strand from the main bundle in $[C_2C_1im][OAc]$. This led to disruption of the hydrogen bonds with other strands, resulting in chain detachment of individual glucan units from the main bundle.

Li et al. performed long (3 ms) MD simulations on a cellulose bundle comprised of 4 strands, each with 8 glucose units, and a cellulose bundle comprised of 7 strands, each with 8 glucose units, in $[C_2C_1im][OAc]$, $[C_2C_1im][Cl]$ and $[C_4C_1im][Cl]$. The behavior of the cellulose bundles in these ILs is similar to that observed by Rabideau et al. in their MD simulations. Li et al. observed complete breakup of the 7-strand bundle in 500 ns for $[C_2C_1im][OAc]$, but observed little change for $[C_2C_1im][Cl]$ and $[C_4C_1im][Cl]$ in the same time period. They observed that for $[C_2C_1im][OAc]$, the $[OAc]^-$ ions bind tightly to the hydroxyl groups, thus weakening the binding between the neighboring cellulose sheets due to $[OAc]^-$ being larger size than $[Cl]^-$. This allows more ions to enter into the cellulose gap. However, in contrast to MD simulations of Rabideau et al., those of Li et al. showed the cations having a strong van der Waals interaction with cellulose. These contradictory results have created a significant discrepancy in the field of cellulose processing, making it difficult to predict which ILs and conditions would be most effective for cellulose dissolution. As explained above, most of the current work was performed with low DP cellulose. High DP cellulose has properties that make it particularly difficult to dissolve, thus compounding the problem of understanding what methods of dissolution might be effective in dissolving high DP cellulose to form useful substances.

Taking into account all of the above, a need remains for compositions and methods for the dissolution of cellulose, including high DP cellulose, that is more efficient and effective, uses less harmful materials, and can be conducted under ambient conditions.

SUMMARY OF THE INVENTION

In one embodiment, the present invention includes a method for dissolving cellulose comprising: dissolving the cellulose in an ionic liquid and a co-solvent, wherein the ionic liquid is selected from an imidazolium-based ionic liquid with acetate as the anion. In one aspect, the ionic liquid is selected from 1-butyl-3-methylimidazolium methylphosphonate $[C_4C_1im][(MeO)(H)PO_2]$ or an acetate-based anion. In another aspect, the co-solvent is selected from at least one of 1-methylimidazole, 1-ethylimidazole, or 1-butylimidazole. In another aspect, the imidazolium-based ionic liquid is a 1-alkylimidazolium. In another aspect, the 1-alkylimidazolium is selected from 1-methylimidazolium, 1-ethylimidazolium, 1-propylimidazolium, 1-butylimidazolium, 1-heptyl-3-methylimidazolium, 1-(cyclohexylmethyl)-3-methylimidazolium, 1-benzyl-3-methylimidazolium, 1,3-dibenzylimidazolium, 1-(2-napthylmethyl)-3-methylimidazolium, or 1,3-dibenzylimidazolium. In another aspect, the dissolving step is 15 minutes or less. In another aspect, the dissolution of cellulose is achieved after microwaving the cellulose in the ionic liquid and the co-solvent. In another aspect, the method further comprises the step of pretreating the cellulose with alcohol prior to the dissolving step. In another aspect, the method further comprises the step of drying the cellulose to remove alcohol for between 2 h to 8 h at temperatures between room temperature and 105° C. In another aspect, the alcohol is ethanol, 1-propoapanol, iso-propanol, or tert-butanol. In another aspect, the cellulose has a high degree of polymerization. In another aspect, the cellulose is a cotton, rice, wheat, sugar cane, hemp, tree, algal or bacterial cellulose. In another aspect, the cellulose with a high degree of polymerization is cotton cellulose. In another aspect, the step of pretreating is for 1, 2, 3, 4, 5, 6, 7, or 8 hours at a temperature between 15 to 30° C. In another aspect, the step of dissolving is at 90-100° C. In another aspect, the step of dissolving is in the presence of microwave energy. In another aspect, the method further comprises the step of drying the cellulose between the pretreating and the dissolving steps. In another aspect, the imidazolium-based ionic liquid with acetate as the anion is selected from at least one of 1-hepyl-3-methylimidazolium acetate $([C_7C_1im][OAc])$, 1-(cyclohexylmethyl)-3-methylimidazolium acetate $([CyhmC_1im][OAc])$, 1-benzyl-3-methylimidazolium acetate $([BnzC_1im][OAc])$, 1,3-dibenzylimidazolium acetate $([(Bnz)_2im][OAc])$, and 1-(2-napthylmethyl)-3-methylimidazolium acetate $([NapmC_1im][OAc])$. In another aspect, the imidazolium-based ionic liquid is halogen substituted 1-hepyl-3-methylimidazolium halide (X) $([C_7C_1im]X)$, 1-(cyclohexylmethyl)-3-methylimidazolium halide $([CyhmC_1im]X)$, 1-benzyl-3-methylimidazolium halide $([BnzC_1im])$, 1,3-dibenzylimidazolium halide $([(Bnz)_2im]X)$, and 1-(2-napthylmethyl)-3-methylimidazolium halide $([NapmC_1im]X)$, 1-methylimidazolium halide, 1-ethylimidazolium halide, 1-propylimidazolium halide, or 1-butylimidazolium halide. In another aspect, prior to dissolving the cellulose is at least one of raw, scoured, bleached, air-dried, heat-dried, or ground. In another aspect, the method further comprises the step of regenerating the dissolved cellulose fibers by drawing, spinning, electrospinning, settling, layering, or matting. In another aspect, the imidazolium-based ionic liquid with acetate as the anion is pre-heated until fluid. In another aspect, the imidazolium-based ionic liquid with acetate as the anion is pre-heated to 70, 75, 80, 85, 90, 95, 96, 97, 97, 99, or 100° C. In another aspect, the co-solvent is selected from at least one of DMSO, DMF, DMI, DMAc, or N-methylimidazole (MIM).

In another embodiment, the present invention includes a method for dissolving cellulose comprising: pretreating cellulose in alcohol; and dissolving the alcohol pre-treated cellulose in an ionic liquid and a co-solvent, wherein the ionic liquid is an imidazolium-based ionic liquid with an anion. In one aspect, the ionic liquid is selected from 1-butyl-3-methylimidazolium methylphosphonate $[C_4C_1im][(MeO)(H)PO_2]$ or an acetate-based anion. In another aspect, the solvent is selected from at least one of 1-methylimidazole, 1-ethylimidazole, or 1-butylimidazole. In another aspect, the alcohol is selected from at least one of ethanol, 1-propoanol, iso-propanol, or tert-butanol. In another aspect, the dissolving step is 15 minutes or less. In another aspect, the combined alcohol pretreatment and co-solvent reduces the dissolution time when exposed to microwaves to between 1 and 15 seconds, 10 and 30 seconds, 15 and 60 seconds, 1 to 3 minutes, 3 to 5 minutes, 5 to 10 minutes, 10 to 15 minutes, 1 to 10 minutes, or less than 1, 2, 3, 4, 5, 6, 7, 8, 9, 10, 11, 12, 13, 14, or 15 minutes. In another aspect, the cellulose is a cotton, rice, wheat, sugar cane, hemp, tree, algal or bacterial cellulose. In another aspect, the cellulose has a high degree of polymerization. In another aspect, the cellulose is cotton cellulose. In another aspect, the step of pretreating is for 1, 2, 3, 4, 5, 6, 7, or 8 hours at a temperature between 15 to 30° C. In another aspect, the step of dissolving is at 90-100° C. In another aspect, the step of dissolving is in the presence of microwave energy. In another aspect, the method further comprises the step of drying the cellulose between the pretreating and the dissolving steps. In another aspect, the imidazolium-based ionic liquid with acetate as the anion is selected from at least one of 1-hepyl-3-methylimidazolium acetate ($[C_7C_1im][OAc]$), 1-(cyclohexylmethyl)-3-methylimidazolium acetate ($[CyhmC_1im][OAc]$), 1-benzyl-3-methylimidazolium acetate ($[BnzC_1im][OAc]$), 1,3-dibenzylimidazolium acetate ($[(Bnz)_2im][OAc]$), and 1-(2-napthylmethyl)-3-methylimidazolium acetate ($[NapmC_1im][OAc]$). In another aspect, the imidazolium-based ionic liquid is halogen substituted 1-hepyl-3-methylimidazolium halide (X) ($[C_7C_1im]X$), 1-(cyclohexylmethyl)-3-methylimidazolium halide ($[CyhmC_1im]X$), 1-benzyl-3-methylimidazolium halide ($[BnzC_1im]$), 1,3-dibenzylimidazolium halide ($[(Bnz)_2im]X$), and 1-(2-napthylmethyl)-3-methylimidazolium halide ($[NapmC_1im]X$), 1-methylimidazolium halide, 1-ethylimidazolium halide, 1-propylimidazolium halide, or 1-butylimidazolium halide. In another aspect, the method further comprises the step of regenerating the dissolved cellulose fibers by drawing, spinning, electrospinning, settling, layering, or matting. In another aspect, prior to pre-treatment the cellulose is at least one of raw, scoured, bleached, air-dried, heat-dried, or ground. In another aspect, the imidazolium-based ionic liquid with acetate as the anion is pre-heated until fluid. In another aspect, the imidazolium-based ionic liquid with acetate as the anion is pre-heated to 70, 75, 80, 85, 90, 95, 96, 97, 97, 99, or 100° C. In another aspect, the co-solvent is selected from at least one of DMSO, DMF, DMI, DMAc, or N-methylimidazole (MIM).

In another embodiment, the present invention includes a method of evaluating a compound believed to be useful in dissolving cellulose, the method comprising: (a) obtaining a compound comprising an ionic liquid comprising an imidazolium ring cation and an anion; (b) mixing the compound and cellulose in a solvent under conditions in which the cellulose dissolves; and (c) determining if the compound dissolves the cellulose at a rate or in a manner that is statistically significant as compared to any reduction occurring in solvent alone, wherein a statistically significant increase indicates that the compound is useful in dissolving cellulose.

In another embodiment, the present invention includes a dissolved cellulose material made by a method comprising: pretreating cellulose in alcohol; and dissolving the pretreated cellulose in an ionic liquid and a co-solvent, wherein the ionic liquid is an imidazolium-based ionic liquid. In one aspect, the ionic liquid is selected from 1-butyl-3-methylimidazolium methylphosphonate $[C_4mim][(MeO)(H)PO_2]$ or an acetate-based anion. In another aspect, the solvent is selected from at least one of 1-methylimidazole, 1-ethylimidazole, or 1-butylimidazole. In another aspect, the dissolving step is 15 minutes or less. In another aspect, the cellulose is a cotton, rice, wheat, sugar cane, hemp, tree, algal or bacterial cellulose. In another aspect, the step of pre-treating is for 1, 2, 3, 4, 5, 6, 7, or 8 hours at a temperature between 15 to 30° C. In another aspect, the material is a fiber, a gel, a film, a resin, a powder, sheet, a ribbon, a mesh, a yarn, a flake, a foam, an emulsion, a fabric, a dispersion, a solution, a suspension, and any combination thereof. In another aspect, the temperature of dissolving is at 90-100° C. In another aspect, the step of dissolving is in the presence of microwave energy. In another aspect, the method further comprises the step of drying the cellulose between the pretreating and the dissolving steps. In another aspect, the imidazolium-based ionic liquid is a 1-alkylimidazolium. In another aspect, the 1-alkylimidazolium is selected from 1-methylimidazolium, 1-ethylimidazolium, 1-propylimidazolium, 1-butylimidazolium, 1-heptyl-3-methylimidazolium, 1-(cyclohexylmethyl)-3-methylimidazolium, 1-benzyl-3-methylimidazolium, 1,3-dibenzylimidazolium, 1-(2-napthylmethyl)-3-methylimidazolium, or 1,3-dibenzylimidazolium. In another aspect, the imidazolium-based ionic liquid, with acetate as the anion, is selected from at least one of 1-hepyl-3-methylimidazolium acetate ($[C_7C_1im][OAc]$), 1-(cyclohexylmethyl)-3-methylimidazolium acetate ($[CyhmC_1im][OAc]$), 1-benzyl-3-methylimidazolium acetate ($[BnzC_1im][OAc]$), 1,3-dibenzylimidazolium acetate ($[(Bnz)_2im][OAc]$), and 1-(2-napthylmethyl)-3-methylimidazolium acetate ($[NapmC_1im][OAc]$).

In another aspect, the method further comprises the step of regenerating the dissolved cellulose fibers by drawing, spinning, electrospinning, settling, layering, or matting. In another aspect, prior to pre-treatment the cellulose is at least one of scoured, bleached, air-dried, heat-dried, or ground. In another aspect, the imidazolium-based ionic liquid with acetate as the anion are pre-heated until fluid. In another aspect, the imidazolium-based ionic liquid with acetate as the anion are pre-heated to 70, 75, 80, 85, 90, 95, 96, 97, 97, 99, or 100° C. In another aspect, the method further comprises the step of regenerating the dissolved cellulose. In another aspect, the method further comprises the step of forming fibers, films, woven materials, knit materials, nonwoven materials, 3D materials, or membranes from the dissolved cellulose. In another aspect, the cellulose comprises a high molecular weight, a high degree of polymerization, and high crystallinity. In another aspect, the co-solvent is selected from at least one of DMSO, DMF, DMI, DMAc, or N-methylimidazole (MIM).

In another embodiment, the present invention includes a method of making a 1-alkylimidazolium comprising: mixing under an inert atmosphere 1-alkylimidazole in tetrahydrofuran (THF) with dimethylphosphite to form a mixture; refluxing the mixture to form the 1-alkylimidazolium in THF; removing the THF; washing the 1-alkylimidazolium with one or more volatile organic solvents; passing the mixture through a gravitational column; and evaporating the volatile organic solvents to leave an ionic liquid. In one aspect, the 1-alkylimidazolium is selected from 1-methylimidazolium, 1-ethylimidazolium, 1-propylimidazolium, 1-butylimidazolium, 1-heptyl-3-methylimidazolium, 1-(cyclohexylmethyl)-3-methylimidazolium, 1-benzyl-3-methylimidazolium, 1,3-dibenzylimidazolium, 1-(2-napthylmethyl)-3-methylimidazolium, or 1,3-dibenzylimidazolium. In another aspect, the 1-alkylimidazole is selected from at least one of a 1-methylimidazole, 1-ethylimidazole, 1-propylimidazole, 1-butylimidazole, 1-hepyl-3-methylimidazole, 1-(cyclohexylmethyl)-3-methylimidazole, 1-benzyl-3-methylimidazole, 1,3-dibenzylimidazole, or 1-(2-napthylmethyl)-3-methylimidazole. In another aspect, the volatile organic solvents are selected from at least one of toluene, hexane, dichloromethane, or diethyl ether, alone or in combination. In another aspect, the method further comprises the step of acetylating the 1-alkylimidazolium by mixing a 1-alkylimidazolium hydroxide with acetic acid under conditions that form the acetylated 1-alkylimidazolium. In another aspect, the method further comprises the step of forming a 1-alkylimidazolium is substituted with fluorine, chlorine, bromine, iodine, acyl, hydroxyl, or cyano groups.

In another embodiment, the present invention includes an ionic liquid comprising a 1-alkylimidazolium. In one aspect, the 1-alkylimidazolium is selected from 1-methylimidazolium, 1-ethylimidazolium, 1-propylimidazolium, 1-butylimidazolium, 1-heptyl-3-methylimidazolium, 1-(cyclohexylmethyl)-3-methylimidazolium, 1-benzyl-3-methylimidazolium, 1,3-dibenzylimidazolium, 1-(2-napthylmethyl)-3-methylimidazolium, or 1,3-dibenzylimidazolium. In another aspect, the 1-alkylimidazolium is in the form of an ionic liquid oil. In another aspect, the 1-alkylimidazolium is acetylated. In another aspect, the 1-alkylimidazolium is a 1-alkylimidazolium is optionally substituted with fluorine, chlorine, bromine, iodine, acyl, hydroxyl, or cyano groups.

BRIEF DESCRIPTION OF THE DRAWINGS

For a more complete understanding of the features and advantages of the present invention, reference is now made to the detailed description of the invention along with the accompanying figures and in which:

(FIG. 1a, FIG. 1e) before microwave, (FIG. 1b, FIG. 1f) after microwave, (FIG. 1c, FIG. 1g) 1 h at 90° C., (FIG. 1d) 4 h at 90° C., and (FIG. 1h) 2 h at 90° C.

FIG. 7A shows the FTIR spectra of ground cotton cellulose and freeze-dried cellulose regenerated after dissolution in [$C_4C_1$im][(OMe)(H)$PO_2$]. FIG. 7B shows the FTIR spectra of ground cotton cellulose and freeze-dried cellulose regenerated after dissolution of ethanol treated cotton in [$C_4C_1$im][(OMe)(H)$PO_2$]. FIG. 7C shows the FTIR spectra of ground cotton cellulose and freeze-dried cellulose regenerated after dissolution. FIG. 7D shows FTIR spectra using [$C_4C_1$im][(OMe)(H)$PO_2$] and 1-methyl imidazole. FIG. 7D is FTIR spectra of [$C_4C_1$im][(OMe)(H)$PO_2$] and 1-ethylimidazole. FIG. 7E shows the FTIR spectra of [$C_4C_1$im][(OMe)(H)$PO_2$] and 1-butylimidazole.

FIG. 8A shows the FTIR spectra of ethanol treated ground cotton cellulose and freeze-dried cellulose regenerated after dissolution in [$C_4C_1$im][(OMe)(H)$P_2$] and 1-methylimidazole. FIG. 8B shows the FTIR spectra of ethanol treated ground cotton cellulose and freeze-dried cellulose regenerated after dissolution in [$C_4C_1$im][(OMe)(H)$PO_2$] and 1-ethylimidazole.

(FIG. 14A) [$C_7C_1$im][OAc]; (FIG. 14B) [CyhmC$_1$im][OAc]; (FIG. 14C) [BnzC$_1$im][OAc]; (FIG. 14D) [NapmC$_1$im][OAc]; (FIG. 14E) [(Bnz)$_2$im][OAc].

FIG. 25A SEM 100× and FIG. 25B SEM 500×.

FIG. 27A SEM 100× and FIG. 27B SEM 500×.

FIG. 28A SEM 100× and FIG. 28B SEM 500×.

FIG. 29A SEM 100× and FIG. 291B SEM 500×.

FIG. 35 shows a general set-up of an electrospinning process.

FIGS. 36A and 36B show microscopic images of the material deposited on the glass slide from 5% (w/v) MCC in DMAc/LiCl with voltage at: (A) 15 kV/10 cm; (B) 16 kV/5.5 cm.

DETAILED DESCRIPTION OF THE INVENTION

Figures 1A, 1B, 1C, 1D, 1E, 1F, 1G, 1H:
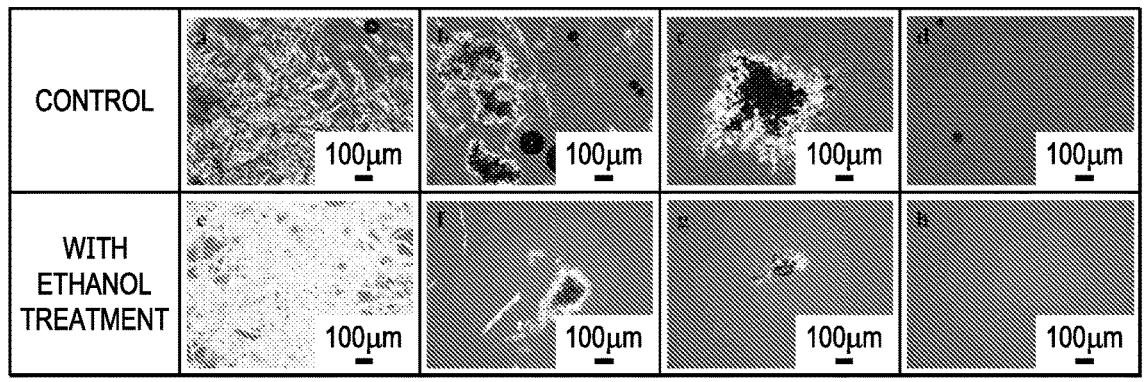
FIGS. 1A to 1H shows polarized light microscopy (PLM) images of cotton cellulose dissolved in [$C_4C_1$im][(OMe)(H)$PO_2$] without ethanol treatment/co-solvents (control) and with ethanol treatment.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the term "cellulose" refers to polysaccharides that are linear chains of several hundred to many thousands of β(1→4) linked D-glucose units. Cellulose is primarily made from plants, but is also available from algae and bacteria for use with the present invention. Typically, cellulose is mainly used to produce paperboard and paper, but can be converted into a wide variety of woven or non-woven derivative products such as cellophane and rayon. Non-limiting examples of plants from which cellulose can be obtained are trees, crop plants (such as, e.g., corn, wheat, sorghum, switchgrass, salix, poplar), or plants most often used for clothing such as cotton, hemp. Furthermore, cellulose can be used in the conversion of cellulose from energy crops into biofuels such as cellulosic ethanol. The dissolved cellulose materials of the present invention can be used for a wide variety of industrial, commercial, home, healthcare, dermal care, and other uses such as filters. Non-limiting examples of uses for cellulose include for use in cosmetics, cosmoceuticals, pharmaceutical formulations, adhesives, binders, consumables, bandages, thickening agents, 3-D printing, cellophane, linen, clothing, furnishings, woven products, knit products, non-woven products, absorbent or adsorbent materials for household or industrial use, in the form of powders, or the cellulose can be chemically modified. Non-limiting examples of chemical modifications to cellulose include but are not limited to cellulose acetate, cellulose triacetate, cellulose propionate, cellulose acetate propionate, nitrocellulose, cellulose sulfate, methylcellulose, ethylcellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, and/or carboxymethyl cellulose. The dissolved cellulose of the present invention provides a superior substrate for chemical modification. The dissolved cellulose (and modified cellulose) can also be formed into specific construction materials, due to the strength of cellulose and its ability to withstand dry and wet conditions, as well as being moldable into any of a variety of forms or spun into fibers to be used in materials such as non-wovens, wovens or knits. As a source of building materials, the cellulose can even be made fire retardant by the addition of fire retarding treatments such as with boric acid.

The dissolved cellulose of the present invention can be formed into, as a non-limiting example, wound care bandages that can be sterilized and may also be formed into a suture, a sheet, a compress, a bandage, a band, a prosthesis, a fiber, a woven fiber, a non-woven fiber, a woven fabric, a knit fabric, a non-woven fabric, a bead, a strip, a gauze or combinations thereof. A cellulose dressing may also include portions that are self-adhesive and/or an adhesive backing. The wound dressing may be a non-allergenic, multi-ribbon microbial cellulose substrate formed into a dressing that is molded to fit a specific wound site. In one embodiment, the present invention also includes a solid biocompatible implant that is a non-allergenic, multi-ribbon microbial cellulose substrate, wherein the implant is formed into a suture, a sheet, a compress, a bandage, a band, a prosthesis, a fiber, a woven fiber, a non-woven fiber, a woven fabric, a knit fabric, a non-woven fabric, a bead, a strip, clasp, prosthesis, catheter, screw, bone plate, pin, a bandage or combinations thereof. The cellulose may also be made from two or more different types of cellulose, or one or more types of cellulose combined with any other material appropriate for the application.

The dissolved cellulose of the present invention is a native biopolymer system with wide immune acceptance that may be molded into a wide variety of shapes, sizes, thicknesses, layers and the like. In fact, the cellulose may be manipulated during or after manufacturing to create specific nanostructures formulated for the site of implantation. One example is the formation of a cellulose from dissolved, re-precipitated celluloses, any regenerated cellulose, so long as the nanostructure can be arranged and generated, that offers maximal response from the cells involved with skin regeneration, e.g., fibroblast, stem cells, hair follicles and keratinocytes.

The dissolved cellulose of the present invention will also find particular uses in the production of biofuels, such as ethanol, from cellulose. Typically, large biomass is reduced in size, and using the present invention, can be dissolved into cellulose strands that are easier to process into biofuels. The bulk or reduced size cellulose can be dissolved using the present invention, can be separated from the ionic liquid (IL) and solvent (sometimes referred to as a co-solvent), washed, and further processed, while recycling the IL and solvent. The dissolved cellulose, the IL, and solvent can be separated by any number of methods, e.g., centrifugation, filtration, precipitation, separating mechanically, or other methods for separating the dissolved cellulose fibers from the ionic liquid and solvent mixture. Cellulose can be regenerated, for example, by drawing, spinning, electrospinning, settling, layering, or matting, but can also be concentrated, spun into yarns, formed into a shape (such as tubing, membranes, spheres, etc.), dried, formed into a scaffold, sheet, layer, or mat.

Different methods of dissolving different types of cellulose may lead to the final dissolved cellulose products having various properties. It is understood by those of skill in the art that the method used for cellulose dissolution in any particular case may be selected for, inter alia, any combination of time efficiency, cost efficiency, environmental safety, and/or for the properties of the final product produced by the method. For these reasons, the steps in the following dissolution methods can be mixed and matched to achieve various combinations of, inter alia, time efficiency, cost efficiency, environmental safety, and/or according to the final dissolved cellulose product desired. It is generally understood that if a cellulose with a high DP is used in a method for dissolution, a more robust and higher quality dissolved cellulose material will be achieved.

Example 1. Fast Dissolution of Cotton Cellulose in 1-Butyl-3-Methylimidazolium Methylphosphonate Cellulose is extremely difficult to dissolve in water and most common organic solvents. This chemical stability is due to its stiff crystalline structure and close chain packing via many inter- and intra-molecular hydrogen bonds. Furthermore, to fully dissolve cellulose, multi-step pretreatments followed by prolonged stirring are often required [1]. So far, a variety of cellulose solvent systems have been discovered, such as N-methylmorpholine-N-oxide (NMMO) [2], N,N-dimethylacetamide/lithium chloride (DMAc/LiCl) [3] [4], N,N-dimethylformamide/nitrous tetroxide (DMF/$N_2O_4$) [5], 1,3-dimethyl-2-imidazolidinone/lithium chloride (DMI/LiCl) [6], dimethylsulfoxide/tetrabutylammonium fluoride (DMSO/TBAF) [7], ammonia salt ($NH_3/NH_4SCN$) [8], inorganic molten salt hydrates [9] [10] and ionic liquids [11] [12].

Ionic Liquids (ILs) have been widely investigated as interesting class of solvents for cellulose dissolution studies, although such work has been performed primarily using low DP cellulose. ILs, also known as room temperature ILs (RTILs), are organic salts that exist as liquids at relatively low temperatures (<100° C.) [13]. ILs have several inherent characteristics such as chemical and thermal stability, non-flammability and immeasurably low vapor pressure, enabling possible recycling, relatively high ionic conductivity and high solvation ability [14, 15]. The ILs that are readily available for cellulose dissolution mainly comprise of an organic cation, and an inorganic or organic anion [16]. Most commonly used organic cations such as imidazolium, pyridinnium, ammonium and phosphonium can be combined with a variety of anions including basic halides or more evolved organic/inorganic moieties, resulting in a large number of possible combinations [17]. Interestingly, there is a great opportunity to design and tune many of their physicochemical properties such as density, polarity, viscosity, melting point, and solubility by selecting proper cation and anions combinations [1, 14, 16, 18] depending on the various applications in different fields, including extraction [19, 20], tribology [21], electrochemistry [22], catalysis [23, 24], biomass processing [25] and organic synthesis [26]. Imidazolium salts are one class of ILs [27]. However, the properties of the resulting combinations are not always predictable. In 2002, Swatloski and co-workers reported dissolving cellulose in a series of imidazolium-based ILs. They demonstrated that 1-butyl-3-methylimidazolium chloride ($[C_4C_1im][Cl]$) could dissolve up to 10 wt. % of pulp cellulose with a degree of polymerization of (DP) of 1000 at 100° C. [28]. Since then, many kinds of ILs have been synthesized that have the potential to dissolve cellulose by serving as a reaction medium to functionalize cellulose [29] [30] [31]. Zhang et al. in 2005 synthesized a powerful solvent, 1-allyl-3-methylimidazolium chloride ([Amim][Cl]) for cellulose dissolution which dissolved 5 wt. % dissolved pulp (DP of 650) and cotton linters (DP of 1600) within 30 minutes at 80° C. and within 120 minutes at 110° C. respectively [32]. Interestingly, 1-ethyl-3-methylimidazolium methylphosphonate ($[C_2C_1im][(MeO)_2PO_2]$) solubilizes 2-4 wt. % of microcrystalline cellulose (DP of 200-250) with stirring at 45° C. for 30 minutes [1]. Moreover, 4 wt. % cotton—ramie pulp with a DP of 575.6 was dissolved in 1-ethyl-3-methylimidazolium diethylphosphonate ($[C_4C_1im][DEP]$) within 10 minutes under 90° C. [33].

However, the efficacy of ILs as direct solvents for cellulose dissolution is limited by properties such as the viscosity of the neat ILs and the corresponding cellulose solutions [34]. In addition, the slow rate of dissolution [13] and low miscibility of the ILs with certain hydrophobic regents and cellulose derivatives [34] limit the solvation ability of the IL with cellulose. Previous studies have shown that the addition of several organic solvents to ILs has considerably improved cellulose dissolution [35] [36] [37]. Some of these solvents which demonstrate high polarity and aprotic nature are classified as co-solvents including DMSO, DMF, DMI, DMAc and N-methylimidazole (MIM). The function of the co-solvent in cellulose dissolution is not yet understood but, several scientists have suggested that it avoids the agglomeration of cellulosic fibers upon mixing in ILs [35], facilitates mass transport by decreasing the solvent viscosity [36]

and increases the concentration of the "free" anions from the dissociated IL by the solvation of cation by the co-solvent [37] [38].

In 2010, Rinaldi developed solvent systems that have higher dissolution rates and lower viscosity than the neat ILs. In these studies, Ig of cellulose (Avicel) was immersed in DMI for 16 hours under magnetic stirring at 100° C. followed by adding solid [$C_2C_1$im][Cl]. They were able to completely dissolve cellulose within 3 minutes, whereas the neat IL took more than 10 hours to dissolve the same concentration of cellulose in same conditions. It was further demonstrated that the solubility of cellulose is most efficient when the molar fraction of DM: IL ($X_H$) is 0.40 [35]. Later on, Xu et al. reported that [$C_2C_1$im][$CH_3COO$]+DMSO/ DMF solvents effectively dissolved cellulose at ambient temperature without any heating [37] [39, 40]. According to their studies, 15.0% and 13.0% MCC were completely dissolved in 7.67:1 molar ratio of [$C_4C_1$im][OAc]/DMSO ($\chi_{DMSO}$=2.54:1) [37] and 2.71:1 molar ratio of [$C_4C_1$im][OAc]/DMF ($\chi_{DMSO}$=2.71:1) respectively at 25° C. [40]. In the same year, they demonstrated that 9.0% MCC could dissolve in [$C_4C_1$im][OAc]/DMAc ($\chi_{DMAc}$=1.14:1) [39]. Andanson et al. in 2014 have shown that addition of DMSO to IL 1-butyl-3-methylimidazolium acetate ([$C_4C_1$im][$CH_3COO$]) made low DP cellulose dissolve much faster and at lower temperatures. Molecular dynamic experiments performed by them indicated that equimolar mixture of IL and DMSO did not interact with glucose and completely dissolved 5 and 10 wt. % of a low DP microcrystalline cellulose (MCC) at temperatures close to 60° C. in less than 30 minutes [36]. Moreover, the extensive studies have shown that the addition of MIM as a co-solvent to IL, 1-ethyl-3-methylimidazolium acetate ([$C_2C_1$im][OAc]) provided better solubility of cellulose than DMSO and DMAc [41].

Pretreatment methods are another strategy, which are being used to improve cellulose dissolution by reducing the dissolution time. The common pretreatment methods that have been reported in the literature for cellulose dissolution are microwaving [28], mechanical milling [42], freeze-drying [8] and ultra-sonication [43]. Studies conducted by Roger's group have demonstrated that microwave is more efficient than oil-bath heating in dissolving raw lignocellulosic biomass or chitinous biomass [11]. Microwave heating reduces the heat transfer problems because microwave energy can easily and rapidly penetrate to particles inside. Therefore, all particles can be heated simultaneously and uniformly [44].

Extensive studies performed by Lan and his coworkers have shown that mechanical milling reduced the time for cellulose dissolution [42]. This could be due to the reduced particle size, which leads to the increase of the surface area being in contact with the solvents. The present inventors have demonstrated that freeze-drying pretreatment has a potential to enhance the dissolution of cellulose compared to the conventional hot-drying method. In freeze-drying process, water that occupies the interfibrillar space in cellulose gets sublimated without collapsing them. This process creates a porous structure on the cellulose [8].

Mikkola et al. in 2007 and Lan et al. in 2011 have demonstrated that high-power ultrasound dramatically intensify the cellulose dissolution process [43, 45]. This could be due to the greater penetration of IL into cellulose and improved mass transport [42].

Besides the previously mentioned pretreatment methods, ethanol treatment was reported as one of the effective and feasible methods that boosts cellulose dissolution [42]. During this method, free water and bound water in cellulose is replaced by ethanol which results in a loosen and porous structure and facilitates the penetration of IL into cellulose [42].

In the following examples, the present inventors used cotton cellulose. However, it is understood that the same methods apply to any high DP cellulose. To improve on the known methods for dissolving cellulose, the inventors dissolved 5 wt. % cotton cellulose in the IL 1-butyl-3-methylimidazolium phosphonate ([$C_4C_1$im][(OMe)(H)$PO_2$]). This IL has not previously been reported as a solvent for cellulose dissolution. This IL was designed based on properties of the cation and the anion such as the length of the alkyl chain on the imidazolium ring, the basicity and the polarity.

Pretreatment with alcohol. To enhance the dissolution, the present inventors used a pretreatment step, in which an alcohol (such as ethanol, 1-propanol, iso-propanol, or tert-butanol) treatment was applied to accelerate cellulose dissolution with the same IL. Subsequently, cotton cellulose was dissolved in an equimolar ratio of IL and co-solvents N-methyl imidazole (1-methylimidazole, 1-ethylimidazole and 1-butylimidazole).

In another example, both pretreatment methods were combined with the addition of co-solvents to investigate the effect on the rate of dissolution in the given IL. For each study, the same concentration of cotton cellulose (5 wt. %) was used. The regenerated cellulose samples obtained from these dissolution studies are numbered and described in Table 1.

TABLE 1

Dissolution and regeneration of cotton cellulose in [$C_4$mim][(OMe)(H)$PO_2$].

| Sample number | Dissolution and Regeneration |
| --- | --- |
| 1 | Cotton in [$C_4C_1$im][(OMe)(H)$PO_2$] |
| 2 | Ethanol treated cotton in [$C_4$mim] [(OMe)(H)$PO_2$] |
| 3 | Cotton in [$C_4C_1$im][(OMe)(H)$PO_2$] + 1-methylimidazole |
| 4 | Cotton in [$C_4C_1$im][(OMe)(H)$PO_2$] + 1-ethylimidazole |
| 5 | Cotton in [$C_4C_1$im][(OMe)(H)$PO_2$] + 1-butylimidazole |
| 6 | Ethanol treated cotton in [$C_4C_1$im][(OMe)(H)$PO_2$] + 1-methylimidazole |
| 7 | Ethanol treated cotton in [$C_4C_1$im][(OMe)(H)$PO_2$] + 1-ethylimidazole |

Synthesis of ionic liquids. 1-Butylimidazole (98%) and dimethyl phosphite (98%) were purchased from Sigma-Aldrich. Dichloromethane (DCM), acetonitrile and toluene were separately distilled over $CaH_2$ under nitrogen and diethyl ether was distilled over Na/benzophenone. THF and hexanes were distilled under nitrogen from alkali metals and stored over 4 Å molecular sieves prior to use. For the gravitational column chromatography, Celite (Fisher), Sand (Macros), Aluminum Oxide (60 A, activated, basic, 50-200 micron, Acros) and glass wool were used. The IL was dried in a vacuum oven at 80° C. for 24 h. After drying, water contents (less than 200 ppm, measured by Karl Fisher titration (Karl Fisher METTLER TOLEDO C20 coulometric KF titrator), and other impurities (undetectable, measured by NMR, JOEL 400 MHz spectrometer) were determined. $^1$H NMR, $^{13}$C NMR, spectra were recorded on a JEOL ECS 400 MHz spectrometer. For H NMR spectra, tetramethylsilane (TMS, δ=0.00) or the residual protic solvent peak (for ($CD_3$)$_2$CO, δ=2.05), for $^{31}$P NMR $H_3PO_4$ and for $^{13}$C NMR spectra tetramethylsilane (TMS, δ=0.00) or the residual protic solvent peak (for ($CD_3$)$_2$CO, δ=29.84) served as a shift reference. Coupling constants, J, are reported in hertz. All reaction vessels were flame-dried under vacuum and filled with nitrogen prior to use. All reactions were performed under a nitrogen atmosphere as a routine practice, not as an essential requirement. The inventors used a similar synthetic protocol to the one developed by Ohno and coworkers for the synthesis of 1-ethyl-3-methylimidazolium methyl phosphonate [1].

1-butyl-3-methylimidazolium methylphosphonate [$C_4C_1$Im][(MeO)(H)$PO_2$]. Under inert atmosphere, 250 mL two-necked round bottom flask with a magnetic stir bar was charged with 1-butylimidazole (12.4 g, 99.8 mmol) in THF (25 mL). A solution of dimethylphosphite (10 g, 90.8 mmol) in THF (20 mL) was added dropwise via an addition funnel (2 mL/min) at room temperature. The reaction mixture was refluxed at 90° C. for 3 days. The progress of the reaction was monitored by $^1$H NMR. After the completion of the reaction, the desired product was isolated by removing THF under vacuum. The crude material was washed with toluene/hexane 1:1 mixture and diethyl ether repeatedly, followed by the addition of activated carbon in dichloromethane and stirring for 3 days. The mixture was then passed through a gravitational column packed with alumina, celite, sand and glass wool. The product was isolated by removing dichloromethane and acetonitrile using rotary evaporation. The pure IL was isolated as a colorless oil. The trace amounts of solvents and volatiles were removed under high vacuum (ca. $10^{-1}$ mbar) at 80° C. in an oil bath for 24 hours. The product was characterized by $^1$H, $^{13}$C and $^{31}$P NMR. $^1$H NMR (400 MHz; $(CD_3)_2$CO; TMS) 0.89 (t, J=7.2 Hz, 3H, $CH_2CH_3$), 1.16 (m, J=7.0 Hz, 2H, $CH_2CH_2CH_3$), 1.80 (m, 2H, $CH_2$), 3.26 (d, J=21 Hz 3H, PO—$CH_3$), 3.80 (s, 3H, J=7.0 Hz, N—$CH_3$), 4.10 (t, 2H, J=7.0 Hz, N—$CH_3$), 6.50 (d, H, J=550.0 Hz, P—H) 7.35 (d, 2H, J=12.0 Hz, NCHCHN), 10.35 (s, 1H, NCHN) ppm. $^{13}$C NMR, $(CD_3)_2$CO, 100 MHz): 13.0 ($C_3H_7$-$CH_3$), 19.2 (~$CH_2$—$CH_3$), 28.9 ($CH_2$—$CH_2CH_3$), 50.0 (PO$CH_3$), 35.5 (N—$CH_3$), 48.8 (N—$CH_2$), 122.5 (NCHCHN), 123.8 (NCHCHN), 138.8 (NCHN) ppm. $^{31}$P NMR, $(CD_3)_2$CO, 162 MHz) 4.0 ppm.

Preparation of cotton fibers for dissolution. Cotton fibers were obtained from the Fiber and Biopolymer Research Institute, Texas Tech University. The fibers were scoured, bleached, air-dried, and ground by a Wiley mill, or equivalent, to pass through a 20 mesh screen. They were dried at 105° C. overnight in a laboratory oven.

Ethanol treatment of cellulose. Scoured, bleached and air-dried cotton was ground by Wiley mill as mentioned above. Cotton was then immersed in absolute ethanol and stirred at room temperature for 4 hours. The sample was filtered by Buchner funnel and dried at 105° C. oven for 2 hours.

Previously, the ethanol-treatment was carried out for 2 hours at 105° C. The inventors have extended the duration of ethanol-treatment time from 2 to 8 hours at low temperature of 55° C. in order to decrease the rate of ethanol evaporation from cotton cellulose.

Due to improved physical characteristic of the regenerated cellulose (films were formed with structural integrity), lower temperature (55° C.) for a longer period of time (8 hours) to evaporate the ethanol.

Dissolution of ground cotton fibers in IL. Dissolution of ground cotton fibers in neat IL. The IL and ground cotton fiber (5 wt. %) were measured separately and the ground cotton fiber samples were slowly added into the ILs. The dispersion were heated to 90-100° C. with several 3-5 sec pulses in a microwave oven. The mixture were heated at 90° C. until a complete dissolution was achieved. Ethanol treated cotton was also dissolved in the same way.

Dissolution of ground cotton fibers in the mixture of IL and co-solvents. The imidazole co-solvent and IL were mixed together in 1:1 molar ratio. For example, 1-methylimidazole, 1-ethylimidazole, and 1-butylimidazole, were added in to three separate glass jars. Cotton was weighed and slowly added into the IL/imidazole mixtures with constant stirring. The dissolution of cotton was performed as mentioned above.

Dissolution of ethanol treated ground cotton fibers in the mixture of IL and co-solvents. Ethanol treated cotton was dissolved in 1:1 molar ratio of IL and 1-methylimidazole and 1-ethylimidazole. The dissolution experiments were carried out using the same procedure mentioned above.

Polarized light microscopy (PLM). Representative samples of the solution were taken in different time intervals. The mixtures were stirred well before the samples were collected. The dissolution processes in different ILs were observed by a Nikon ECLIPSE LV 100 polarizing light microscope with NIS-Elements imaging platform. The images were recorded at the room temperature under ×10 magnification.

Regeneration of cellulose from the mixtures. Each cotton-IL solution was poured onto a glass slide and covered with another glass slide. They were allowed to spread uniformly by gentle pressing the glass slides. The glass slides that contained cotton-IL were kept in a glass jar. Deionized water was poured into the glass slides to regenerate cellulose from the solutions. The ILs were rinsed away from the regenerated cellulose by changing deionized water for 3-4 days.

Freeze drying the regenerated cellulose. Regenerated cellulose from different ILs were kept at −4° C. for 2 h and dried using a Labconco FreeZone (4.5 Liter Cascade Benchtop Freeze Dry System) at −102° C. and 0.05 mbar for 3 days.

Characterization of the regenerated cellulose by scanning electron microscopy (SEM). Freeze dried regenerated cellulose samples were mounted on carbon discs without a coating prior to obtaining images. The scanning electron micrographs were recorded using a Hitachi TM-1000 tabletop environmental scanning electron microscope at an accelerating voltage of 15 kV.

Fourier transform infrared spectroscopy (FTIR). FTIR spectra of all regenerated cellulose samples, hot-dried cotton and ethanol treated cotton were collected using a PerkinElmer Spectrum 400 FTIR spectrometer equipped with a universal attenuated total reflectance (UATR) accessory. The samples were conditioned at 21±1° C. at 65±2% relative humidity for 2 days prior to the FTIR analysis. The samples were placed on cleaned Zn-diamond crystal stage and a force was applied by a "pressure arm" to maintain a constant pressure on the sample to provide a good contact between the sample and the incident IR beam. The spectra were collected in the mid-IR range from 650-4000 $cm^{-1}$ at a resolution of 4 $cm^{-1}$ with 32 co-added scans. Then they were subjected to baseline correction and normalization using Perkin-Elmer software.

Nitrogen adsorption-desorption measurements. Nitrogen adsorption-desorption isotherms for samples 6 and 7 were obtained at −196° C. on a Gemini VII 2390 surface Area Analyzer (micrometrics, GA). Prior to the measurements, the samples were degassed at 120° C. for 8 hours. Brunauer-Emmet-Teller (BET) analysis was used to measure the surface area and cumulative surface area and cumulative volume of pores were measured by Barret-Joyner-Halendar (BJH) analysis.

Polarized light microscopy of progress of cellulose dissolution. FIGS. 1A to 1H show the PLM images recorded for 5% (w/w) mixtures for ethanol treated and untreated cotton dissolved in [$C_4C_1$im][(OMe)(H)$PO_2$] at different time intervals: before microwaving (1a,e), after microwaving (FIG. 1B, FIG. 1F), after 1 h of heating at 90° C. (FIG. 1C, FIG. 1G) after 4 h of heating at 90° C. (FIG. 1D); and after 2 h of heating at 90° C. (FIG. 1H). Due to the extensive crystalline structure of cellulose, fibers could be visualized by PLM. As the dissolution proceeded, the crystalline structure was destroyed and fibers gradually disappeared from the imaging screen. PLM images FIG. 1A to 1D provide references to compare the state of cotton fiber-IL mixtures during different dissolution studies with ethanol treatment and co-solvents. From the images before and after microwaving (FIGS. 1A, 1B, 1E, 1F) it can be observed that microwave heating drastically dissolved cotton fibers in the IL regardless of the treatment method. The PLM images show that heating at 90° C. for 1 h allows dissolving the ethanol treated-cotton fibers faster than cotton fibers. Complete dissolution of ethanol-treated cotton in [$C_4C_1$im][(OMe)(H)$PO_2$] was achieved within 2 h, which is a remarkable decrease in time as compared to the control.

Figure 2:
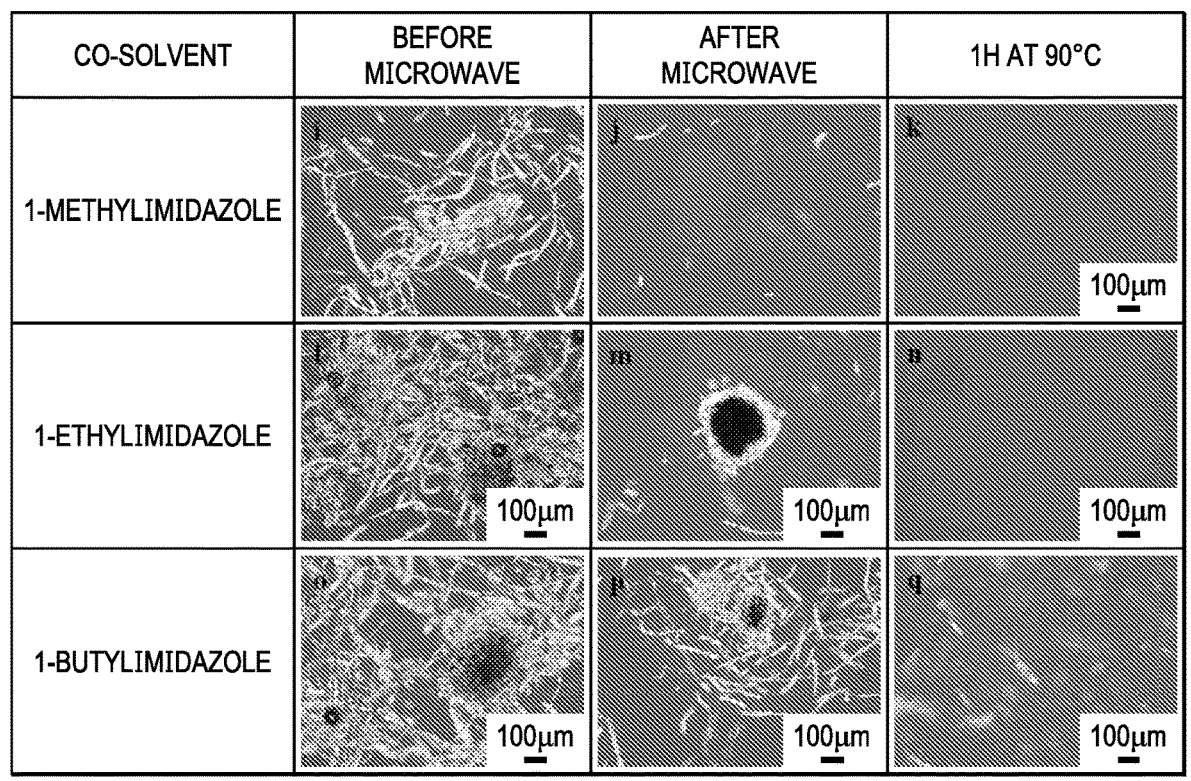
FIG. 2 shows PLM images of cotton cellulose dissolved in [$C_4C_1$im][(OMe)(H)$PO_2$] and co-solvents at different stages of dissolution.

FIG. 2 shows the PLM images of the cotton-IL-co-solvent mixtures at different time intervals of dissolution for the three co-solvents. As it can be seen in PLM images, after microwaving (FIGS. 2J, 2M, and 2P) different extent of dissolution of cotton fibers occurred depending on the co-solvent. In the case of 1-methylimidazole, relatively high dissolution occurred after microwaving as compared to 1-ethylimidazole and 1-butylimidazole. Interestingly, complete dissolution was achieved in 1-methylimidazole and 1-ethylimidazole within 1 h. However, 1-butylimidazole showed a low degree of dissolution as evidenced by regions showing un-dissolved fibers. The addition of co-solvents to the IL has noticeably improved the dissolution compared to the control. The degree to which the dissolution has occurred after 1 h at 90° C. follows the trend: 1-methylimidazole≈1-ethylimidazole>>1-butylimidazole>control.

Figure 3:
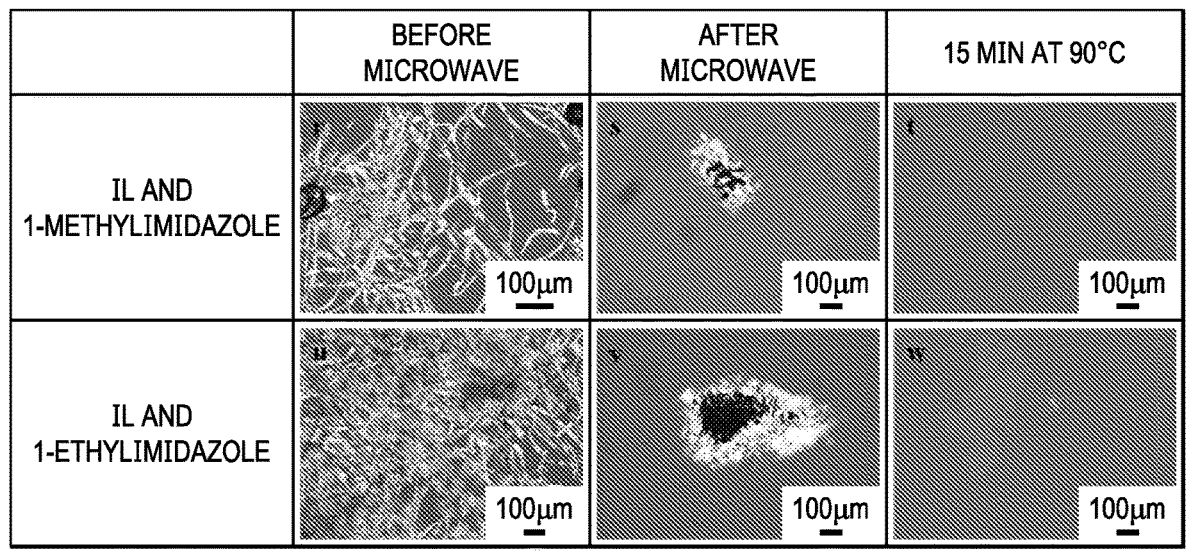
FIG. 3 shows PLM images of ethanol treated cotton cellulose dissolved in [$C_4C_1$im][(OMe)(H)$P_2$] and co-solvents at different stages of dissolution.

Depicted in FIG. 3 are the PLM images representing the progress of the dissolution of ethanol treated cotton in two co-solvents, 1-methylimidazole and 1-ethylimidazole. It is evident that, the combined method dramatically improved the dissolution of cotton cellulose within 15 min (FIGS. 3t, w).

According to the literature, ethanol treatment and co-solvent were independently used to dissolve sugarcane bagasse (DP=1263) and microcrystalline cellulose (DP=229) respectively in which DP is greatly lower than cotton cellulose. Thus, the inventors were able to completely dissolve ground cotton, in which DP is 3800-5500.

Dissolution of raw cotton fibers. In this study, cotton fibers were used "as is" (not ground). The degree of polymerization of raw cotton fibers is between 8,000 and 12,000. Cotton fibers were pre-treated with ethanol and dissolved in 1-butyl-3-methylimidazolium phosphate+1-methylimidazole.

Figures 4A, 4B, 4C:
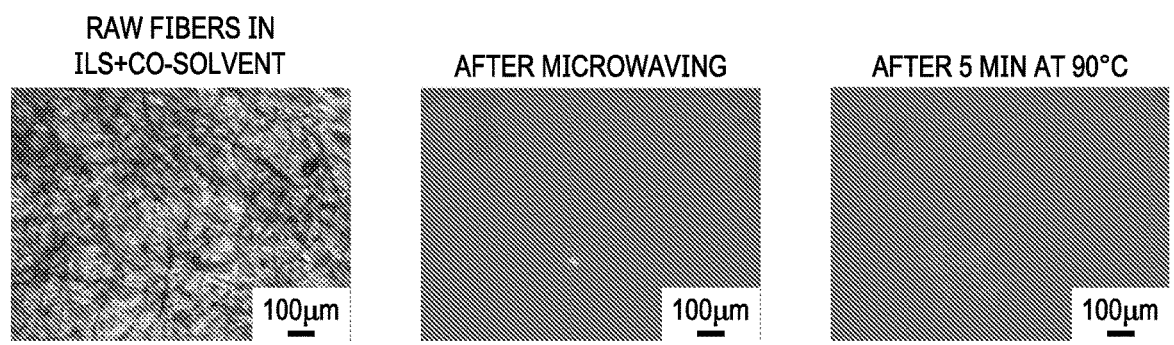
FIGS. 4A to 4E show PLM images of ethanol treated raw cotton cellulose dissolved in [$C_4C_1$im][(OMe)(H)$P_2$] and the co-solvent 1-methylimidazole at different stages of dissolution.
Figures 4D, 4E:
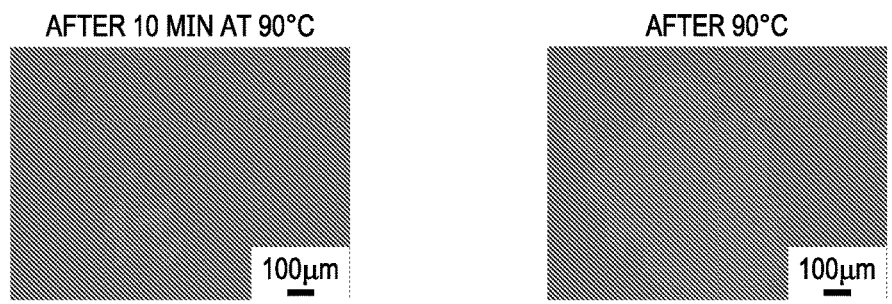

FIG. 4 shows that even for raw cotton fibers (having an extremely high degree of polymerization), fibers can be completely dissolved after only microwaving, omitting the step of heating at 90° C. in an oven. FIGS. 4A to 4E show PLM images of ethanol-treated raw cotton cellulose dissolved in [$C_4$mim][(OMe)(H)$PO_2$] and co-solvent 1-methylimidazole at different stages of dissolution.

Figure 5A:
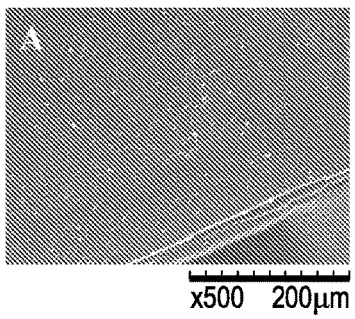
FIGS. 5A to 5G show scanning electron micrographs of the topography of regenerated cellulose films obtained from samples 1-7 shown in (5A)-(5G), respectively.
Figure 5B:
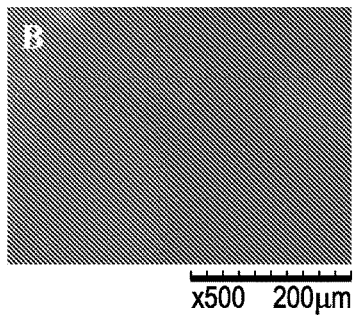
Figure 5C:
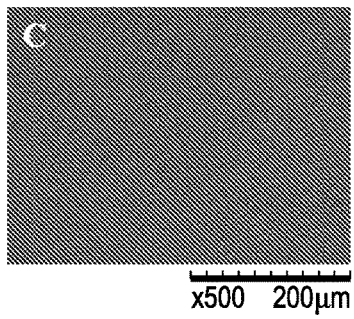
Figure 5D:
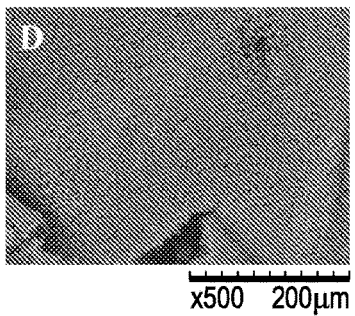
Figure 5E:
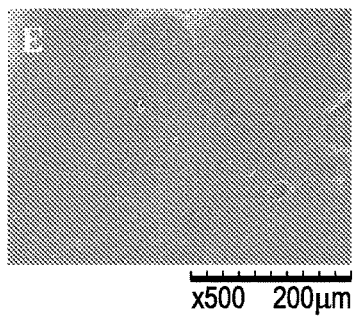
Figure 5F:
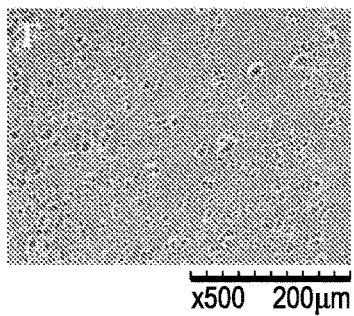
Figure 5G:
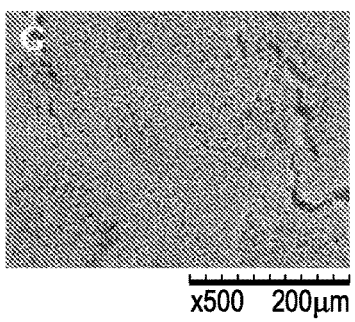

Characterization of the structure and surface morphology of regenerated cellulose. Scanning Electron Micrographs. The surface morphology of regenerated cellulose films were investigated under the ×500 objective magnification of SEM. FIGS. 5A to 5G are scanning electron micrographs of topography of regenerated cellulose films obtained from samples 1-7 shown in (A)-(G). FIGS. 5A to 5G show the results from regenerated cellulose obtained from samples 1-7, respectively. The absence of un-dissolved cotton fibers in SEM images (FIGS. 5A-D, 5F, 5G) indicates a complete dissolution, which is consistent with PLM observations. In contrast, FIG. 5E shows un-dissolved fibers, indicating an incomplete dissolution. Cellulose regenerated from all the samples form uniform and homogeneous films. This uniformity is an indicator of a dense texture in the cellulose. Additionally, SEM images also show that regenerated cellulose films 5(D), (F), (G) have porous structures.

Figure 6:
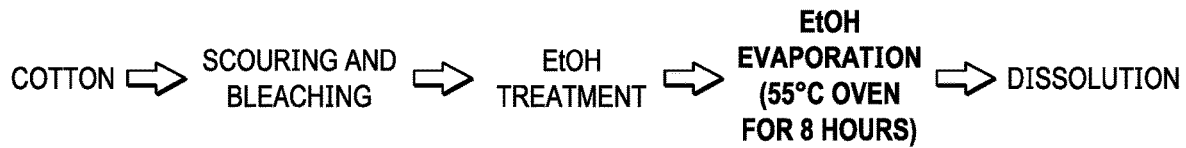
FIG. 6 is a flowchart of one method of the present invention.

FIG. 6 shows a flowchart of one method of the present invention.

FTIR Characterization. FTIR spectra of native cotton/ethanol treated cotton and regenerated cellulose of samples 1-5 are shown in FIGS. 7A-7E. The spectra for cotton/ethanol treated cotton provide references for comparaison with the spectra of regenerated cellulose. There are no significant changes in both spectra for all samples indicating that the chemical structure of cotton cellulose was preserved after dissolution and regeneration. However, the spectra for regenerated cellulose of these samples exhibit few changes in their vibrations at 345-3490 $cm^{-1}$ and 3435-3441 $cm^{-1}$ regions regardless of ethanol treatment or the addition of co-solvents (See FIGS. 5A-5E). These changes indicate that the intra- and inter-molecular hydrogen bonding patterns were affected by dissolution and regeneration processes. In addition, FTIR spectra for regenerated cellulose samples show similar changes in their vibrations at 1640, 1428, 1315, 1159, 1104, 1052, 895 and 707 $cm^{-1}$ when compared with the spectra of native cotton/ethanol treated cotton. Particularly, the band of the C—O—C vibration stretching in β-glycosidic linkage of the regenerated cellulose (895 $cm^{-1}$) shifted to a lower wavenumber and became narrower. This suggests the presence of a more amorphous morphology in the regenerated cellulose.

Figure 7A:
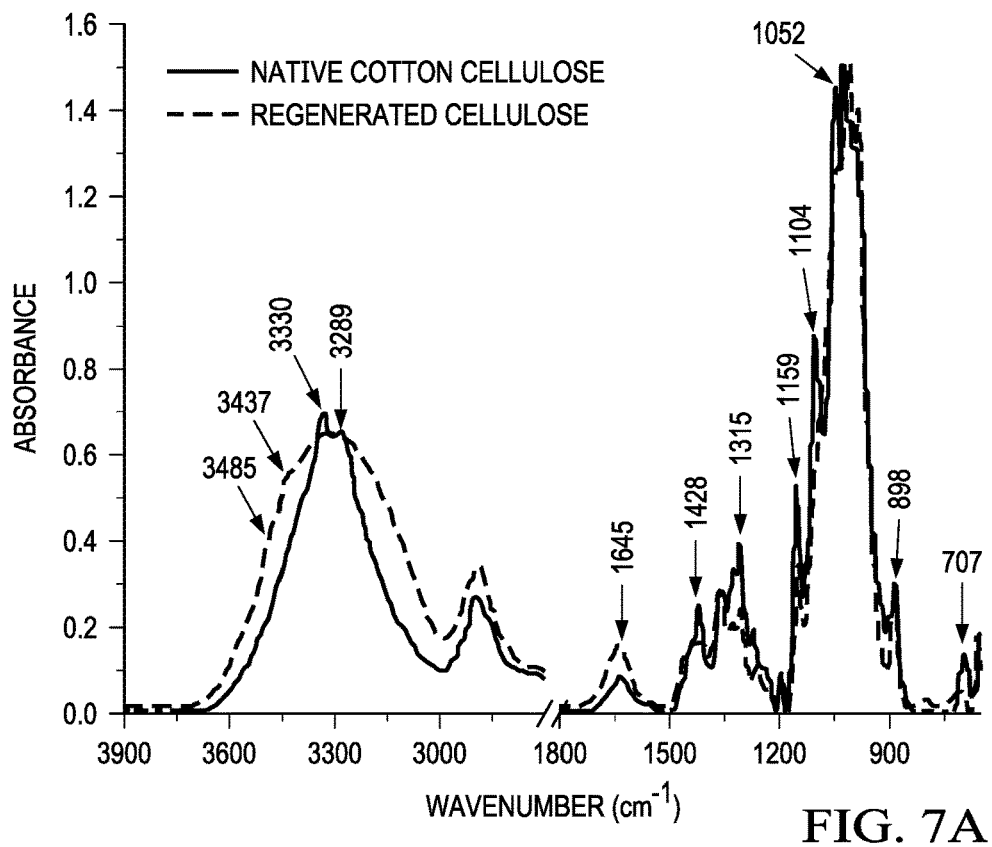
FIGS. 7A to 7E show.
Figure 7B:
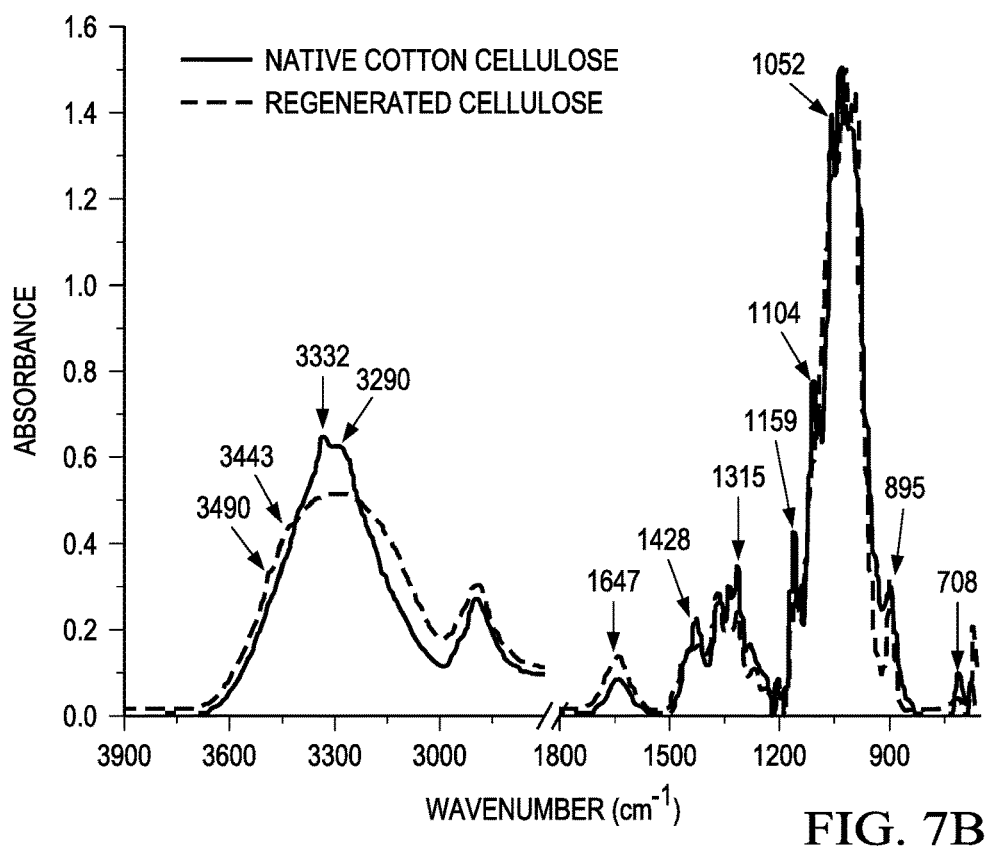
Figure 7C:
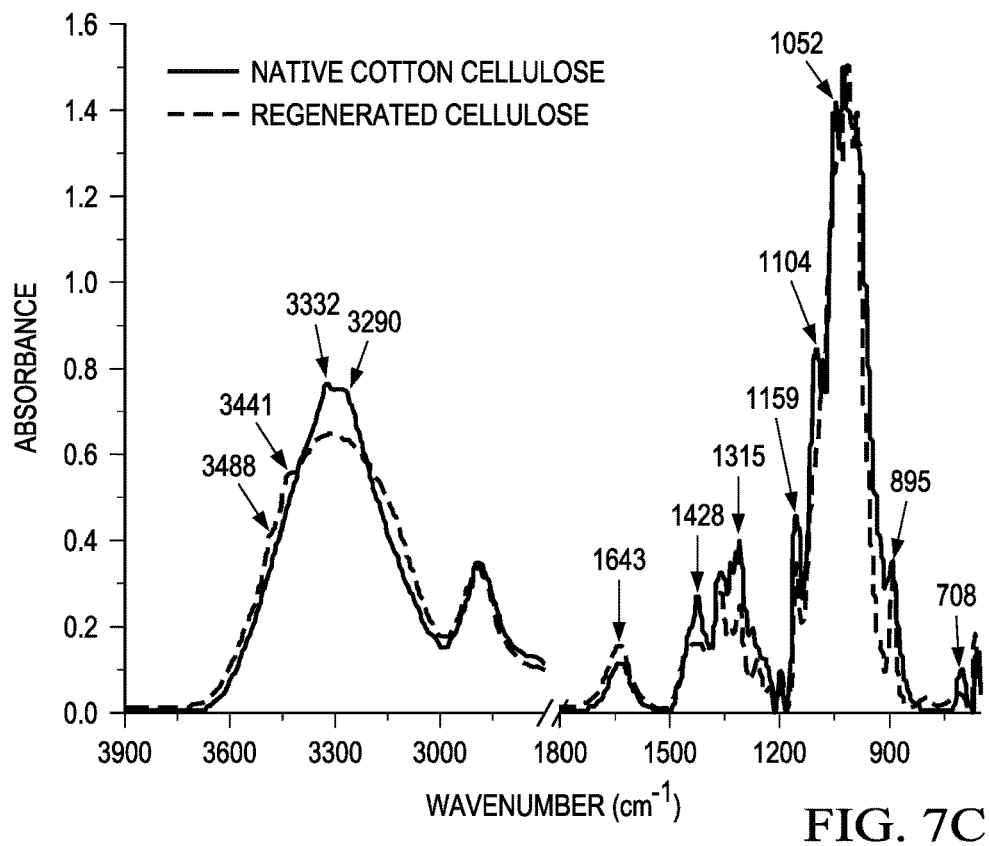
Figure 7D:
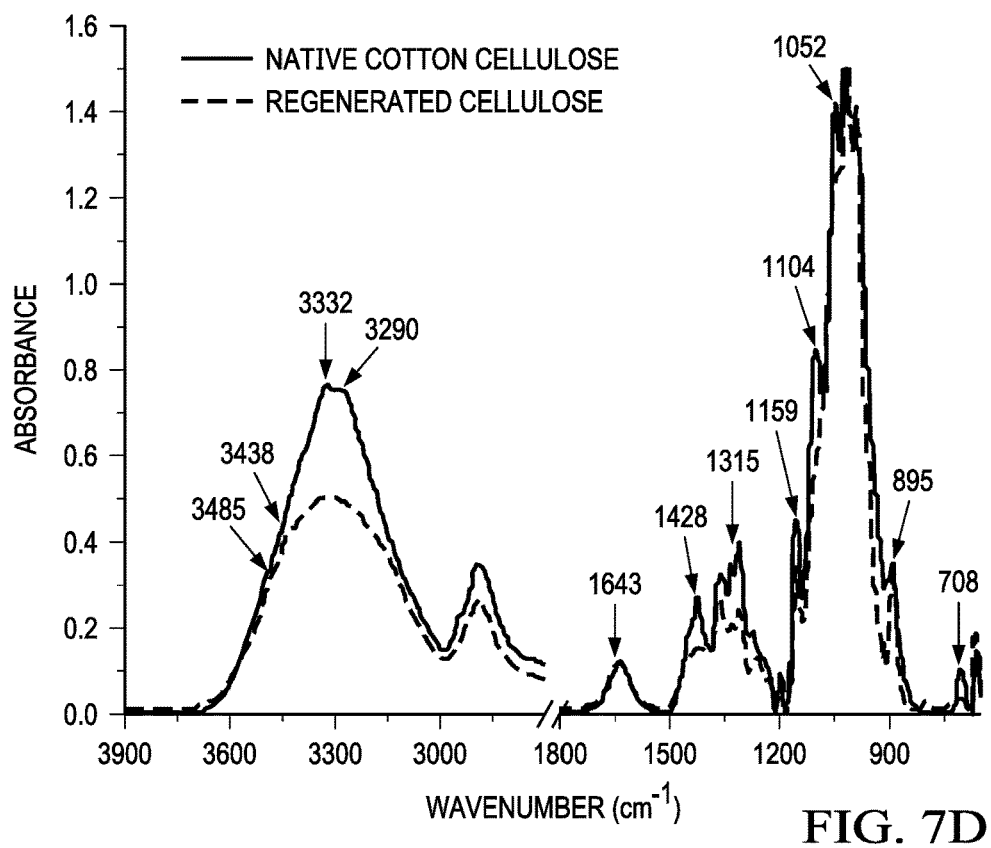
Figure 7E:
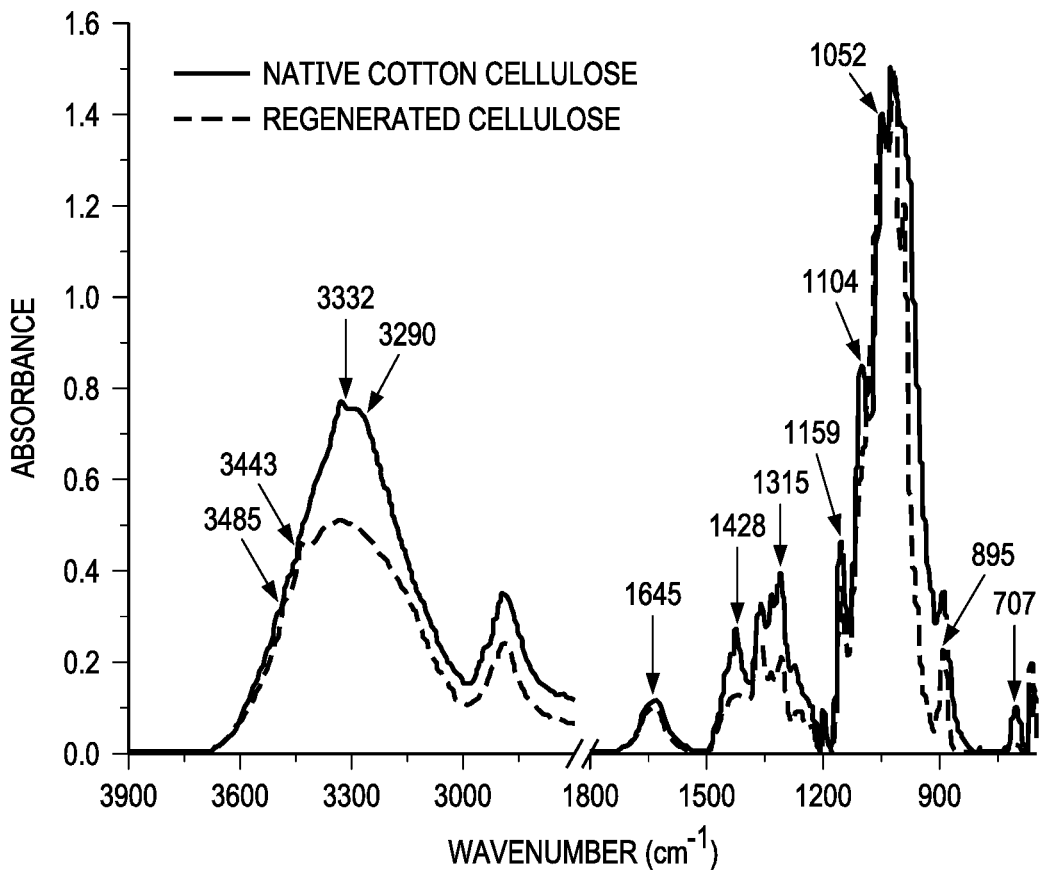

FIGS. 7A to 7E show FTIR spectra. FIG. 7A is an FTIR spectra of ground cotton cellulose and freeze-dried cellulose regenerated after dissolution in [$C_4C_1$im][(OMe)(H)$PO_2$]. FIG. 7B shows FTIR spectra of ground cotton cellulose and freeze-dried cellulose regenerated after dissolution of ethanol treated cotton in [$C_4$mim][(OMe)(H)$PO_2$]. FIG. 7C shows FTIR spectra of ground cotton cellulose and freeze-dried cellulose regenerated after dissolution in [$C_4$mim][(OMe)(H)$PO_2$] and 1-methylimidazole. FIG. 7D [$C_4C_1$im][(OMe)(H)$PO_2$] and 1-ethylimidazole. FIG. 7E. [$C_4C_1$im][(OMe)(H)$PO_2$] and 1-butylimidazole.

Figure 8A:
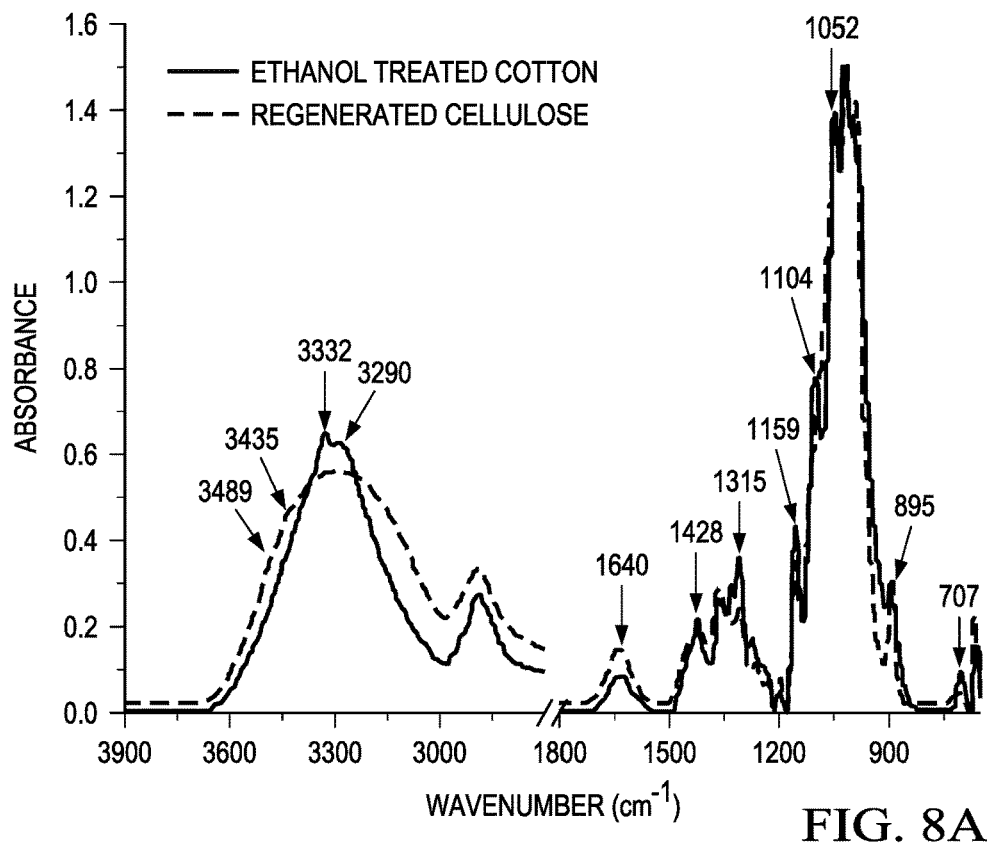
FIGS. 8A and 8B show.
Figure 8B:
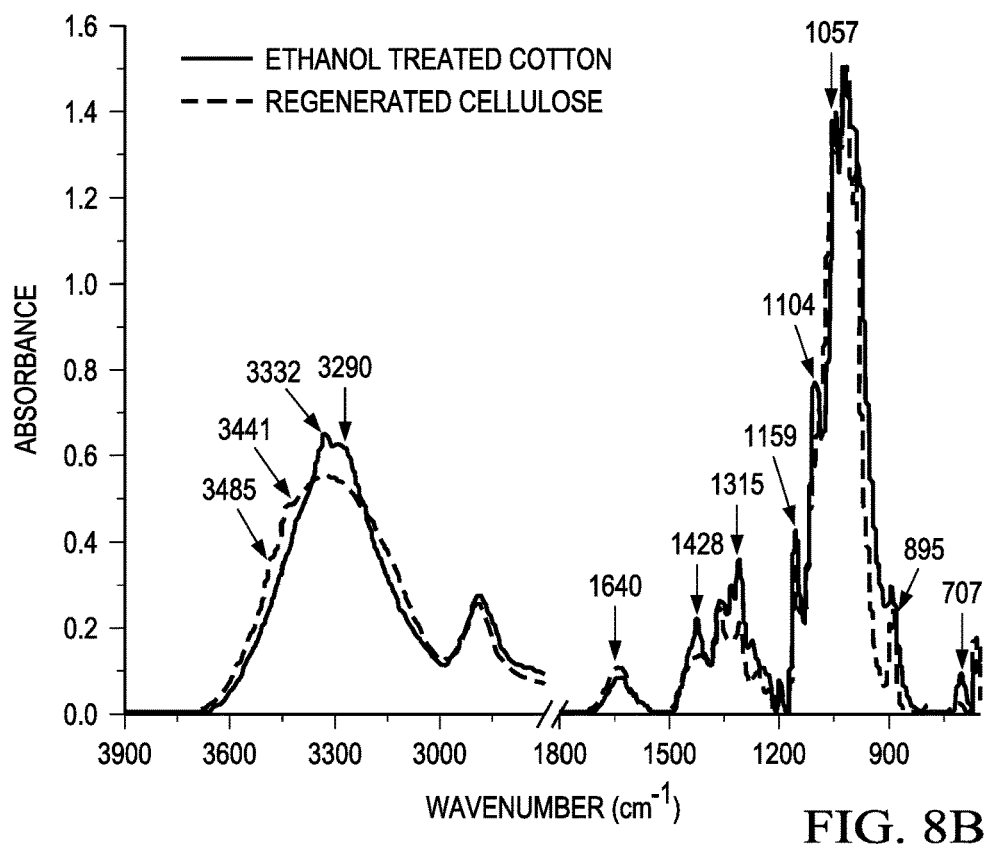

FTIR spectra of cellulose before and after regeneration for samples 6 and 7 are shown in FIGS. 8A and 8B respectively. Similar trends were observed in these spectra as observed for other samples. No new peaks appeared in the regenerated samples, indicating that no chemical reaction occurred during the dissolution and coagulation process of cellulose. In other word, [$C_4C_1$im][(OMe)(H)$PO_2$] is an inert solvent for cellulose. Moreover, the changes in the vibrations at 1428 and 895 $cm^{-1}$ in the regenerated cellulose is due to the transformation of crystalline structure from cellulose $I_β$ to $II_β$.

FIG. 8A shows an FTIR spectra of ethanol-treated ground cotton cellulose and freeze-dried cellulose regenerated after dissolution in [$C_4C_1$im][(OMe)(H)$PO_2$] and 1-methylimidazole. FIG. 8B shows an FTIR spectra of ethanol-treated ground cotton cellulose and freeze-dried cellulose regenerated after dissolution in $[C_4C_1im][(OMe)(H)PO_2]$ and 1-ethylimidazole.

Figure 9A:
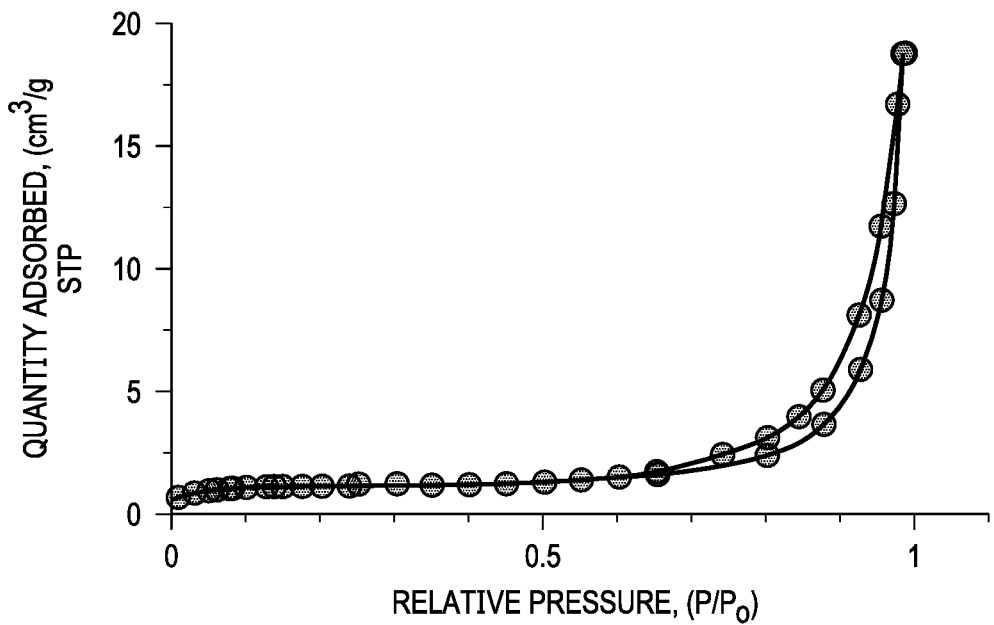
FIGS. 9A and 9B show adsorption-desorption isotherms of regenerated cellulose samples 6 and 7, respectively.
Figure 9B:
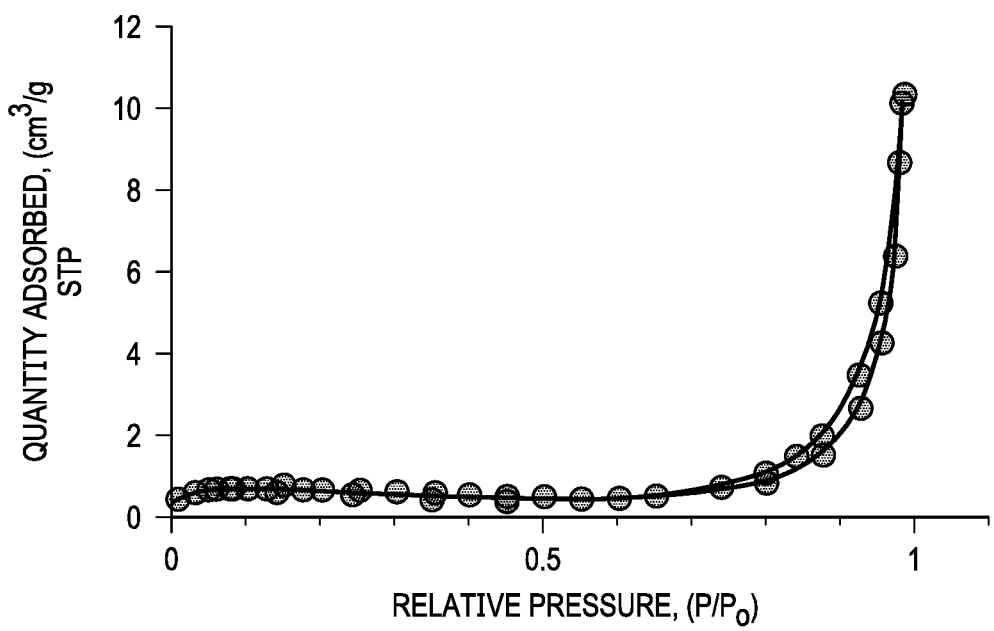

Nitrogen adsorption-desorption isotherms measurements. FIGS. 9A and 9B show nitrogen adsorption-desorption isotherms of regenerated cellulose samples 6 and 7, respectively. Results obtained from BET surface area measurements indicate that BET surface area of sample 6 is more than two times higher than the surface area of sample 7 (sample 6-4.11 m²/g; sample 7-2.19 m²/g). Cumulative surface area and cumulative volume of pores are also remarkably increased in sample 6 as compared to sample 7. Increased porosity and surface area of regenerated cellulose of sample 6 compared to sample 7 indicates easier access and diffusion of IL inside the cellulose network to perform better dissolution [8].

Physicochemical Properties of IL/Co-Solvent Mixtures. Hydrogen bonding basicity as determined by the β value of the anion appears to be an important factor in the interaction between hydroxyl groups of cellulose to weaken the inter- and intra-hydrogen bonds in cellulose chains and to dissolve cellulose. β values of $[C_4C_1im]$ Cl and $[C_4C_1im]$ [HCOO] containing salts are 0.87 and 1.01 respectively [46]. The greater the basicity of anion, the higher the hydrogen-bond acceptor ability, which leads to rapid disruption of the intra- and intermolecular hydrogen bonds in cellulose chains. According to the literature, ILs with slightly less basicity compared to the other IL, have shown better dissolution. For example, with higher β value, $[C_2C_1im][(MeO)(Me)PO_2]$ (β value 1.07) dissolves MCC less effectively than $[C_2C_1im]$ $[(MeO)(H)PO_2]$ (β value 1.00) which suggests that the hydrogen bonding basicity may not be the only parameter to consider. The viscosity of the ILs also plays a key role in dissolving cellulose under mild conditions. According to Fukaya and co-workers study in 2008, $[C_2C_1im][(MeO)(H)PO_2]$ with less β value and lower viscosity dispersed MCC more easily than $[C_2C_1im][(MeO)(Me)PO_2]$ which has higher β value and higher viscosity. [1]

The present inventors also performed conductivity and viscosity studies in the temperature range of 30-90° C. on these solvent systems in order to understand the dissolution behavior of cellulose in these solvent systems.

Measurement of Kamlet-Taft β Parameter of IL/Co-solvent Mixtures. The Kamlet-Taft β parameter is obtained by using the solvatochromic comparison method, which compares the solvent-induced shifts of the absorption bands of two solvatochromatic dyes, 4-nitroaniline (NA) and N,N-diethyl-4-nitroaniline (DENA). NA (99%, Sigma-Aldrich) and DENA (97%, Oakwood Chemical) were used as received. First $1.0 \times 10^{-3}$ M methanol stock solutions of each dye were prepared. An appropriate amount of a dye stock solution was micropipetted into a clean vial. One mL of the IL or equimolar IL/co-solvent mixture was added to the vial. The samples were prepared in an argon-filled glovebox to avoid absorption of water from the air by the samples. The methanol was then carefully removed by vacuum drying at 40° C. for 8 hours. The samples were placed in 1-mm pathlength quartz cuvettes. A Shimadzu UV1800 spectrophotometer was used for the absorption measurements. Using the wavelength maxima $\lambda_{max}(NA)$ and $\lambda_{max}(DENA)$ (in nanometers) of the corresponding dye solutions and Equations 1-3 below, the values of β for the neat IL and IL/co-solvent mixture were determined (Table 2).

$$\beta = \left( \frac{1.035 v_{NA} + 2.64 - v_{DENA}}{2.80} \right) \quad (1)$$

where $$v_{NA} = [\lambda_{max}(NA) \times 10^{-4}]^{-1} \quad (2)$$

$$v_{DENA} = [\lambda_{max}(DENA) \times 10^{-4}]^{-1} \quad (3)$$

TABLE 2

Beta Parameter for Neat IL and IL/Co-solvents Mixtures.

| Solvent | β-parameter |
|---|---|
| IL | 0.961 ± 0.006 |
| IL + 1-methylimidazole | 1.02 ± 0.02 |
| IL + 1-ethylimidazole | 1.04 ± 0.01 |
| IL + 1-butylimidazole | 1.05 ± 0.01 |

From the data obtained, it is evident that the basicity enhances with the presence of co-solvents. As a result, the ability of the anion to interact with inter- and intra-molecular hydrogen bonds in cellulose is also triggered. Clearly, all three co-solvents enhanced the basicity compared to that of neat IL, with the basicity following the order: the IL/1-butylimidazole>IL/1-ethylimdazole>IL/1-methyl imidazole>neat IL.

Conductivity Measurements. The conductivity measurements were performed in order to understand the effect of the mobility of ions on these solvent systems in the temperature range from 20-90° C. The greater the mobility of ions, the greater the conductivity. The conductivities of solvent systems (neat IL and the IL/1-methylimidazole, IL/1-ethylimidazole, and IL/1-butylimiazole) were measured using a YSI 3200 conductivity meter (YSI Instruments, Yellow Springs, Ohio). A fill-type cell (cell constant=1.0 cm$^{-1}$) with a built-in temperature sensor was used. The cell constant was calibrated prior to use with 0.10 and 0.010 mol/Kg aqueous KCl solutions. The measurements were performed in an argon-filled glovebox to avoid moisture contamination. The conductivity was measured from room temperature to 90° C., which is the temperature at which the dissolution studies were performed. As can be seen in the plot of conductivity versus temperature in FIGS. 9A and 9B, the conductivities increase with increasing temperature for samples 6 and 7, respectively. Given that the conductivity is directly related to the mobility of the ions, one can clearly see how the mass transport could be higher in the IL/co-solvent mixtures than the neat IL, which could also explain how cellulose dissolution is facilitated by the addition of the co-solvent. These studies show that the conductivity of the IL/1-ethylimidazole mixture in the presence of cellulose at room temperature is significantly decreased, which could partly be attributed to the interaction of ions with cellulose.

Figure 10:
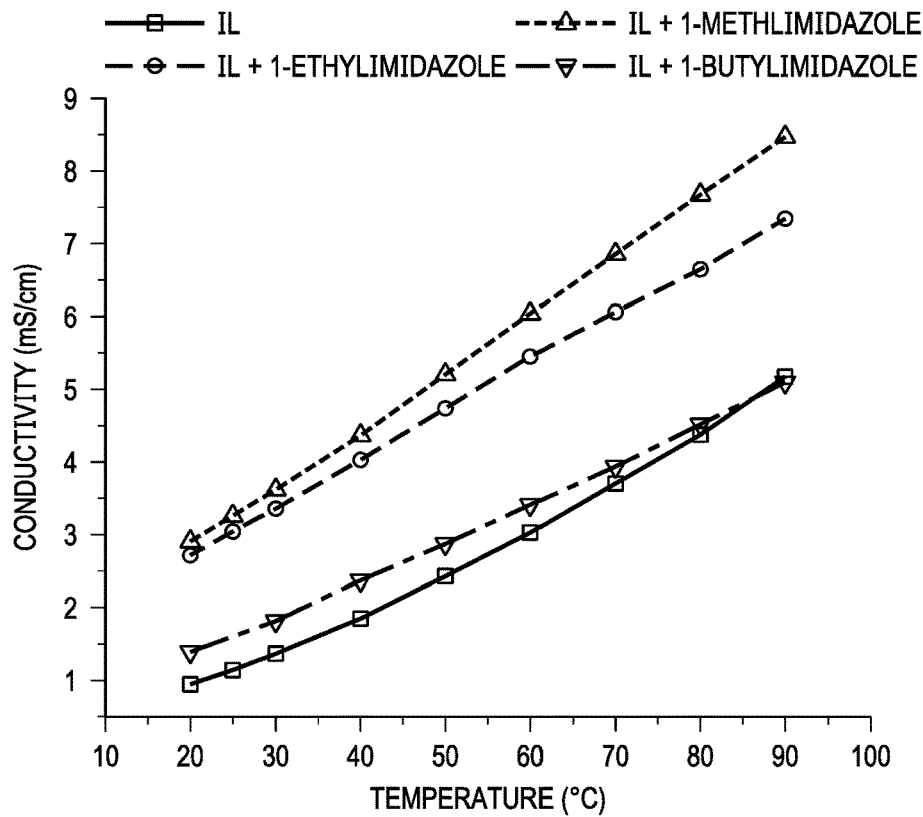
FIG. 10 shows plots of the conductivity versus temperature for neat IL and IL+ co-solvent systems.

As can be seen in FIG. 10, there is a substantial increase in conductivity in going from the neat IL to IL/1-methylimidazole and IL/1-ethylimidazole mixture. The solvent system with 1-butylimidazole as the co-solvent has a lower conductivity compared to the other two mixture systems, but is greater than that of the neat IL. These trends in the conductivity may account for better solubility of cotton cellulose in the solvent systems IL/1-methylimidazole and IL/1-ethylimidazole. Higher conductivity suggests that the mobility of ions in those two systems is higher than neat IL and IL/1-butylimidazole system. The greater the ion mobility, the greater the mass transport of ions, leading to faster dissolution.

Viscosity measurements. Viscosities of the IL and IL/co-solvent mixtures were measured as a function of temperature by use of a TA Instruments AR2000 rotational rheometer with a Couette cell. Measurements were carried out from 303.15 to 363.15 K (0.01 K). The applied shear rates ranged from 100 to 500 s-1. The error in viscosities obtained with this rheometer was estimated to be ±2 mPa·s using the S60 Cannon viscosity standard. The sample volume for the measurement was approximately 10 mL. Using a Couette cell minimizes the exposure of the IL to air compared to other geometries such as cone-plate and parallel-plate. To confirm that moisture in the air has a minimal effect on the viscosity, the viscosity of the IL was measured at a specific temperature once and then again after approximately 1 h, during which time the viscosity was observed to be constant.

Figure 11:
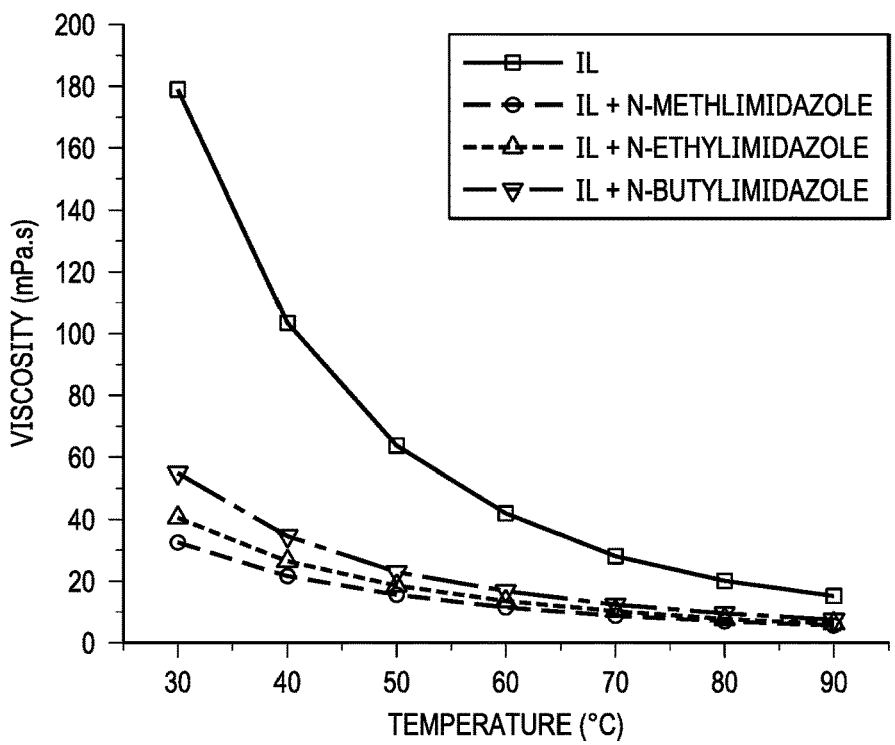
FIG. 11 shows the viscosity vs temperature in neat IL and IL/Co solvent equimolar mixtures.

In the presence of co solvents 1-methyl imidazole, 1-ethyl imidazole and 1-butyl imidazole, the viscosity of the mixtures is significantly lower than the neat ionic liquid. As expected equimolar 1-methylimidazole/IL mixture had the lowest viscosity while 1-ethylimidazole/IL mixture has the next lowest (FIG. 11). The lower the viscosity, the greater the mobility of ions in the solution, leading to faster dissolution.

The presence of 1-methylimidazole also enhances the dissolution of cellulose due to the formation of a hydrogen-bonded complex between the cation and the basic nitrogen atom of methyl imidazole. Cation and imidazole associate to form a complex. This shielding of the cation enables an increase in the free anion concentration in the medium. One can suppose that the aromatic ring of the methyl imidazolium cation in the ion pair can still act as a weak electron acceptor. The cation and anion exists as dissociated ion pairs, where the availability of the anion to form hydrogen bonds with cellulose is enhanced. When the cellulose chains are opened up by the anion, the cation coordinates with 1-methylimidazole and moves into the fibrils, further enhancing dissolution. The acidic proton on $[C_4C_1im]^+$ cation and 1-methylimidazole can be utilized in the formation of hydrogen bonds between cellulose hydroxyl groups, which leads to further dissolution. The degree of shielding of $[C_4C_1im]^+$ cation with 1-butylimidazole is less than with 1-ethylimidazole and 1-methylimidazole. Shielding of the cation enables the anion to move into the cellulose fibrils and cleave the intra and intermolecular hydrogen bonds. For this reason, 1-butylimidazole is a less efficient co-solvent than 1-methylimidazole or 1-ethylimidazole.

Ethanol-treated cotton more readily dissolved in $[C_4C_1im][(OMe)(H)PO_2]$ than untreated cotton. These studies showed that prolonged heating to remove ethanol before dissolution enhances the physical integrity of regenerated cellulose films. The mechanical properties of regenerated films can be utilized in future applications. As co-solvents, 1-methyl imidazole and 1-ethylimidazole were more effective towards cellulose dissolution than 1-butylimidazole. Moreover, dissolution behavior can be rationalized by the basicity, conductivity, and viscosity of the IL/co-solvent mixtures. Using combined method (ethanol-pretreated cotton cellulose in equimolar IL/1-methylimidazole mixtures) reduces the time to less than 15 minutes to achieve complete dissolution. After regeneration, the films that obtained were homogeneous and they had amorphous morphology and crystalline structure $II_β$.

Example 2. Substituent Effects on Cellulose Dissolution in Imidazolium-Based Ionic Liquids The dissolution of cotton cellulose with ILs has been extensively studied. However, the mechanism of cellulose dissolution, especially the role of IL cation in the dissolution process, is not well understood. This example describes a systematic study of the effects of the substituents groups on the cation of imidazolium-based ILs on cellulose dissolution. A series of imidazolium-based ILs with acetate as the anion, 1-hepyl-3-methylimidazolium acetate ($[C_7C_1im][OAc]$), 1-(cyclohexylmethyl)-3-methylimidazolium acetate ($[CyhmC_1im][OAc]$), 1-benzyl-3-methylimidazolium acetate ($[BnzC_1im][OAc]$), 1,3-dibenzylimidazolium acetate ($[(Bnz)_2im][OAc]$), and 1-(2-napthylmethyl)-3-methylimidazolium acetate ($[NapmC_1im][OAc]$), were synthesized. In each dissolution study, 5% (w/w) ground cotton fiber was dissolved in the ILs below 100° C. The skilled artisan will understand that the present procedure will work for any type of cellulose, be it plant or microbial. The progress of the dissolution was monitored periodically with a polarized light microscope. This study revealed that $[BnzC_1im][OAc]$ dissolved cotton cellulose more efficiently than the other four ILs. The results are discussed within the context of previous published molecular dynamic simulations on cellulose dissolution in ILs. For the five ILs that were investigated, it was found that the effect of the cation can be rationalized on the basis of both the size and shape of the cation. In addition to the dissolution, cellulose was regenerated, and characterized by Fourier transform infrared (FTIR) spectroscopy.

The present inventors determined the effect of different substituents on the imidazolium ring of the cation of the ILs in cellulose dissolution. In this study, five ILs with a fixed acetate $[OAc]^-$ anion and a 1-R-3-methylimidazolium cation functionalized by various R groups with R=n-heptyl ($C_7$), cyclohexylmethyl (Cyhm), 2-naphthylmethyl (Napm) and benzyl (Bnz) were synthesized, as well the dibenzyl cation $[(Bnz)_2im]^+$ and were used in cotton cellulose dissolution (see Table 2). The aforementioned ILs allowed the study of the effect of the substituents on the N atoms of the imidazolium cations. In particular, the inventors were able to study how the dissolution is affected by having cyclic alkyl, long alkyl chain and planar aromatic substituents. The results observed in the cellulose in these five ILs are discussed within the context of the MD simulation results.

TABLE 3

Structures and Formulas of Imidazolium-Based Cations

| cation | cation structure | vdW Volume$^a$ (Å$^3$) | abbreviation | formula |
| --- | --- | --- | --- | --- |
| 1-hepyl-3-methylimidazolium | 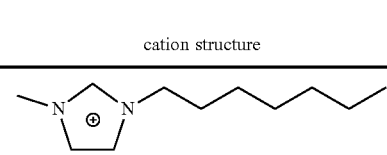 | 261.3 | $[C_7C_1im]^+$ | $C_{11}H_{21}N_2^+$ |

TABLE 3-continued

Structures and Formulas of Imidazolium-Based Cations

| cation | cation structure | vdW Volume[a] (Å$^3$) | abbreviation | formula |
|---|---|---|---|---|
| 1-(cyclohexylmethyl)-3-methylimidazolium | | 232.0 | [CyhmC$_1$im]$^+$ | C$_{11}$H$_{19}$N$_2^+$ |
| 1-benzyl-3-methylimidazolium | | 222.9 | [BnzC$_1$im]$^+$ | C$_{11}$H$_{13}$N$_2^+$ |
| 1,3-dibenzylimidazolium | | 303.6 | [(Bnz)$_2$im]$^+$ | C$_{17}$H$_{17}$N$_2^+$ |
| 1-(2-napthylmethyl)-3-methylimidazolium | | 269.3 | [NapmC$_1$im]$^+$ | C$_{15}$H$_{15}$N$_2^+$ |

[a]Van der Waals volume from AM1 quantum calculations using Spartan 10 (Wavefunction, Inc).

Materials. 1-Methylimidazole (Sigma, 98.9%), 2-(bromomethyl)naphthalene (Sigma, 96%), (bromomethyl)cyclohexane (Sigma, 99%), benzyl bromide (Sigma, 98%) 1-bromoheptane (Sigma, 99%), 1-methylimidazole (Sigma, 99%), Amberlite IRA-400 chloride resin (Sigma) were used without further purification. Dichloromethane (DCM) and acetonitrile were separately distilled over CaH$_2$ under nitrogen and diethyl ether was distilled over Na/benzophenone. A 1N NaOH solution was prepared by dissolving 40 g of NaOH (Fisher) in 1 L of deionized water for anion exchange with chloride. For the gravitational column chromatography, Celite (Fisher), sand (Macros), aluminum axide (60 A, activated, basic, 50-200 micron, Acros) and glass wool were used. Acetic acid (Sigma) was used for neutralization. All ILs were dried in a vacuum oven at 50° C. for 96 h. After drying, the water contents (less than 400 ppm, measured by Karl Fisher titration, (Karl Fisher METTLER TOLEDO C20 coulometric KF titrator)), halogen ion (undetectable as measured by AgNO$_3$ precipitation), and other impurities (undetectable as measured by NMR with JEOL 400 MHz spectrometer) were determined. $^1$H and $^{13}$C NMR, spectra were recorded on a JEOL ECS 400 MHz spectrometer. For $^1$H NMR spectra, tetramethylsilane (TMS, δ=0.00) or the residual protic solvent peak (for (CD$_3$)$_2$CO, δ=2.05, DMSO-d$_6$, δ=2.50), for $^{13}$C NMR spectra tetramethylsilane (TMS, δ=0.00) or the residual protic solvent peak (for (CD$_3$)$_2$CO, δ=29.84, DMSO-d$_6$, δ=39.50) served as a shift reference. Coupling constants, J, are reported in hertz. All reaction vessels were flame-dried under vacuum and filled with nitrogen prior to use. All reactions were performed under a nitrogen atmosphere as a routine practice, not as an essential requirement.

Synthesis of ionic liquids. 1-(2-methylcyclohexyl)-3-methylimidazolium acetate ([CyhmC$_1$im][OAc]) was prepared as follows. 1-(2-methylcyclohexyl)-3-methylimidazolium bromide ([CyhmC$_1$im][Br]) was dissolved in deionized water, and the resulting solution was passed through a column filled with anion exchange resin (amberlite IRA-400) and flushed with 1N NaOH to yield an aqueous solution of 1(2-methylcyclohexyl)-3-methylimidazolium hydroxide ([CyhmC$_1$im][OH]). Acetic acid aqueous solution was added dropwise to the aqueous [CyhmC$_1$im][OH] solution and the resulting solution was stirred overnight at room temperature. After removal of water by evaporation, the residual liquid was repeatedly washed with excess amounts of anhydrous diethyl ether. The resulting liquid was fully mixed with DCM, followed by the addition of activated carbon and the mixture was stirred for 3 days. The mixture was passed through a gravitational column filled with active alumina, celite and sand. DCM was removed by rotary evaporation and the resulting liquid was dried in vacuo at room temperature, yielding [CyhmC$_1$im][OAc] as a pale yellow liquid. [C$_7$C$_1$im][OAc], [BnzC$_1$im][OAc], [NapmC$_1$im][OAc] and [(Bnz)$_2$im][OAc] were prepared using similar procedures with the corresponding IL bromides. (See details of the synthesis of the IL acetates and bromides below) The chemical structures of synthesized ILs were confirmed by $^1$H and $^{13}$C NMR spectra (see details below).

Preparation of cotton fibers for dissolution. Carded cotton fibers were received from the Fiber and Biopolymer Research Institute, Texas Tech University. The fibers were scoured, bleached, air-dried, and ground by a Wiley mill to pass through a 20 mesh screen. They were dried at 105° C. overnight in a laboratory oven.

Dissolution of ground cotton fibers in ILs. [(Bnz)$_2$im][OAc] and [NapmC$_1$im][OAc] were heated at 85° C. in a laboratory oven until they became fluid enough to allow for stirring. The ILs and ground cotton fiber (5 wt. %) were measured separately and ground cotton fiber samples were slowly added into the ILs. The dispersions were heated to 90-100° C. with several 3-5 sec pulses in a microwave oven. The mixtures were placed in a 90° C. laboratory oven and continuously heated for 24 h.

Polarized light microscopy (PLM). Representative samples of the solution were taken in 4 different time intervals (before and after the solutions were microwaved, and after 4 and 24 h at 90° C.). The mixtures were stirred well before the samples were collected. The dissolution processes in different ILs were observed by a Nikon ECLIPSE LV 100 polarizing light microscope with NIS-Elements imaging platform. The images were recorded at room temperature under ×10 magnification.

Regeneration of cellulose from the mixtures. Each cotton-IL solution was poured onto a glass slide and covered with another glass slide. They were allowed to spread uniformly by gentle pressing the glass slides. The glass slides that contained cotton-IL were kept in a glass jar. Deionized water was poured into the glass slides to regenerate cellulose from the solutions. The ILs were rinsed away from the regenerated cellulose by changing deionized water for 3-4 days.

Freeze drying the regenerated cellulose. Regenerated cellulose from different ILs were kept at −4° C. for 2 h and dried using a Labconco FreeZone (4.5 Liter Cascade Benchtop Freeze Dry System) at −102° C. and 0.05 mbar for 3 days.

Characterization of the regenerated cellulose. Scanning electron microscopy (SEM). Scanning electron micrographs of regenerated cellulose samples were recorded using a Hitachi TM-1000 tabletop environmental scanning electron microscope at an accelerating voltage of 15 kV. Regenerated cellulose samples were mounted on carbon discs without any coating prior to obtaining the images.

Fourier transform infrared spectroscopy (FTIR). Freeze-dried, regenerated cellulose samples and hot dried ground cotton fibers were conditioned in the laboratory at 21±1° C. at 65±2% relative humidity for 2 days before FTIR analysis. FTIR spectra of all regenerated samples were collected using a PerkinElmer Spectrum 400 FTIR spectrometer equipped with a universal attenuated total reflectance (UATR) accessory. The ZnSe-diamond crystal was cleaned with Milli-Q water and ethanol and a background scan of the clean crystal was performed prior to scanning the samples. The samples were placed on the Zn-Diamond crystal without further sample preparation. Constant pressure was applied to each sample by the "pressure arm" of the instrument, which was monitored using Perkin-Elmer software to minimize the loss of intensity of IR beam. The spectra were collected in the mid-IR range from 650-4000 $cm^{-1}$ at a resolution of 4 $cm^{-1}$ with 32 co-added scans. Then they were subjected to baseline correction and normalization using the Perkin-Elmer software.

Figures 12A, 12T:
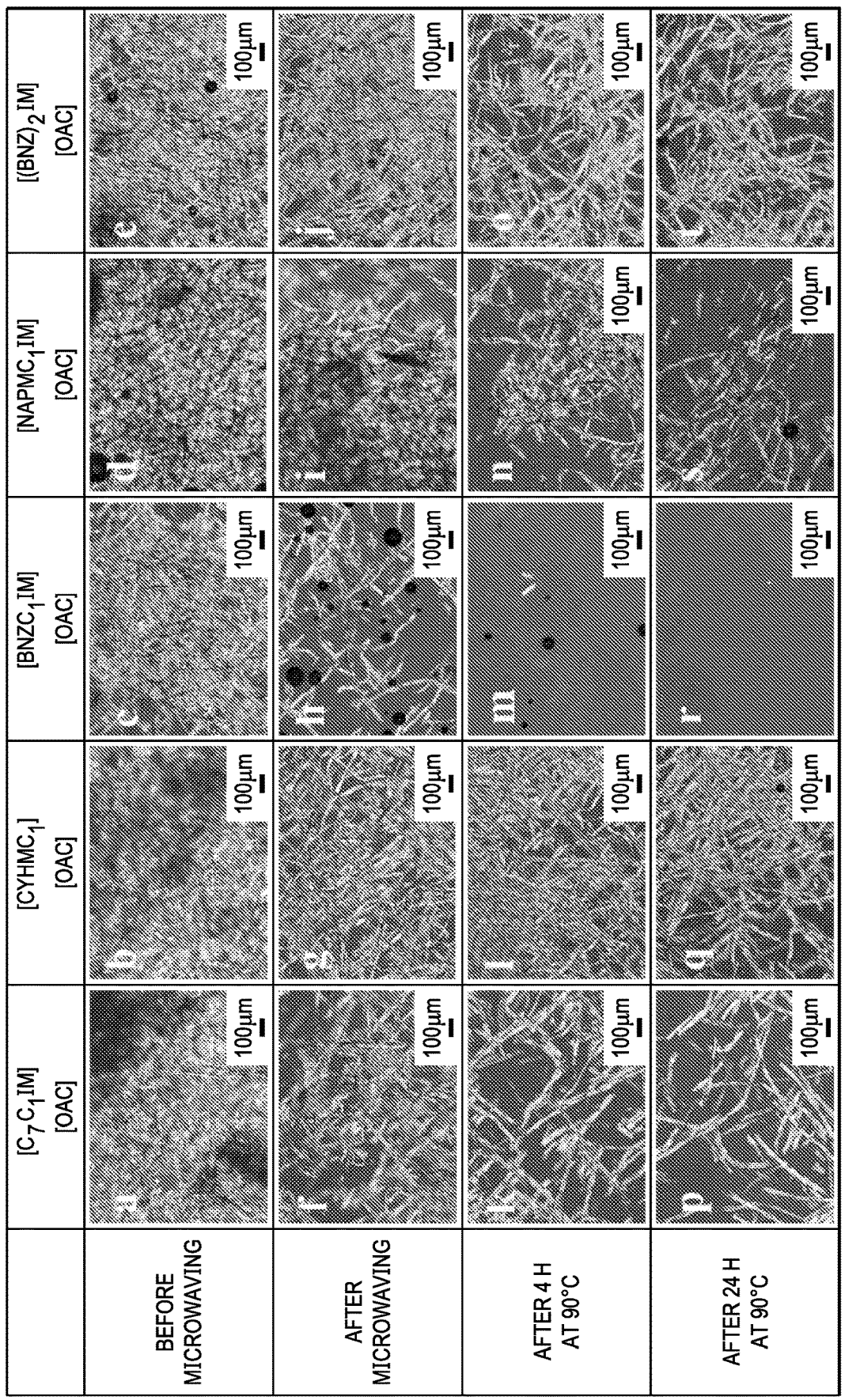
FIGS. 12A to 12T show PLM images of cotton cellulose in ILs at different stages of dissolution. See Table 3 for abbreviations of the ILs.

Polarized light microscopy of cellulose dissolution. FIGS. 12A to 12T show PLM images of the state of the 5% (w/w) mixtures for the five ILs at different stages of cellulose dissolution: before microwaving (FIG. 12A-FIG. 12E), after microwaving (FIG. 12F-FIG. 12J), after 4 h of heating at 90° C. (FIG. 12K-FIG. 12O); and after 24 h of heating at 90° C. (FIG. 12P-FIG. 12T). Because of the extensive crystalline structure of native cellulose, the PLM is able to show the state of cellulose fiber-IL mixtures during dissolution. The PLM images of the mixtures before microwaving (FIG. 12A-FIG. 12E) provide a reference from which to compare the other stages of dissolution. As can be seen in the PLMs images before microwaving (FIG. 12A-FIG. 12E) and after microwaving (FIG. 12F-FIG. 12J), the heating that occurs during microwaving causes dissolution to occur to varying extent depending upon the IL. In the case of [$C_7C_1$im][OAc], [$CyhmC_1$im][OAc] and [$(Bnz)_2$im][OAc], [$NapmC_1$im][OAc] relatively low dissolution has occurred after microwaving. In contrast, there is noticeable cellulose dissolution in [$BnzC_1$im][OAc] after microwaving as evidenced by regions showing the absence of crystalline cellulose. The PLM images show that stirring at 90° C. for 4 h led to complete dissolution in [$BnzC_1$im][OAc] (FIG. 4m) and varying levels of dissolution in the other four ILs (FIG. 12K, FIG. 12L, FIG. 12N, and FIG. 12O). Comparing the images taken after 4 and 24 h at 90° C. to images before microwaving, it was found that the degree to which dissolution has occurred follows the trend [$BnzC_1$im][OAc]>> [$NapmC_1$im][OAc]>[$C_7C_1$im][OAc]>[$(Bnz)_2$im][OAc]> [$CyhmC_1$im][OAc].

Figure 13A:
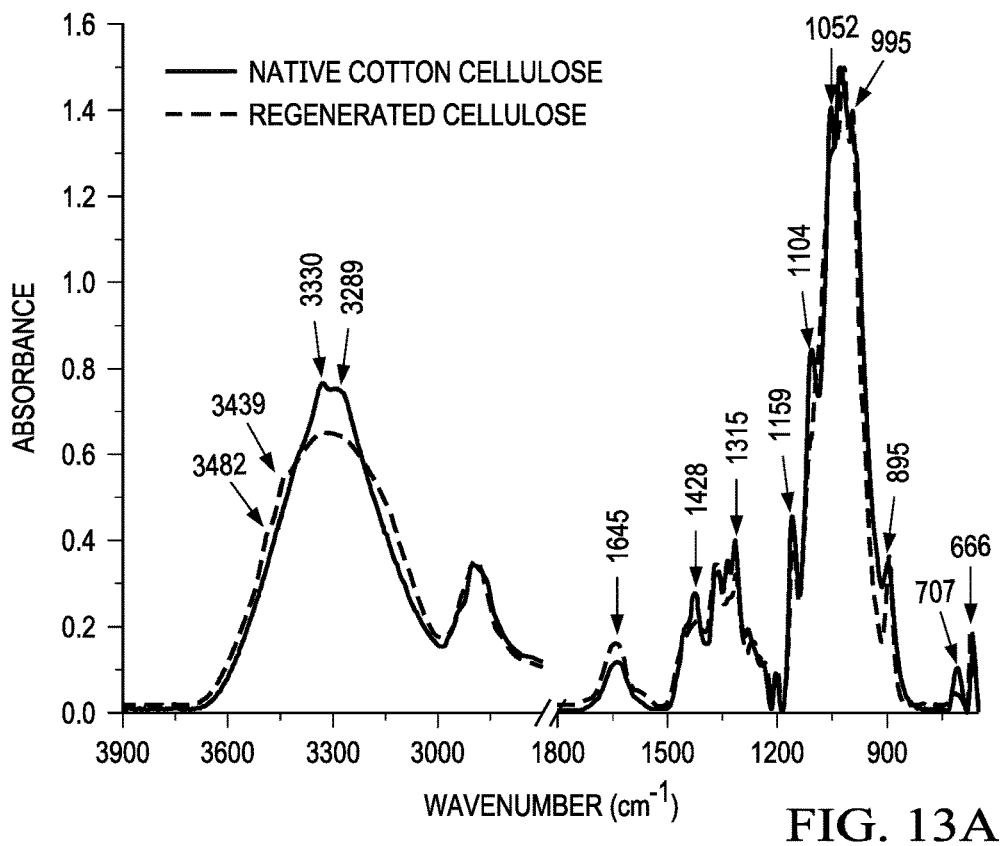
FIG. 13A shows FTIR spectra of ground cotton cellulose and freeze-dried cellulose regenerated after dissolution in [BnzC$_1$im][OAc].
Figure 13B:
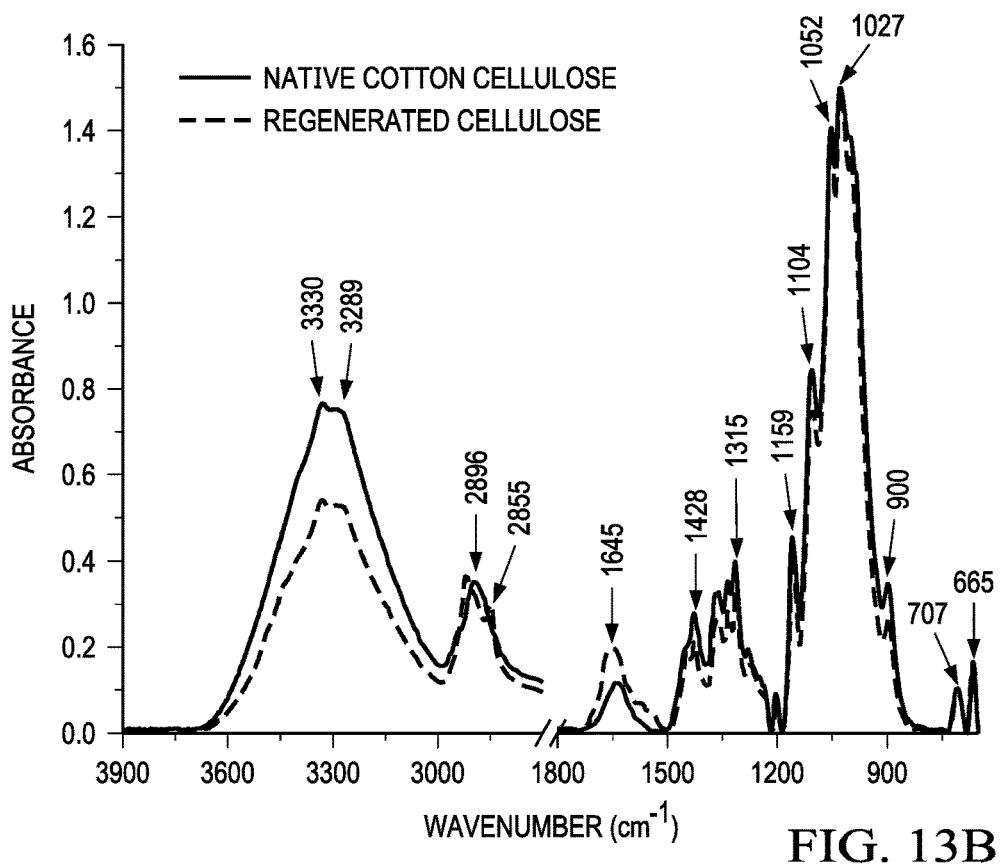
FIG. 13B shows FTIR spectra of ground cotton cellulose and freeze-dried cellulose regenerated after dissolution in [CyhmC$_1$im][OAc].

Structure and morphology of regenerated cellulose. FTIR spectra. FIG. 13A shows FTIR spectra of ground cotton cellulose and freeze-dried cellulose regenerated after dissolution in [$BnzC_1$im][OAc]. FIG. 13B shows FTIR spectra of ground cotton cellulose and freeze-dried cellulose regenerated after dissolution in [$CyhmC_1$im][OAc]. The FTIR spectra of the regenerated cellulose prepared by dissolving cotton in [$BnzC_1$im][OAc] and [$CyhmC_1$][OAc] are shown in FIG. 13A and FIG. 13B respectively (See the details below for other FTIR spectra of regenerated cellulose from [$C_7C_1$im][OAc], [$NapmC_1$im][OAc] and [$(Bnz)_2$im][OAc]). The FTIR spectrum of native cellulose is quite similar to that of regenerated cellulose in all the ILs, suggesting that ILs did not affect the chemical structure of cotton cellulose and regenerated cellulose.

However, the FTIR spectrum of regenerated cellulose after dissolution in [$BnzC_1$im][OAc] exhibits significant changes in its vibrations at 3482, 3439, 3330, 3289, 1645, 1428, 1315, 1159, 1104, 1052, 995, 895, 710 and 666 $cm^{-1}$ respectively as compared to the spectrum of the starting material, cotton cellulose. These data are consistent with the values reported in the literature indicating that cellulose in [$BnzC_1$im][OAc] is in the crystalline form II whereas native cotton cellulose is in the crystalline form $I_\beta$ (Abidi et al. 2014; Abidi et al. 2008; Dassanayake et al. 2016; Ilharco et al. 1997; Lan et al. 2011; Oh et al. 2005a; Oh et al. 2005b; Salmen and Bergstrom 2009; Schwanninger et al. 2004; Zhang et al. 2005).

For comparison, regenerated cellulose in least effective IL in the study, [$CyhmC_1$im][OAc] was adopted for the discussion. It was noted that the regenerated cellulose after dissolution in [$CyhmC_1$im][OAc] also showed FTIR vibrations similar to native cotton cellulose. This shows that the regenerated cellulose after dissolution in [$CyhmC_1$im][OAc] is also structurally similar to native cotton cellulose and it is in the crystalline form $I_\beta$. Similar trends were observed in the regenerated cellulose samples after dissolution in the ILs [$C_7C_1$im][OAc], [$NapmC_1$im][OAc] and [$(Bnz)_2$im][OAc]. New peaks in the spectra of cellulose regenerated after dissolution in [$C_7C_1$im][OAc] and [$NapmC_1$im][OAc] are attributed to the IL that remained after rinsing the regenerated cellulose with deionized water (See details below for FTIR spectra of neat [$C_7C_1$im][OAc] and [$NapmC_1$im][OAc]).

Figure 14A:
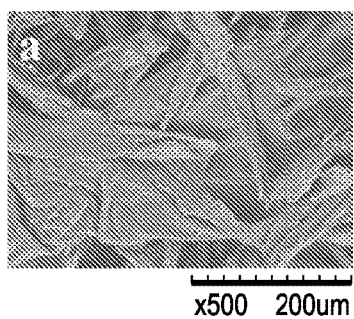
FIGS. 14A to 14E are scanning electron micrographs of the topography of regenerated cellulose films.
Figure 14B:
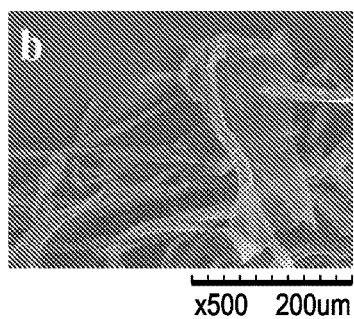
Figure 14C:
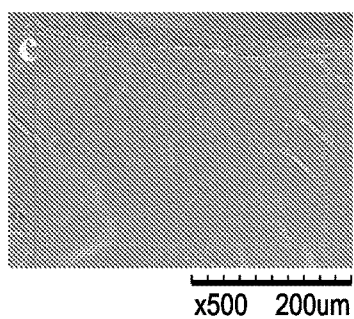
Figure 14D:
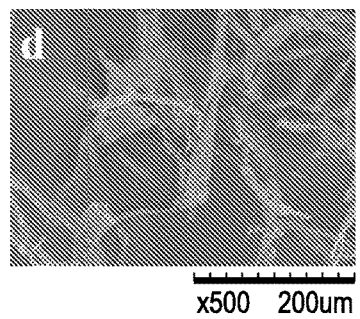
Figure 14E:
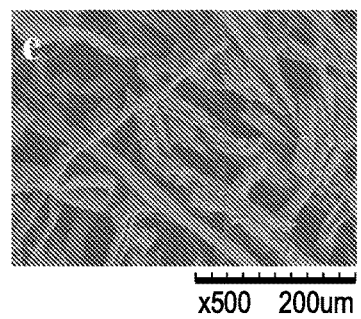

Scanning electron micrographs. Surface morphologies of the regenerated films were investigated using scanning electron microscopy (SEM). Depicted in FIGS. 14A to 14E are SEM images of regenerated cotton cellulose after dissolution in [$C_7C_1$im][OAc], [$CyhmC_1$im][OAc], [$BnzC_1$im] [OAc], [$NapmC_1$im][OAc] and [$(Bnz)_2$im][OAc] respectively. Each SEM image was captured under an ×500 objective magnification. SEM micrographs in FIGS. 14A and 14B show that film formed from cellulose regenerated after dissolution in [$C_7C_1$im][OAc] and [$CyhmC_1$im][OAc], which mainly includes undissolved fibers, thus indicating an incomplete dissolution. These images show that the structures of film to be characterized by undissolved cotton fibers embedded and surrounded by partially dissolved cellulose fibers. In contrast, FIG. 14C shows that cellulose regenerated after dissolution in [$BnzC_1$im][OAc] forms a uniform film. The absence of un-dissolved fibers in the film is consistent with the PLM images recorded at 24 h (FIG. 12R)

that showed complete dissolution of the cotton cellulose. Additionally, the free surface and the fracture surface of the regenerated film shows uniformity across the whole surface of the film. This uniformity is an indicator of a dense texture in the cellulose. Similarly, FIGS. 14D and 14E indicated the presence of un-dissolved fibers in the film which is consistent with incomplete dissolution of cotton cellulose in both [NapmC$_1$im][OAc] and [(Bnz)$_2$im][OAc] respectively. The SEM images also indicate that the films have homogeneous non-porous structures.

MD simulations performed by Li et al. (2015) and Rabideau et al. (2014) differ in the nature of the cation-cellulose interactions, but both confirm the importance of hydrogen bonding of the anion to the hydroxyl groups in cellulose in the dissolution mechanism. According to Li et al. and Rabideau et al., the breakup is faster for ILs with [OAc]$^-$ than for ILs with [Cl]$^-$, not only because [OAc]$^-$ is a better hydrogen-bond acceptor than [Cl] but also because the [OAc]$^-$ anion is larger than the [Cl]$^-$ anion. Moreover, because of Coulombic attraction, the cation is drawn by the anion into the interior of the cellulose fiber, causing the strands to separate from the main bundle. Clearly, the ability of the cation to intercalate between the strands and to cause the strands to separate should be dependent on the size and possibly the shape of the cation. The results of the current study confirm this. For example, cation size is a plausible reason for dissolution being more effective in [BnzC$_1$im][OAc] than in [(Bnz)$_2$im][OAc]. The [(Bnz)$_2$im]$^+$ cation with two phenyl groups will have more difficulty intercalating between the strands than the [BnzC$_1$im]$^+$ cation with only one phenyl group.

By way of explanation, and in no way a limitation of the present invention, the size effect can also be invoked when explaining why cotton cellulose dissolution is more effective in [BnzC$_1$im][OAc] than in [NapmC$_1$im][OAc]. One could also explain cellulose dissolution being more effective in [NapmC$_1$im][OAc] than in [(Bnz)$_2$im][OAc] because of a size effect, with the [NapmC$_1$im]$^+$ cation being 11% smaller than [(Bnz)$_2$im]$^+$ cation based on the values of van der Waals volume ($V_{vd}w$) (Table 3). However, the PLM images show a lot fewer fibers present after 24 h in [NapmC$_1$im][OAc] than in [(Bnz)$_2$im][OAc] (FIGS. 12S and 12T), which suggests that other factors may be playing a role. In the case of [(Bnz)$_2$im][OAc], space-filling models show the phenyl groups being in a twisted orientation, which causes the rings to lie in two different planes. In contrast, in the case of [NapmC$_1$im][OAc], one can think of the planar naphthyl group as being formed by the fusion of two phenyl rings. The planarity of the naphthyl group allows the cation to slip more easily between the cellulose strands. Thus, factoring the shape effect (twisted versus planar) in addition to the size, one could explain the considerably greater ability for [NapmC$_1$im][OAc] to dissolve cotton cellulose than [(Bnz)$_2$im][OAc].

In the case of dissolution of cellulose in [C$_7$C$_1$im][OAc] as compared to cellulose dissolution in [BnzC$_1$im][OAc], the difference can be attributed to a size effect, given that the [C$_7$C$_1$im]$^+$ cation is 17% larger than the [BnzC$_1$im]$^+$ cation. However, [C$_7$C$_1$im][OAc] seems be an anomaly in that the [C$_7$C$_1$im]$^+$ cation being 3% smaller than the [NapmC$_1$im]$^+$ cation one would have predicted cotton cellulose dissolution to be more effective in [C$_7$C$_1$im][OAc] than in [NapmC$_1$im][OAc], contrary to the actual results. However, the 3% size difference may not be great enough to explain the difference in the abilities of these two ILs to dissolve cellulose. This again suggests, but is not a limitation of the present invention, that other factors must be playing a role in causing the difference in cellulose dissolution between these two ILs. One possibility is that the heptyl group has more conformational freedom compared to the naphthyl group (18 conformers in the case of [C$_7$C$_1$im]$^+$ versus 4 conformers in the case of [NapmC$_1$im]$^+$ as determined by AM1 calculations). This conformational freedom could impede intercalation of the cation between strands in the fiber bundle. In contrast, the naphthyl group being rigid because of its planarity can more easily slide between the strands in the cotton fiber.

These studies show that of the five ILs, [CyhmC$_1$im][OAc] is the least effective in dissolving cotton cellulose as evidenced by PLM images that show no fibers in the case of dissolution with [BnzC$_1$im][OAc] but large amounts of undissolved fibers in case of dissolution with [CyhmC$_1$im][OAc], even after 24 h (FIG. 12I and FIG. 12m). Given that the [CyhmC$_1$im]$^+$ cation is only 4% larger than the [BnzC$_1$im]$^+$ cation, based the values of $V_{vdW}$ (Table 3), the difference in the ability of these two ILs to dissolve cellulose cannot be due just to a size effect. The difference could be due to a shape effect in that the planarity of the phenyl groups in the [BnzC$_1$im]$^+$ and [(Bnz)$_2$im]$^+$ cations and the planarity of the naphthyl group in the [NapmC$_1$im]$^+$ cation helps these cations to intercalate between cellulose strands of the cotton, thus promoting pealing of strands from the fiber. In contrast, the bulkiness and larger size of the cyclohexyl group compared to the phenyl group introduces steric effects on the cation that minimize the penetration of the cation between the strands of cellulose. Unlike the phenyl group, the cyclohexyl group is not planar due to the fact that it can either be in the boat or chair configuration.

This is the first study that provides a plausible molecular-level explanation that is based on MD simulations for the role of the cation in the dissolution of cotton cellulose in ILs. [CyhmC$_1$im][OAc] and [(Bnz)$_2$im][OAc] performed poorly in the dissolution of cotton cellulose. On the other hand, [BnzC$_1$im][OAc] showed a significant capacity to dissolve cotton cellulose and was the most effective of the five ILs in this study. The MD simulations indicate that the ability of the cation to intercalate between the strands and to cause the strands to separate should be dependent on the size and possibly the shape of the cation. Indeed, increasing the size of the cation has an adverse effect on cotton cellulose dissolution (e.g., [BnzC$_1$im][OAc] versus [(Bnz)$_2$im][OAc]). The present inventors also determined that shape plays a role in that the bulkiness of the cation (e.g., [CyhmC$_1$im][OAc]) has an adverse effect on cotton cellulose dissolution, whereas the planarity of the cation (e.g., [BnzC$_1$im][OAc]) seems to have a positive effect on cotton cellulose dissolution. In the case of [NapmC$_1$im][OAc] versus [(Bnz)$_2$im][OAc], [(Bnz)$_2$im][OAc] is less effective in dissolving cotton cellulose than [NapmC$_1$im][OAc], not only because the [(Bnz)$_2$im]$^+$ cation is 11% larger in size than [NapmC$_1$im]$^+$ cation, but because of the twisted configuration of the phenyl groups in [(Bnz)$_2$im]$^+$ as opposed to the planarity of the naphthyl group in [NapmC$_1$im]$^+$.

Synthesis of Ionic Liquids. 1,3-dibenzylimidazolium bromide. A 250-mL two-neck Schlenk flask under nitrogen connected to a condenser was placed in an ice bath and charged with 75 mL of freshly distilled THF. After stirring the THF in the ice-water bath for 15 min to lower the temperature, NaH (95%) (2.11 g, 83.34 mmol) was added to the THF and the mixture stirred for 1 h. Imidazole (5.67 g, 83.34 mmol) was dissolved in 50 mL of freshly distilled THF. The imidazole-THF solution was then added to the NaH-THF solution via an addition funnel over 43 min at 1.17 mL/min. After the completion of the addition, the ice-water bath was removed and the reaction mixture was stirred for 15 min to reach room temperature. Benzyl bromide (20.80 mL, 175 mmol) was next added over 55 min at 0.34 mL/min through an addition funnel. After completion of the addition, the reaction mixture was left for 12 h under constant stirring at room temperature while a light-yellow slurry was formed. After running the reaction for 12 h, the reaction mixture was taken off the condenser and filtered via a filtration funnel (with a frit and approximately 2-3 cm Celite 545). The filtrate was transferred to a 250-mL one-neck flask and evaporated in vacuo. The residue from the evaporation was washed with 50 mL of acetonitrile and hexanes (1:3 v/v) three times to remove the excess of benzyl bromide. The IL was concentrated in vacuo using a rotary evaporator. Activated carbon (3 g) and 75 mL of acetonitrile were added to the residue, which was then stirred for 72 h. The black slurry was removed from the stir plate and filtered through a gravitational column packed with glass wool, 10 cm of aluminum oxide (activated, basic, 50-200 micron), 5 cm of Celite 545. The removal of the acetonitrile under reduced pressure afforded the title compound as a colorless, viscous liquid at room temperature. The final product, after being left on the pump solidified overtime. Yield 87%. $^1$H NMR and $^{13}$C NMR were used to characterize the compound.

1-benzyl-3-methylimidazolium bromide. A 250-mL two-neck Schlenk flask equipped with a magnetic stir bar was charged under nitrogen with 50 mL of acetonitrile followed by the addition of 1-methylimidazole (6.30 mL, 79.01 mmol) and benzyl bromide (99%) (9.97 mL, 82.96 mmol) via 10-mL syringes. The reaction mixture was stirred at room temperature overnight. After reaction went to completion (progress was monitored by $^1$H NMR), the reaction flask was removed from the condenser and the crude product washed with 60 mL of hexanes three times. The isolated crude product was dried under vacuum and was dissolved in 60 mL of $CH_2Cl_2$. Approximately 2 to 3 g of activated carbon was added to this solution, which was then stirred overnight. The black slurry was removed from the stir plate and then filtered through a gravitational column that was packed with glass wool, 10 cm of aluminum oxide (activated, basic, 50-200 micron), 5 cm of Celite 545. The excess solvent was removed using a rotary evaporator. The sample was dried under vacuum and title compound isolated (Yield 91%). The pure compound left under vacuum solidified over time. $^1$H NMR and $^{13}$C NMR were used to characterize the compound.

1-heptyl-3-methylimidazolium bromide. A 250-mL two-neck Schlenk flask connected to a condenser equipped with a magnetic stir bar was charged under nitrogen with 9.15 mL of 1-methylimidazole (115 mmol) and 19.0 mL of 1-bromoheptane (120 mmol) and then placed in an oil bath at a temperature of 60° C. The reaction mixture was stirred until the starting material was consumed. The reaction was taken off the condenser and washed with 60 mL of hexanes three times and left to stir in hexaneat room temperature overnight. The mixture was taken off the stir plate and the upper hexane layer was decanted. The residue was dried in vacuo and approximately 2 to 3 g of activated carbon and 60 mL of $CH_2Cl_2$ were added and the mixture was stirred overnight. The black slurry was taken off the stir plate and filtered through a gravitational column that was packed with glass wool, 7 cm of aluminum oxide (activated, basic, 50-200 micron), 3 cm of Celite 545. The solvent was removed by using a rotary evaporator and the product was isolated as a colorless liquid (Yield 92%). $^1$H NMR and $^{13}$C NMR were used to characterize the compound.

1-(2-naphthylmethyl)-3-methylimidazolium bromide. A 250 mL two-neck Schlenk flask was connected to a condenser under $N_2$, placed in an oil bath at a temperature of 45° C., and charged with 2-(bromomethyl)naphthalene (5.32 g, 24.0 mmol, 95%) and 50 mL of acetonitrile to dissolve the solid. This was followed by the addition of 1-methylimidazole (1.83 mL, 23.0 mmol) through a funnel. The reaction mixture was stirred overnight at 45° C. The reaction mixture was taken off the condenser and then was washed with 50 mL of hexanes two times. After washing with hexanes, the crude product was isolated by removing the excess solvent using a rotary evaporator. The residue was completely dried under the vacuum. To the crude product, 75 mL of $CH_2Cl_2$ and approximately 2 to 3 g of activated carbon were added. The black slurry was then stirred overnight. The black slurry was taken off the stir plate and filtered through a gravitational column that was packed with glass wool, 7 cm of aluminum oxide (activated, basic, 50-200 micron), 3 cm of Celite 545. The solvent was removed and pure material was dried under vacuum. The title compound isolated as a viscous liquid, which solidified over the time (Yield 92%). $^1$H NMR and $^{13}$C NMR were used to characterize the compound.

1-(cyclohexylmethyl)-3-methylimidazolium bromide. A 250 mL two-neck flask was placed in an oil bath at 50° C. The flask was connected through a condenser to a $N_2$ purge line. 1-methylimidazole (6.46 mL, 81.02 mmol) and (bromomethyl)-cyclohexane (11.99 mL, 85.07 mmol) were added to the flask via 10-mL syringes. The reaction mixture was stirred at 50° C. until all the 1-methylimidazole was completely consumed. The reaction was taken off the condenser and washed with 60 mL of hexanes three times. The residue was isolated by removing the excess solvent and dried in vacuo. To the crude product approximately 2 to 3 g of activated carbon and 60 mL of $CH_2Cl_2$ were added and the mixture stirred overnight. The black slurry was taken off the stir plate and filtered through a gravitational column that was packed with glass wool, 10 cm of aluminum oxide (activated, basic, 50-200 micron), and 5 cm of Celite 545. The product was isolated by removing the solvent using a rotary evaporator and drying under the vacuum (Yield 88%). $^1$H NMR and $^{13}$C NMR were used to characterize the compound.

Note: 1-heptyl-3-methylimidazolium acetate ([$C_7C_1$im][OAc]), 1-(cyclohexylmethyl)-3-methylimidazolium acetate ([Cyhm$C_1$im][OAc]), 1-(2-naphthylmethyl)-3-methylimidazolium acetate, 1,3-dibenzylimidazolium acetate ([(Bnz)$_2$im][OAc]), and 1-benzyl-3-methylimidazolium acetate [Bnz$C_1$im][OAc], were synthesized by using the above synthesized ionic liquids via anion exchange reactions.

$^1$H and $^{13}$C NMR data and spectra of ILs.

1-heptyl-3-methylimidazolium acetate ([$C_7C_1$im][OAc]). $^1$H NMR (400 MHz; $(CD_3)_2CO$; TMS) 0.89 (t, J=7.2 Hz, 3H, $CH_2\underline{CH_3}$), 1.30-1.38 (m, J=7.0 Hz, 10H, $\underline{CH_2CH_2CH_2CH_2CH_2}CH_3$), 1.80 (s, 3H, $\underline{CH_3}$C=O), 4.13 (s, 3H, N-$\underline{CH_3}$) 4.47 (d, 2H, J=7.0 Hz, N—$\underline{CH_2}$—), 8.02 (d, 2H, J=12.0 Hz, $\overline{NCHCHN}$), 10.64 (s, 1H, $\overline{NCHN}$) ppm.

$^{13}$C NMR, $(CD_3)_2CO$, 100 MHz): 13.5 ($\overline{C_6H_{12}\text{-}\underline{CH_3}}$), 22.4 (—$\underline{CH_2}$—$CH_3$), 25.9 ($\underline{CH_2}$—$CH_2CH_3$), 28.6 ($\underline{CH_3}$C=O), 28.2 ($CH_2$), 29.0 ($\overline{CH_2}$) 29.2 ($\underline{CH_2}$—), 31.5 ($\overline{N\text{—}CH_3}$), 49.1 (N—$CH_2$), 122.3 (NCHCHN), 123.6 (NCHCHN), 138.7 (NCHN), 174.4 (C=O) ppm.

Figure 15:
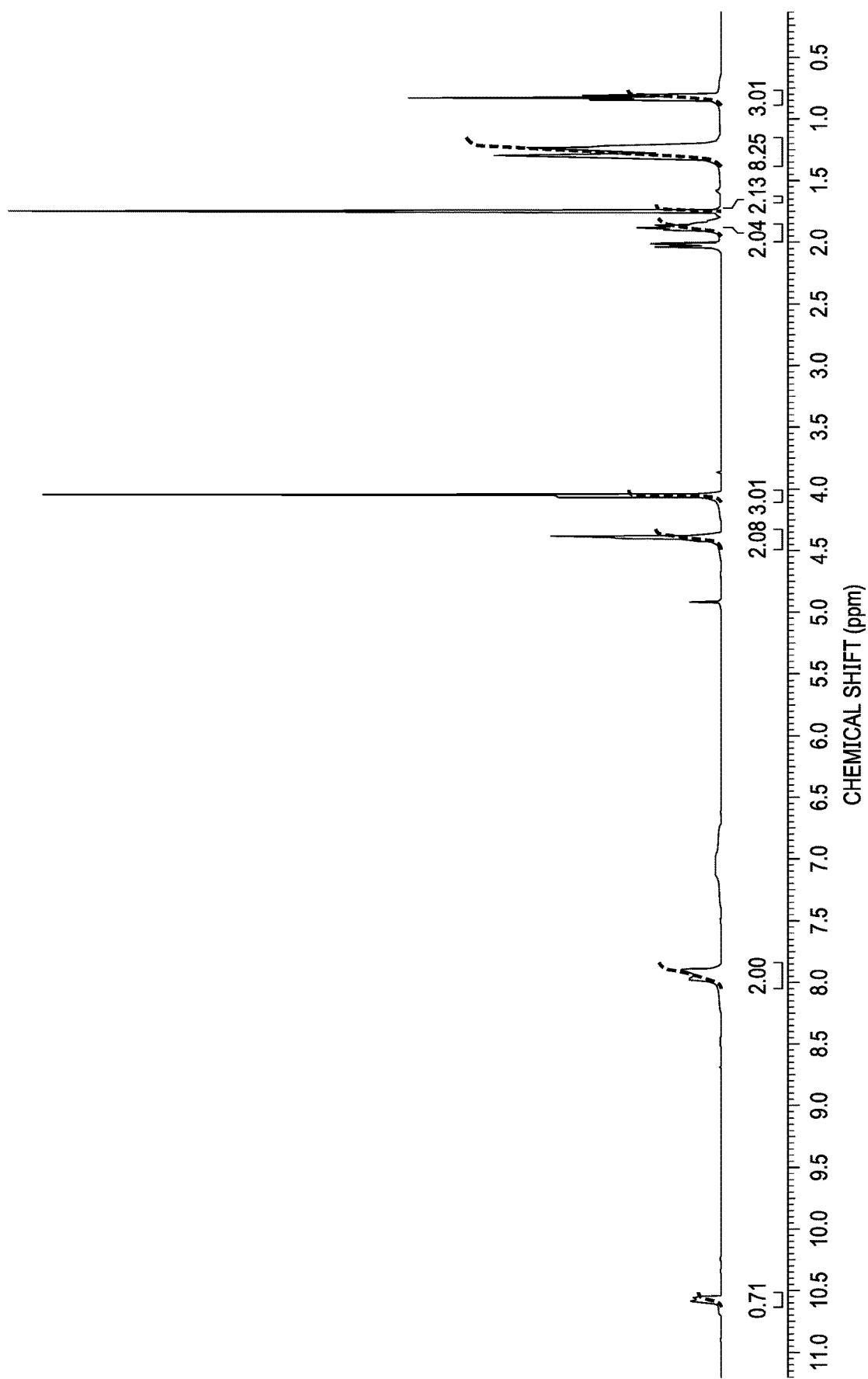
FIG. 15 shows a $^1$H NMR spectrum of [$C_7C_1$im][OAc].

FIG. 15 shows the $^1$H NMR spectrum of 1-heptyl-3-methylimidazolium acetate [$C_7C_1$im][OAc].

Figure 16:
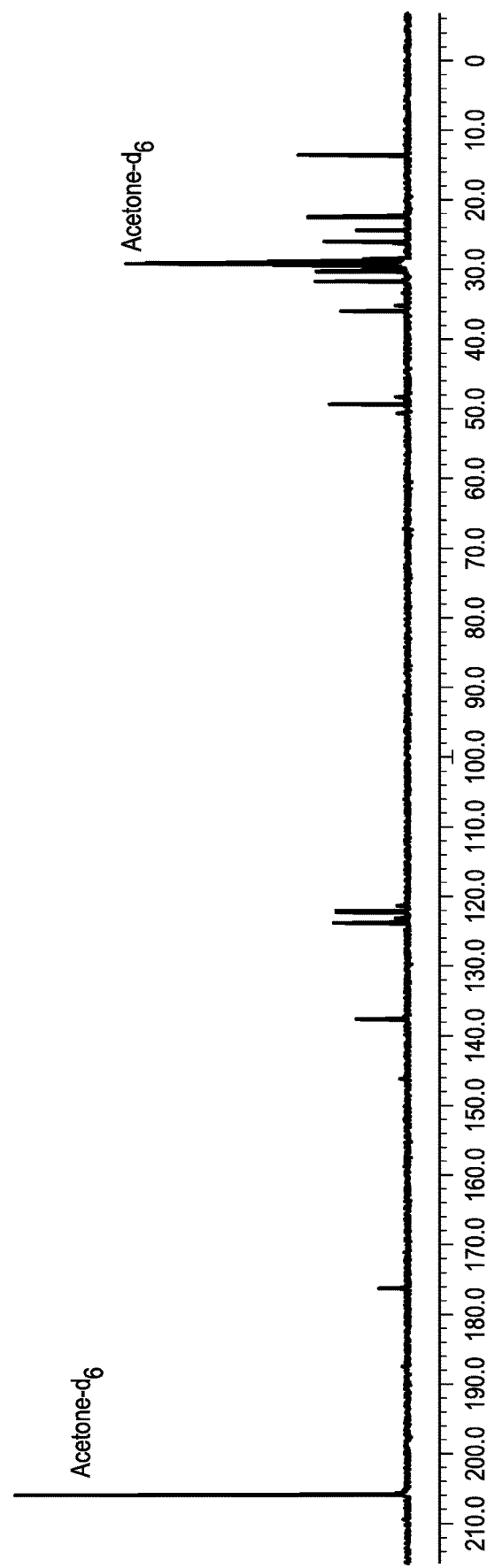
FIG. 16 shows a $^{13}$C NMR spectrum of [$C_7C_1$im][OAc].

FIG. 16 shows the $^{13}$C NMR spectrum of 1-heptyl-3-methylimidazolium acetate [$C_7C_1$im][OAc].

1-(cyclohexylmethyl)-3-methylimidazolium acetate ([CyhmC$_1$im][OAc]). $^1$H NMR (400 MHz; (CD$_3$)$_2$CO; TMS) 0.97-1.22 (m, J=7.2 Hz, 6H, cyclohexyl-CH$_2$), 1.56-1.71 (m, J=7.0 Hz, 4H, cyclohexyl-CH$_2$), 1.70 (s, 3H, CH$_3$C=O), 4.04 (s, 3H, N-CH$_3$), 4.19 (d, 2H, J=7.0 Hz, N—CH$_2$—), 7.69 (d, 2H, J=12.0 Hz, NCHCHN), 11.34 (s, 1H, NCHN) ppm.

$^{13}$C NMR (CD$_3$)$_2$CO, 100 MHz): 24.4 (CH$_2$), 25.3 (CH$_2$) 25.9 (CH$_2$—), 28.4 (CH$_3$C=O), 29.7 (N—CH$_3$), 54.1 (N—CH$_2$), 122.3 (NCHCHN), 123.6 (NCHCHN), 138.7 (NCHN), 174.2 (C=O) ppm.

Figure 17:
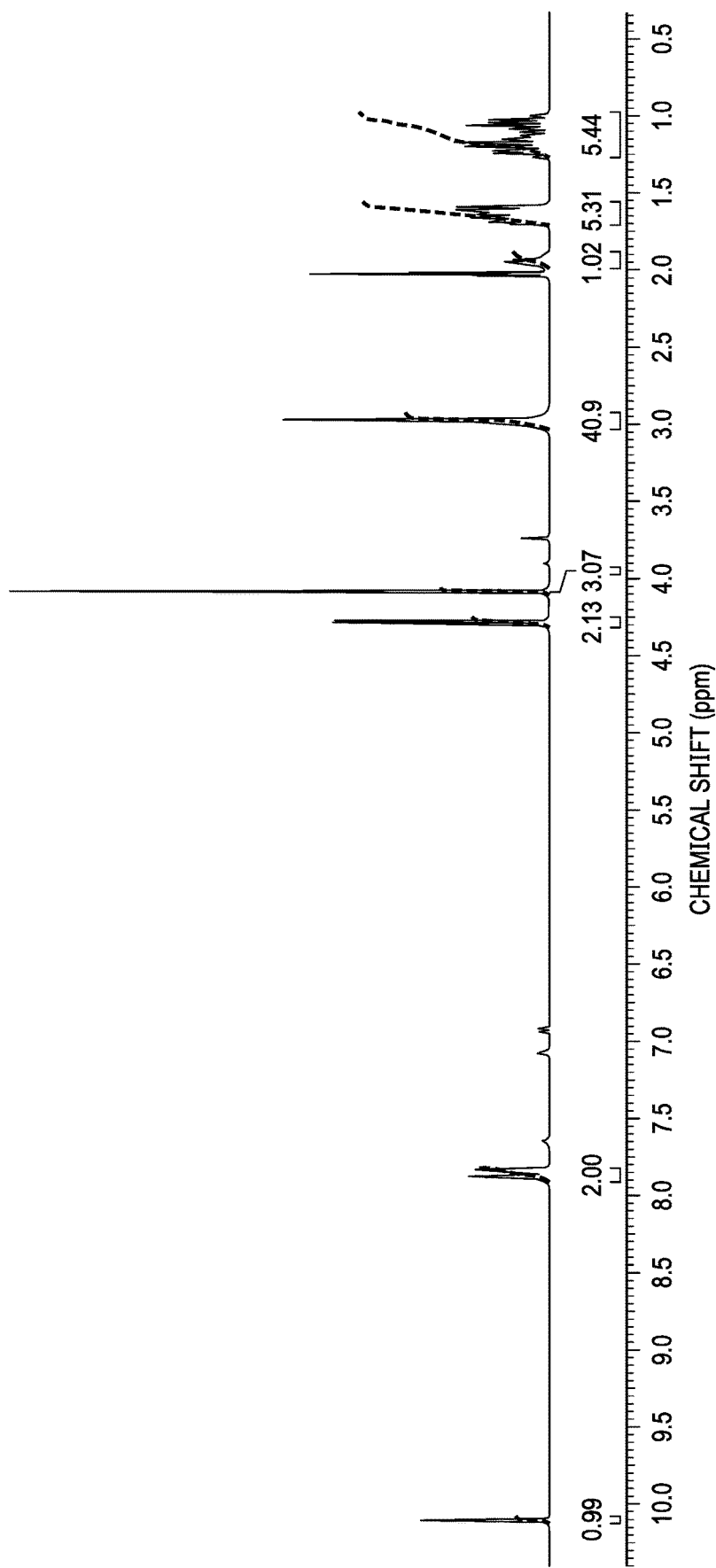
FIG. 17 shows a $^1$H NMR spectrum of [CyhmC$_1$im][OAc].

FIG. 17 shows the $^1$H NMR spectrum of 1-(cyclohexylmethyl)-3-methylimidazolium acetate [CyhmC$_1$im][OAc].

Figure 18:
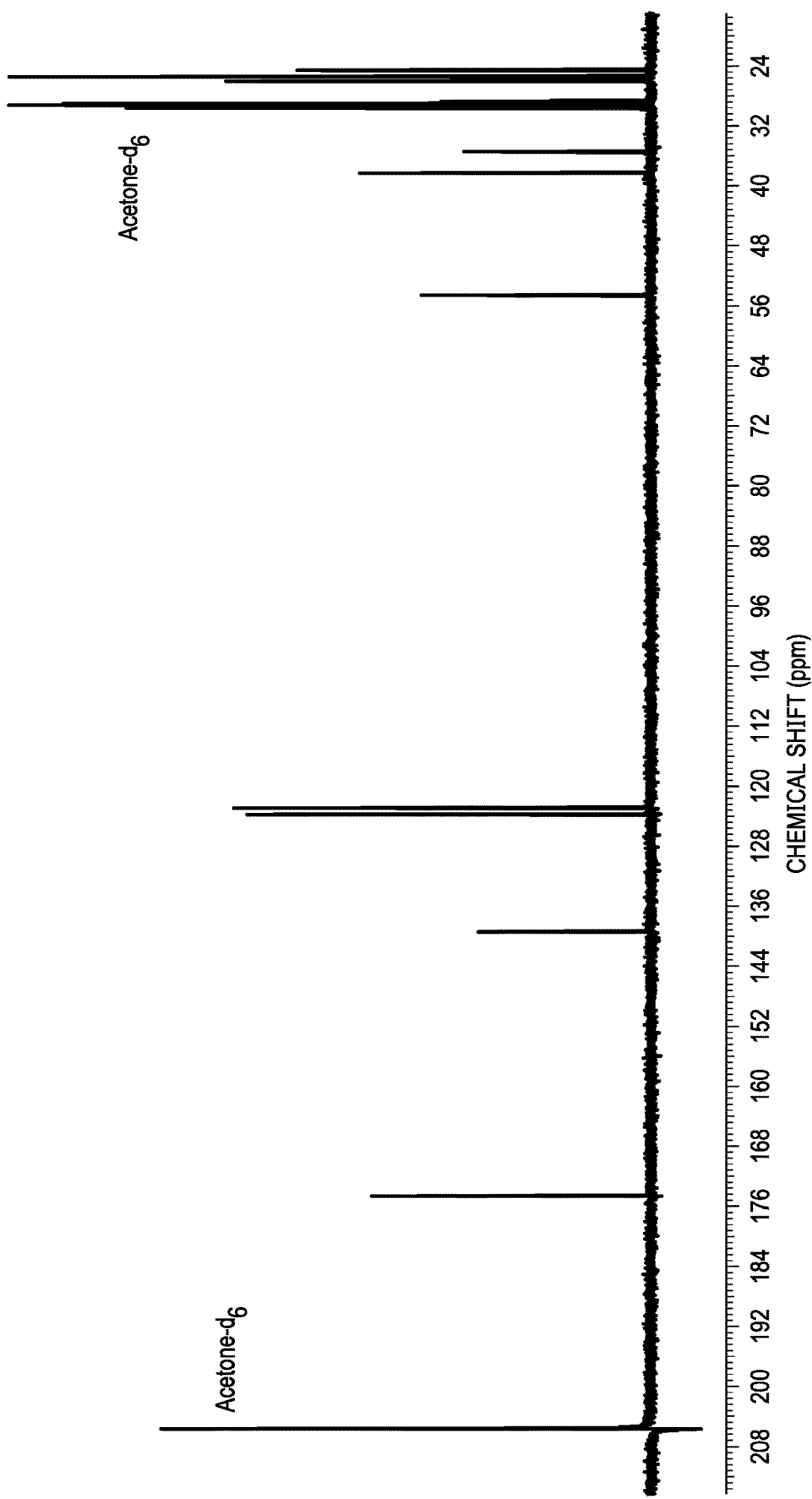
FIG. 18 shows a 13C NMR spectrum of [CyhmC$_1$im][OAc].

FIG. 18 shows the $^{13}$C NMR spectrum of 1-(cyclohexylmethyl)-3-methylimidazolium acetate [CyhmC$_1$im][OAc].

1-(2-naphthylmethyl)-3-methylimidazolium acetate ([NapmC$_1$im][OAc]). $^1$H NMR (400 MHz; DMSO-d$_6$; TMS) 1.10 (s, 3H, CH$_3$C=O), 4.10 (d, 4H, J=7.0 Hz, N—CH$_2$—), 7.28-7.52 (m, 7H), 7.53 (d, 2H, J=12.0 Hz, NCHCHN), 9.28 (s, 1H, NCHN) ppm. $^{13}$C NMR (DMSO-d$_6$, 100 MHz): 25.8 (CH$_3$C=O), 30.7 (N—CH$_3$), 51.2 (N—CH$_2$), 122.9 (NCHCHN), 123.0 (NCHCHN), 128.5, 129.5, 136.1 (aromatic), 139.72 (NCHN), 174.3 (C=O) ppm.

Figure 19:
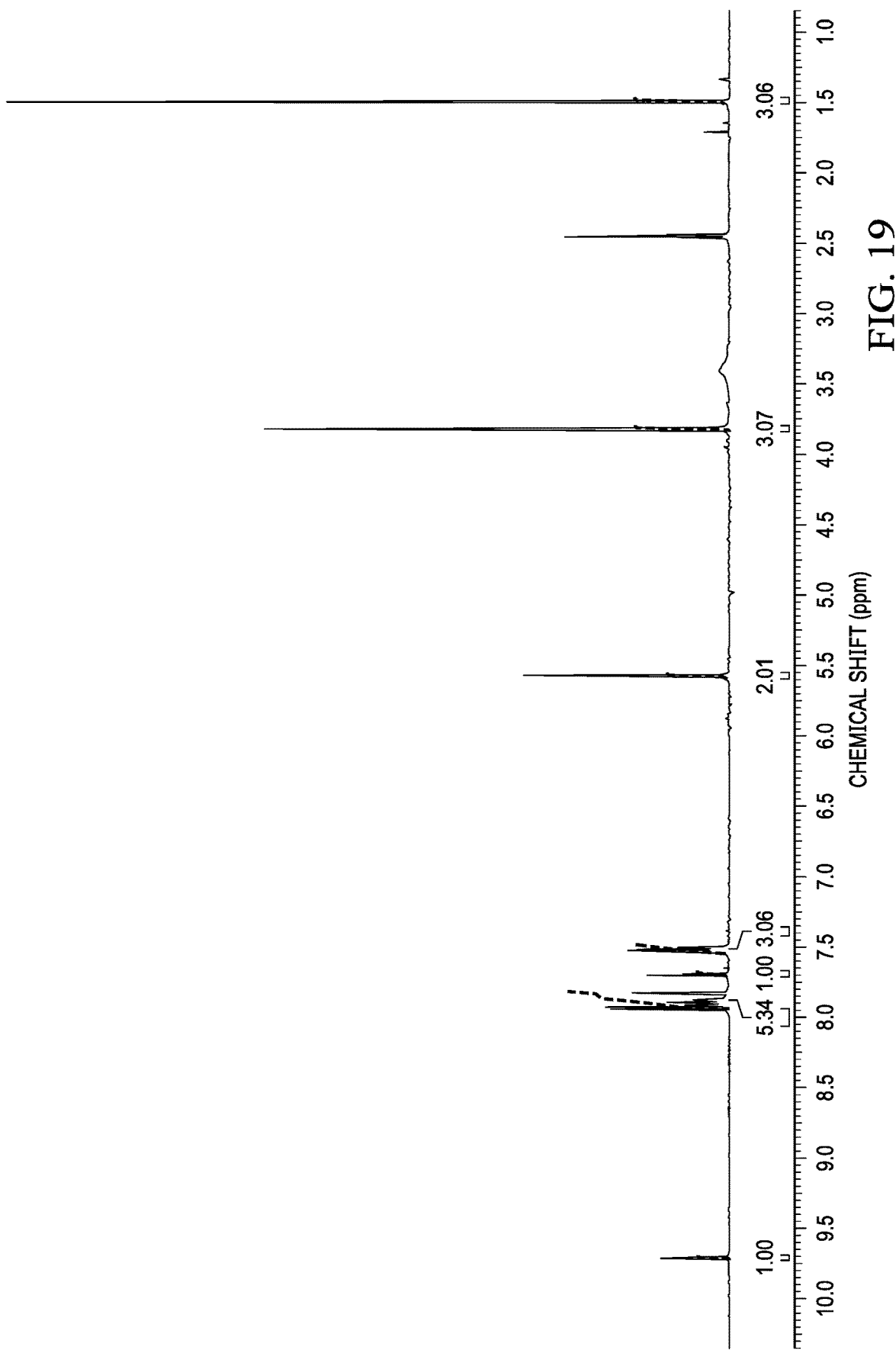
FIG. 19 shows a H NMR spectrum of [NapmC$_1$im][OAc].

FIG. 19 shows the $^1$H NMR spectrum of [NapmC$_1$im][OAc].

Figure 20:
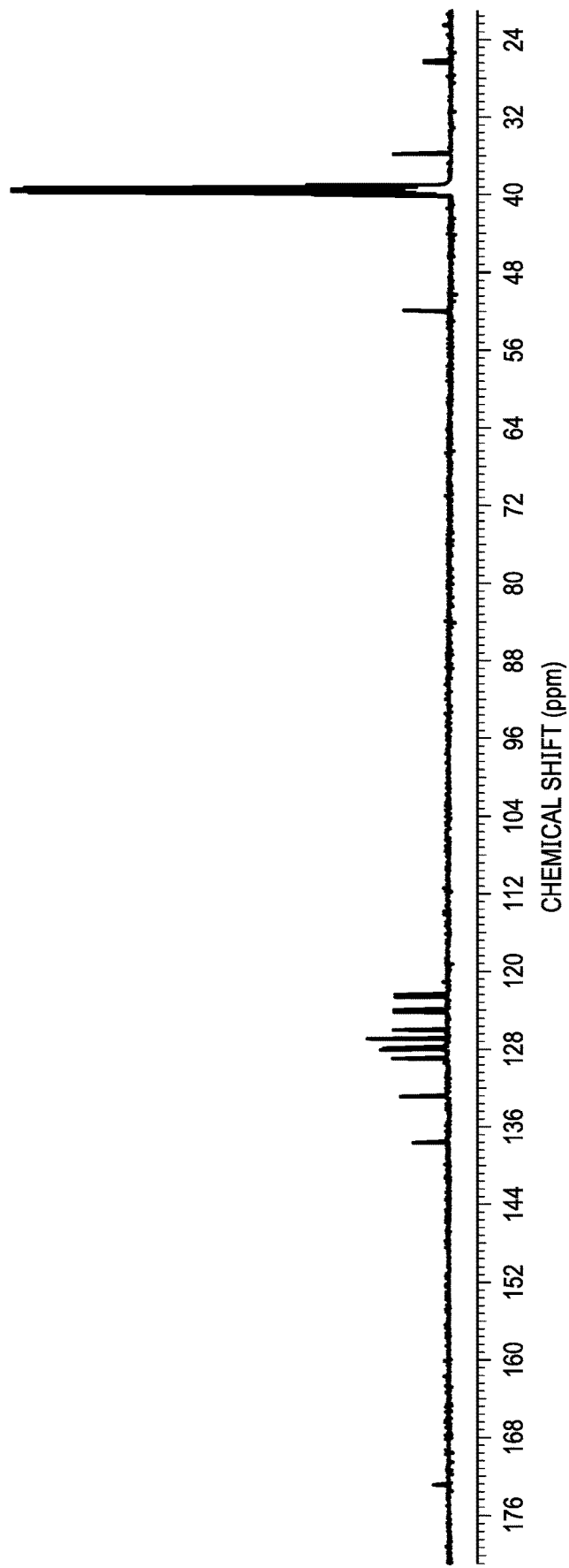
FIG. 20 shows a $^{13}$C NMR spectrum of [NapmC$_1$im][OAc].

FIG. 20 shows the $^{13}$C NMR spectrum of [NapmC$_1$im][OAc].

1,3-dibenzylimidazolium acetate ([(Bnz)$_2$im][OAc]). $^1$H NMR (400 MHz; (DMSO-d$_6$); TMS) 0.98 (s, 3H, CH$_3$C=O), 4.57 (d, 4H, J=7.0 Hz, N-CH$_2$—), 6.28-6.52 (m, 10H), 6.53 (d, 2H, J=12.0 Hz, NCHCHN), 10.28 (s, 1H, NCHN) ppm.

$^{13}$C NMR (DMSO-d$_6$, 100 MHz): 25.5 (CH$_3$C=O), 53.2 (N—CH$_2$), 122.9 (NCHCHN), 123.0 (NCHCHN), 129.5, 129.7136.1 (aromatic), 140.72 (NCHN), 174.2 (C=O) ppm.

Figure 21:
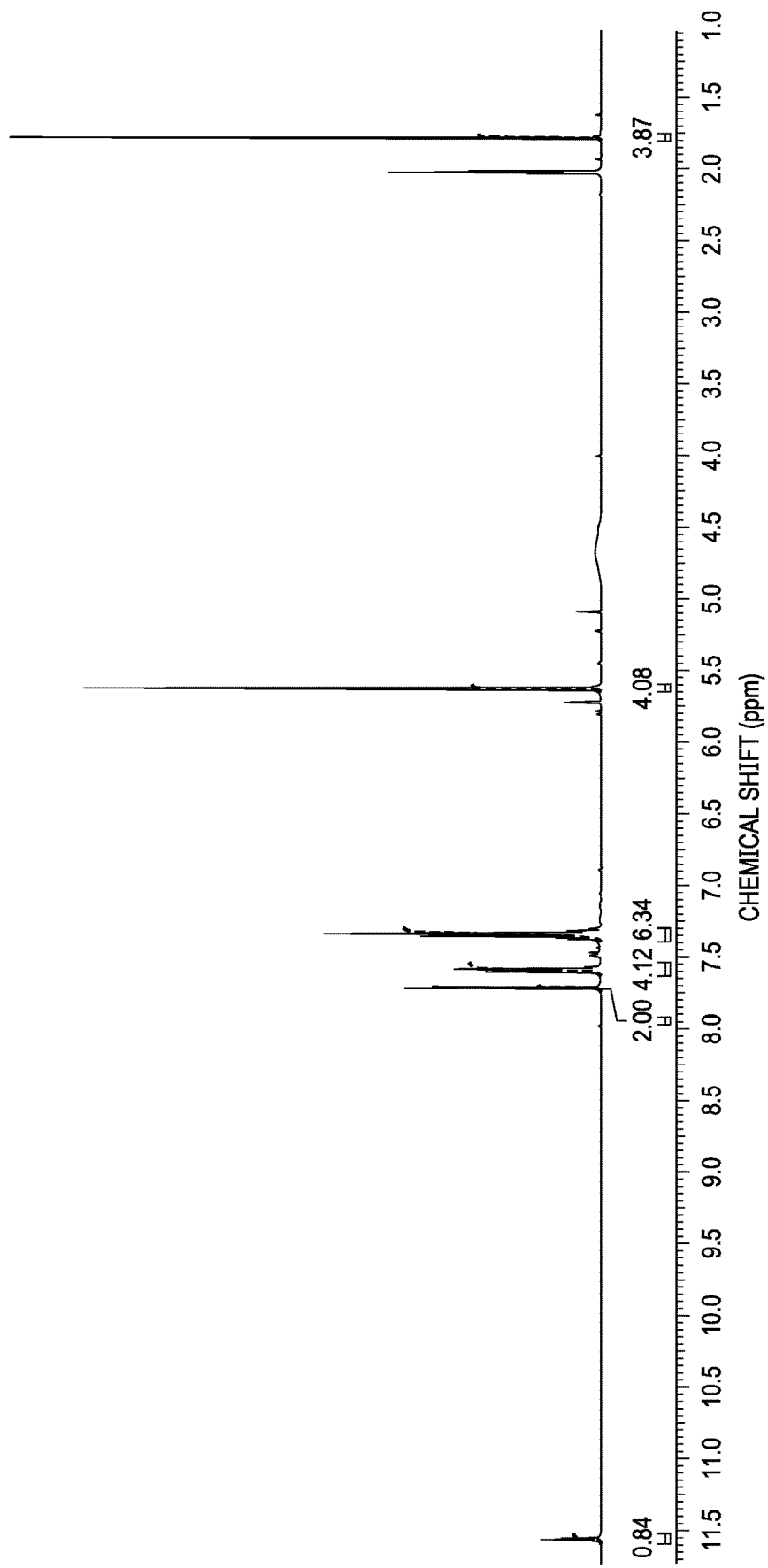
FIG. 21 shows a H NMR spectrum of [(Bnz)$_2$im][OAc].

FIG. 21 shows the $^1$H NMR spectrum of [(Bnz)$_2$im][OAc].

Figure 22:
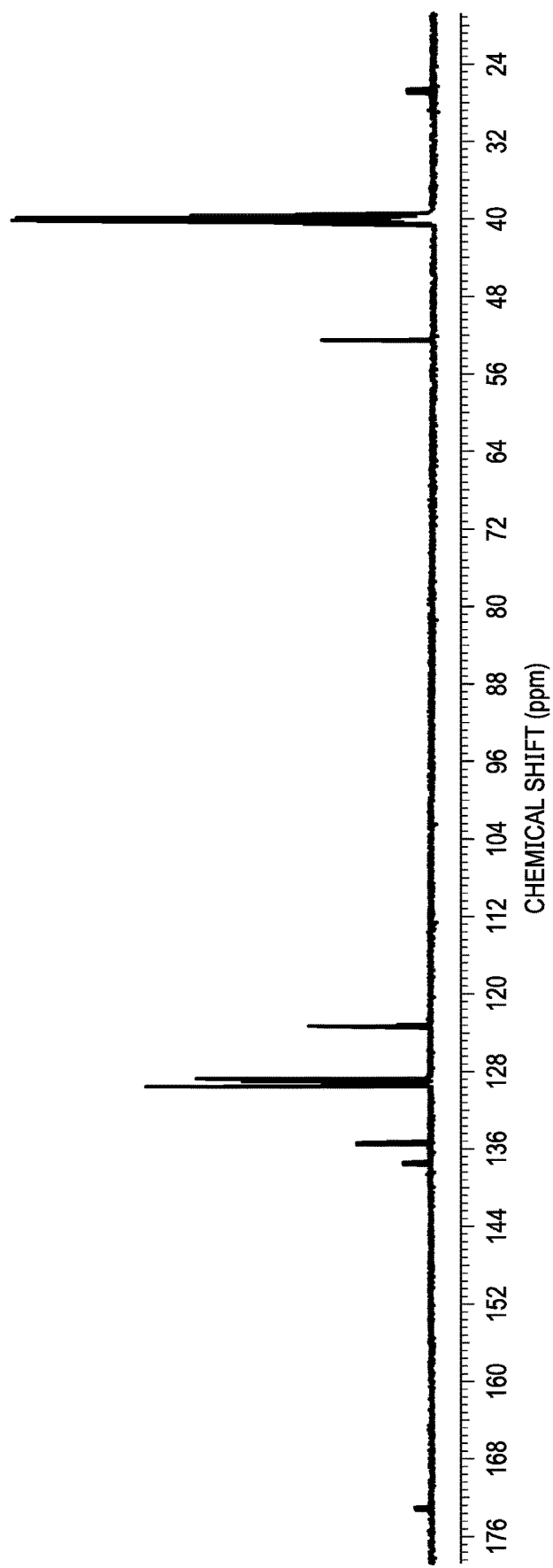
FIG. 22 shows a $^{13}$C NMR spectrum of [(Bnz)$_2$im][OAc].

FIG. 22 shows the $^{13}$C NMR spectrum of [(Bnz)$_2$im][OAc].

1-benzyl-3-methylimidazolium acetate [BnzC$_1$im][OAc]. $^1$H NMR (400 MHz; (DMSO-d$_6$); TMS) 1.54 (s, 3H, CH$_3$C=O), 3.86 (s, 3H, N—CH$_3$), 4.57 (s, 2H, N-CH$_2$—), 7.40-7.43 (m, 5H), 7.72-7.78 (d, 2H, J=12.0 Hz, NCHCHN), 9.67 (s, 1H, NCHN) ppm.

$^{13}$C NMR (DMSO-d$_6$, 100 MHz): 26.0 (CH$_3$C=O), 36.2 (N—CH3), 52.2 (N—CH$_2$), 122.7 (NCHCHN), 124.0 (NCHCHN), 129, 129.4, 135.1 (aromatic), 138.10 (NCHN), 173.2 (C=O) ppm.

Figure 23:
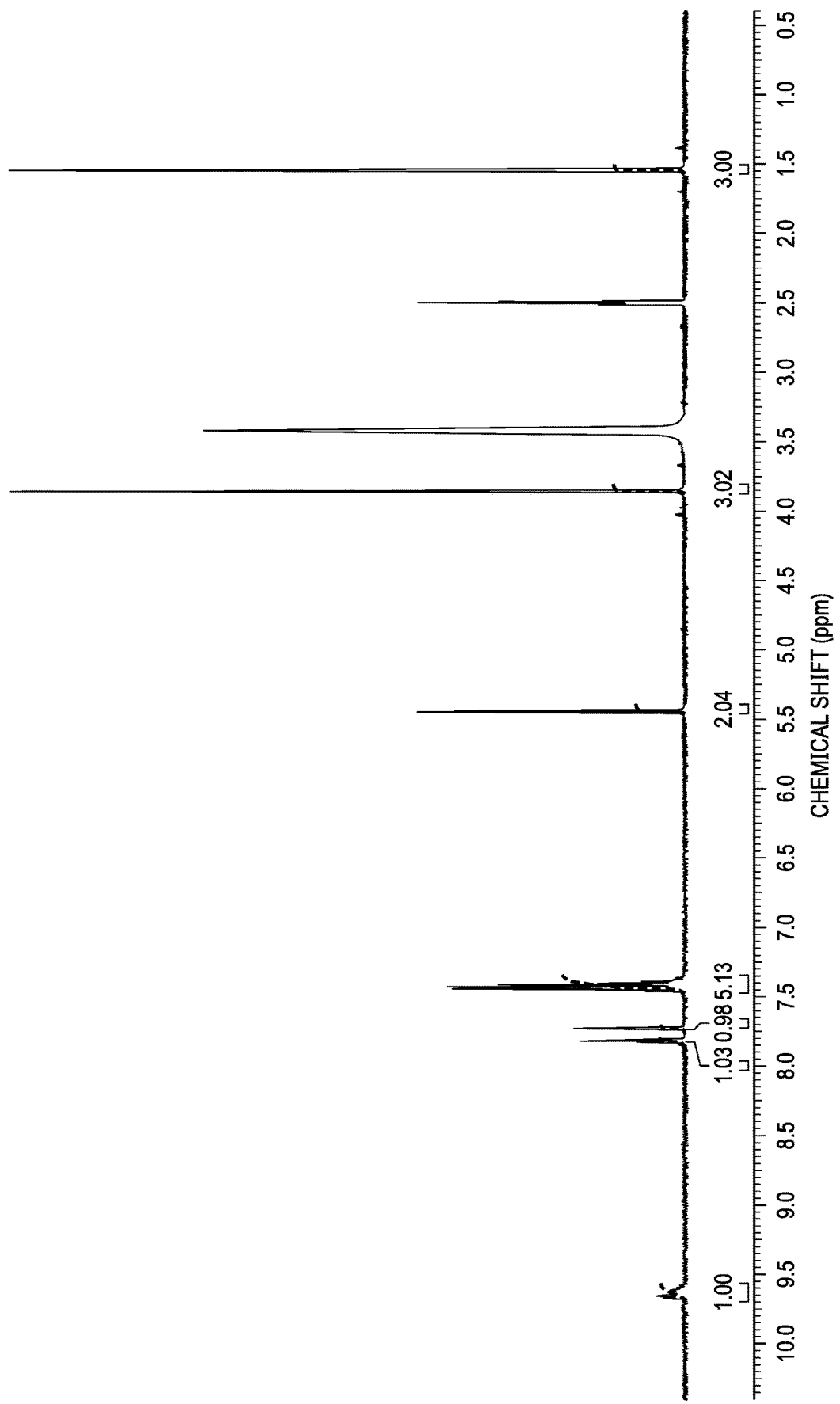
FIG. 23 shows a $^1$H NMR spectrum of [BnzC$_1$im][OAc].

FIG. 23 shows the $^1$H NMR spectrum of [BnzC$_1$im][OAc].

Figure 24:
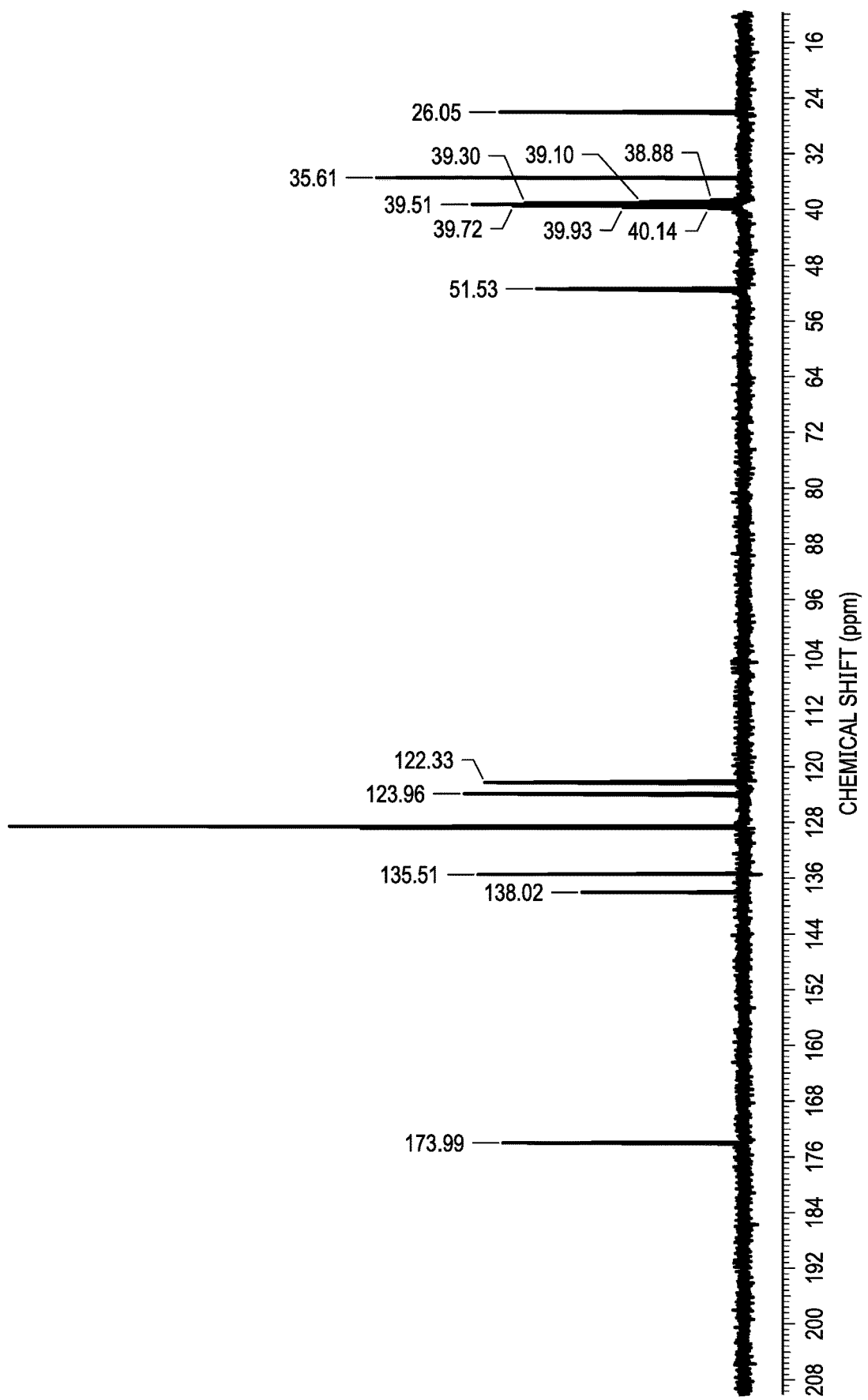
FIG. 24 shows a $^{13}$C NMR spectrum of [BnzC$_1$im][OAc].

FIG. 24 shows the $^{13}$C NMR spectrum of [BnzC$_1$im][OAc].

Figure 25A:
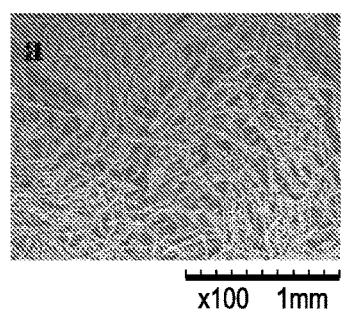
FIGS. 25A and 25B show freeze-dried cellulose regenerated from ground cotton fibers dissolved in [$C_7C_1$im][OAc].
Figure 25B:
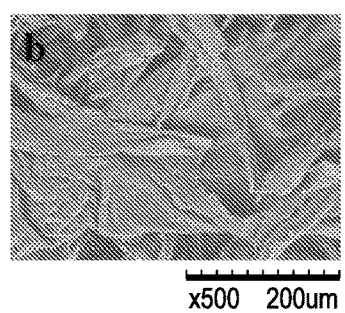

FIGS. 25A and 25B show freeze-dried cellulose regenerated from ground cotton fibers dissolved in [C$_7$C$_1$im][OAc], FIG. 25A—SEM 100×, and FIG. 25B—SEM 500×.

Figure 26A:
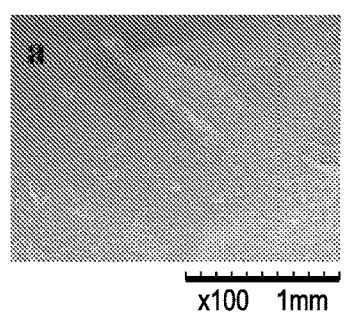
FIGS. 26A and 26B show freeze-dried film regenerated from ground cotton dissolved in [BnzC$_1$im][OAc] FIG. 26A SEM 100× and FIG. 26B SEM 500×.
Figure 26B:
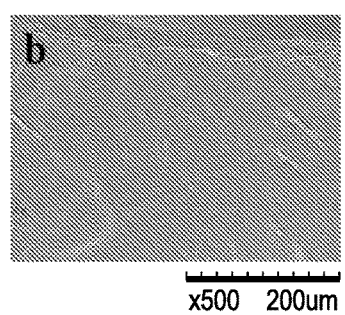

FIGS. 26A and 26B show freeze-dried film regenerated from ground cotton dissolved in [BnzC$_1$im][OAc]. FIG. 26A—SEM 100×, and FIG. 26B—SEM 500×.

Figure 27A:
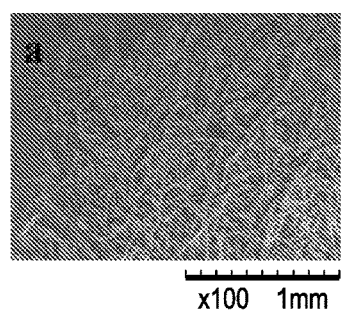
FIGS. 27A and 27B show freeze-dried film regenerated from ground cotton dissolved in [CyhmC$_1$im][OAc].
Figure 27B:
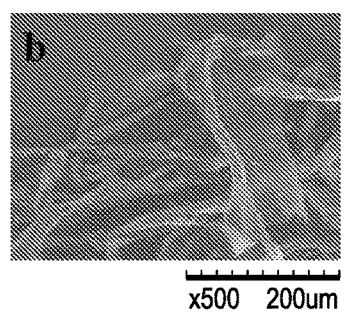

FIGS. 27A and 27B show freeze-dried film regenerated from ground cotton dissolved in [CyhmC$_1$im][OAc]. FIG. 27A—SEM 100×, and FIG. 27B—SEM 500×.

Figure 28A:
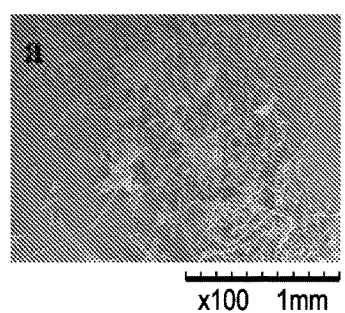
FIGS. 28A and 28B show freeze-dried film regenerated from ground cotton dissolved in [NapmC$_1$im][OAc].
Figure 28B:
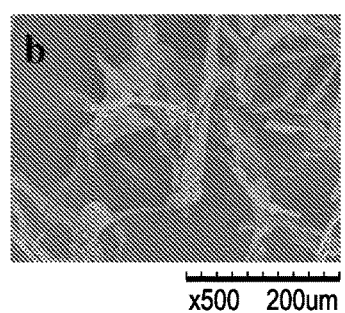

FIGS. 28A and 28B show freeze-dried film regenerated from ground cotton dissolved in [NapmC$_1$im][OAc]. FIG. 28A—SEM 100×, and FIG. 28B—SEM 500×.

Figure 29A:
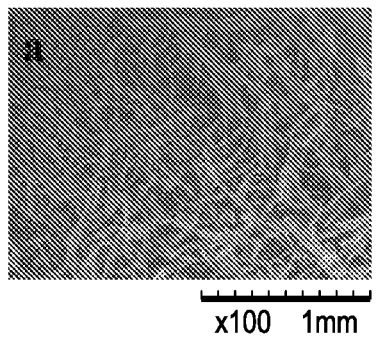
FIGS. 29A and 29B show freeze-dried film regenerated from ground cotton dissolved in [(Bnz)$_2$im][OAc].
Figure 29B:
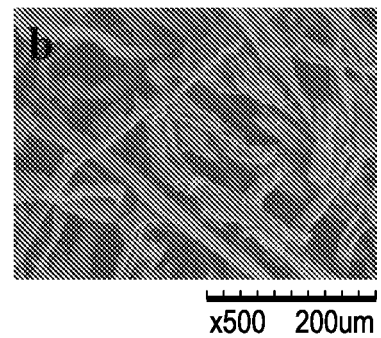

FIGS. 29A-29B show freeze-dried film regenerated from ground cotton dissolved in [(Bnz)$_2$im][OAc].

Figure 30:
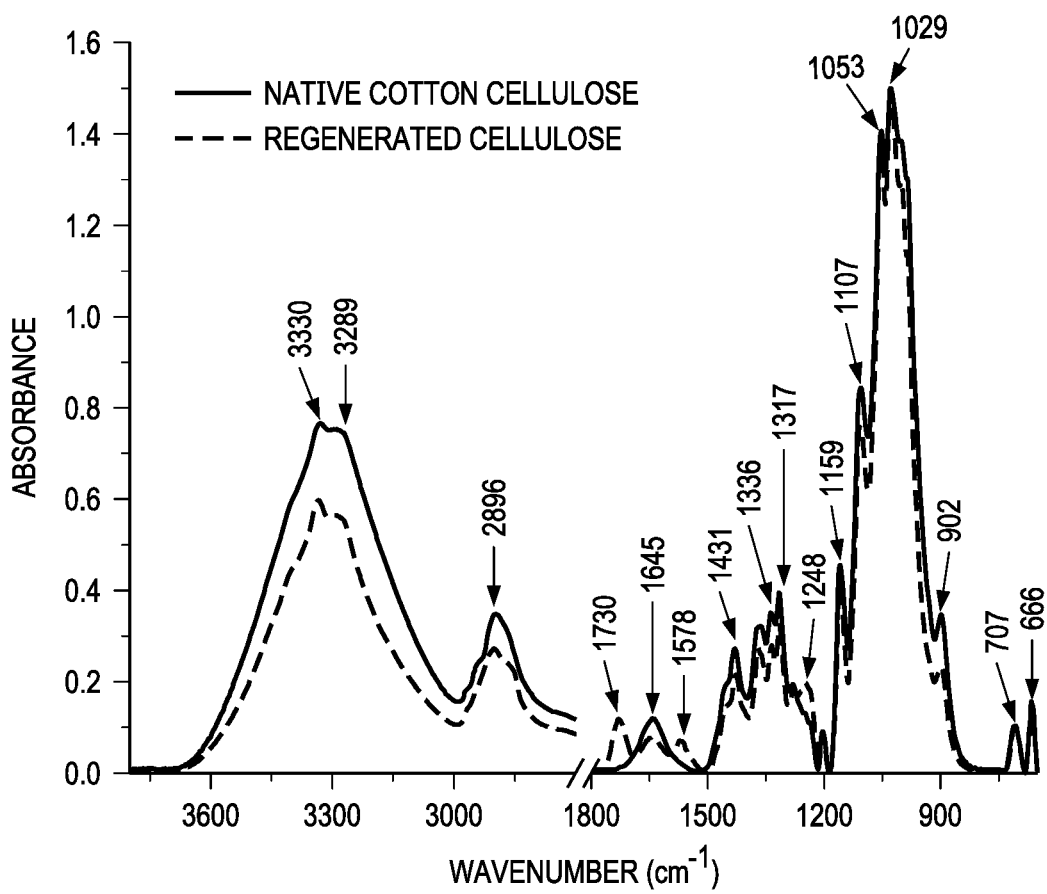
FIG. 30 shows FTIR spectra of ground cotton cellulose and freeze-dried cellulose regenerated from [$C_7C_1$im][OAc].

FIG. 30 shows FTIR spectra of ground cotton cellulose and freeze-dried cellulose regenerated from [C$_7$C$_1$Im][OAc].

Figure 31:
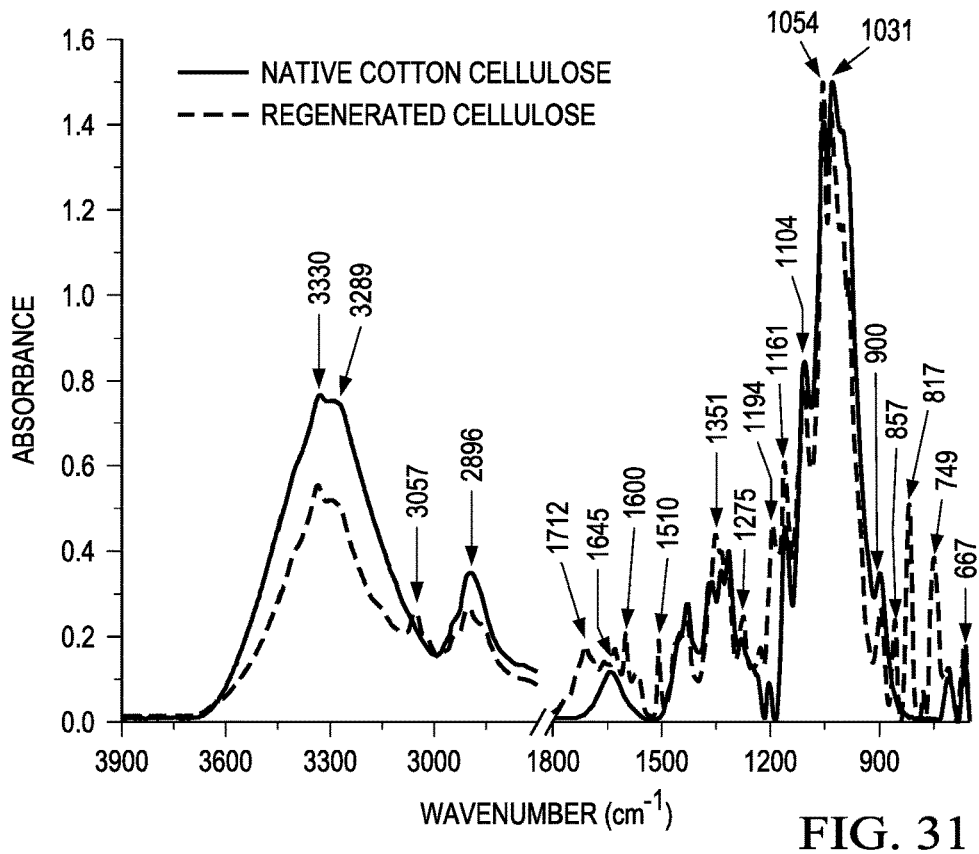
FIG. 31 shows FTIR spectra of ground cotton cellulose and freeze-dried cellulose regenerated from [NapmC$_1$im][OAc].

FIG. 31 shows FTIR spectra of ground cotton cellulose and freeze-dried cellulose regenerated from [NapmC$_1$im][OAc].

Figure 32:
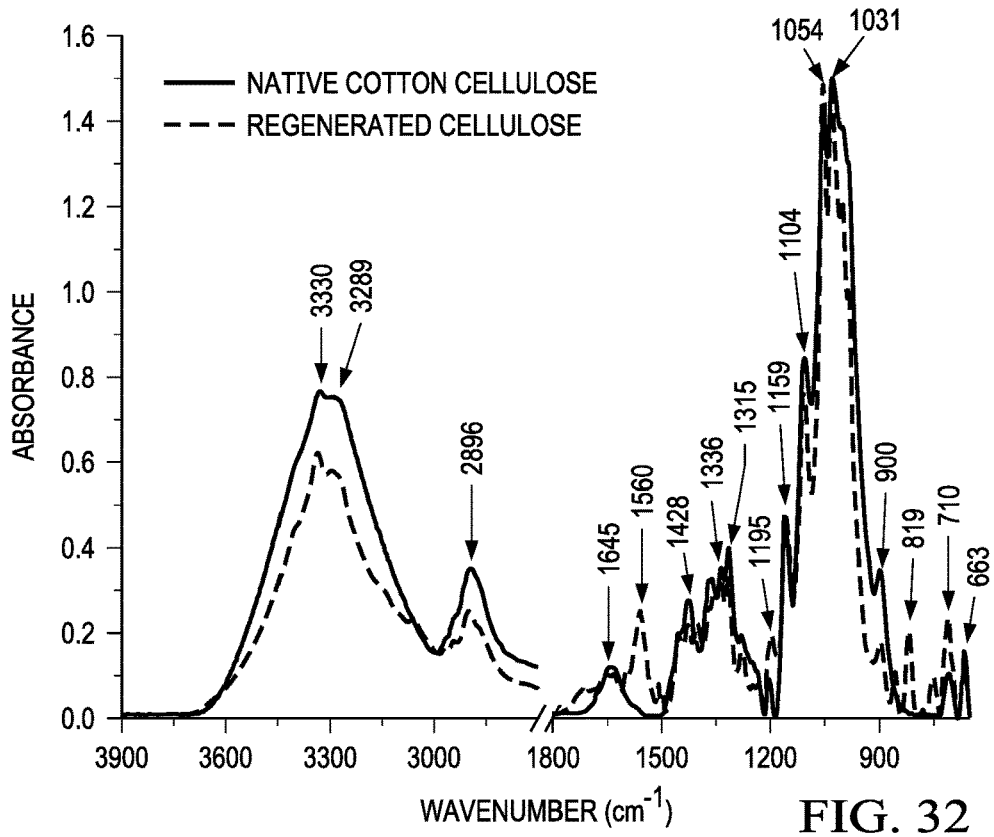
FIG. 32 shows FTIR spectra of ground cotton cellulose and freeze-dried cellulose regenerated from [(Bnz)$_2$im][OAc].

FIG. 32 shows FTIR spectra of ground cotton cellulose and freeze-dried cellulose regenerated from [(Bnz)$_2$im][OAc].

Figure 33:
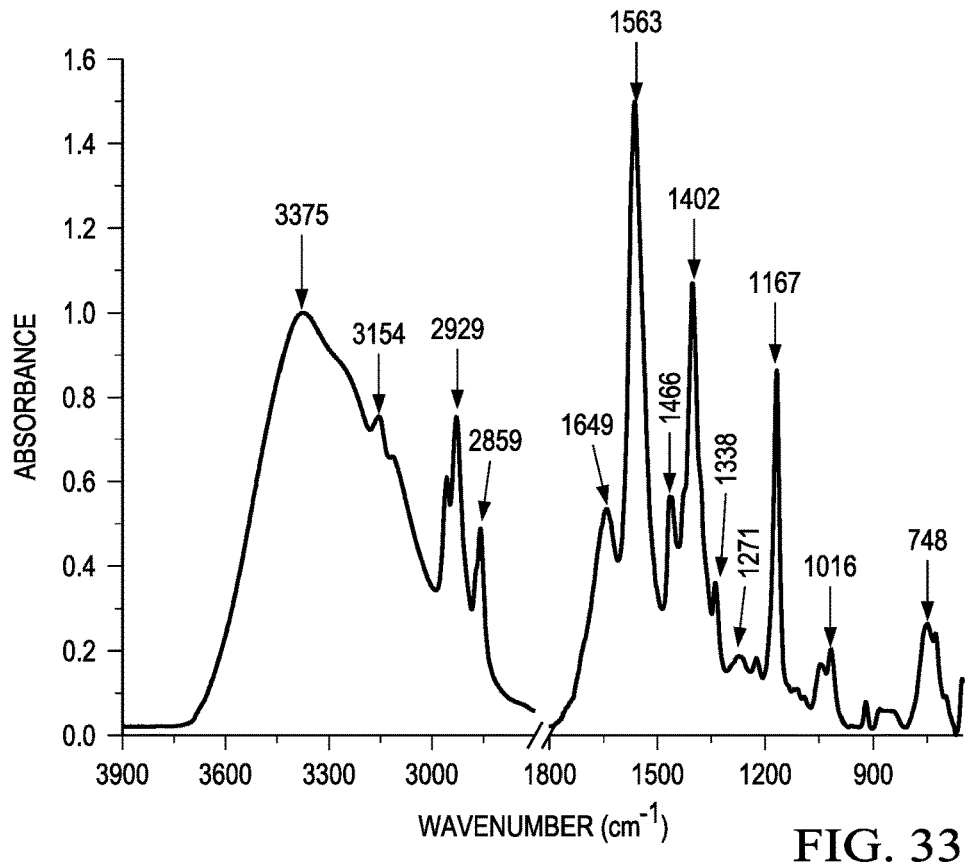
FIG. 33 shows FTIR spectrum of neat [$C_7C_1$im][OAc].

FIG. 33 shows FTIR spectrum of neat [C$_7$C$_1$im][OAc].

Figure 34:
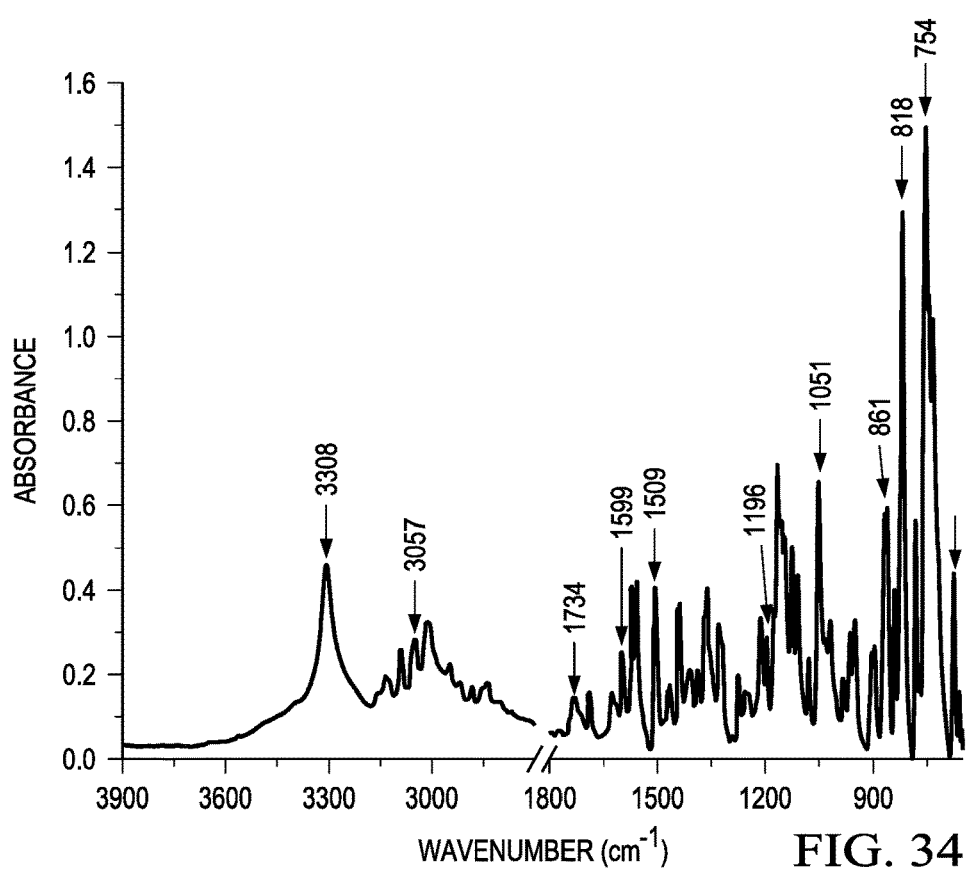
FIG. 34 shows FTIR spectrum of neat [NapmC$_1$im][OAc].

FIG. 34 shows FTIR spectrum of neat [NapmC$_1$im][OAc].

Example 3. Cellulose Dissolution in Ionic Liquids

Electrospinning. Electrospinning is one of the simplest and the most cost-effective methods to produce ultrathin fibers. These fibers possess interesting characteristics, such as high surface to volume ratio and porosity with excellent pore interconnectivity. Various natural and synthetic polymers have been utilized in electrospinning to generate nanofibers. However, electrospinning of some natural polymers including cellulose is still a challenge. Up to this point, research groups have explored the electrospinning of cellulose suspensions where cellulose is dissolved mostly in DMAc/LiCl. Only a few studies have been reported where ionic liquids (ILs) are used as solvents for electrospinning.

During the electrospinning process, the polymer solution or the melt is charged by an external electric source. Initially, the polymer solution is held by its surface tension to prevent the pendant drop from emerging from the top of the tip. At this stage, the equilibrium is reached between the surface tension of the droplet and the electrostatic forces produced by the external electric field. As the electric field is increased, the tensile forces are exerted on the liquid, and the droplet is elongated to form a conical shape. The point of eruption of the droplet is referred to as the Taylor cone (FIG. 35). FIG. 35 shows a general set-up of an electrospinning process 10, that includes a syringe or injector 12, a polymer solution 14 within the syringe or injector 12, a needle 16, a collector 18, and a voltage power supply 20. A liquid jet 22 is formed by pressurizing the polymer solution 14 in the syringe or injector 12, which is ejected at the needle 16, and the voltage difference causes the cellulose fibers to be attracted to the collector 18. As the strength of the electric field is further increased, the electrostatic repulsive interactions counteract the surface tension. Because of this, the charged solution ejects from the surface of the droplet towards the end of the capillary tube and then accelerates in the direction of the collector. While the jet is propagated towards the collector, it undergoes an unstable and rapid chaotic bending that aids the evaporation of the solvent. This results in a fibrous scaffold consisting of small pore size and large surface area-to-volume ratio. When the solvent is removed, or melt solidifies, the polymer is collected as a nonwoven mat. These mats are used in various applications such as filtration, protective clothing, and biomedical applications.

The composition of the cellulose solutions was varied to determine the range of cellulose concentration suitable for electrospinning. Other parameters such as the viscosity of the polymer solution, the electrical field (voltage), and the distance between the tip of the needle (spinneret) and the collector are also important for obtaining submicron scale fibers. In order to figure out those parameters, readily available solvents were used in the initial experiments. The first few experiments were performed using a polymer solution of 5% microcrystalline cellulose (MCC) dissolved in DMAc/LiCl. Then, two commercially available ILs, 1-butyl-3-methylimidazolium chloride ([$C_4C_1$im][Cl]) and 1-butyl-3-methylimidazolium acetate ([$C_4C_1$im][OAc]), were used as cellulose solvents. These solutions were subjected to electrospinning and the resulting products were analyzed using a microscope. After determining the required parameters and conditions, 1-butyl-3-methylimidazolium phosphonate ([$C_4C_1$im][(OMe)(H)$PO_2$]) and 1-methylimidazole co-solvent were used to prepare cellulose solutions for the electrospinning studies. As show above, this IL-cosolvent mixture was more effective in dissolving cellulose compared to either [$C_4C_1$im][Cl] or [$C_4C_1$im][OAc]. Moreover, cellulose solutions prepared with this IL-cosolvent mixture led to continuous fiber formation, unlike cellulose solution prepared with either [$C_4C_1$im][Cl] or [$C_4C_1$im][OAc].

Preparation of DMAc/LiCl cellulose solution. A 5% (w/v) cellulose suspension was prepared by adding microcrystalline cellulose (MCC, Avicel PH 101) to 100 ml of DMAc. MCC was first placed in a 105° C. oven for 3 hours to remove moisture. Then, 100 ml of DMAc was added to a beaker using a pipette. It was then heated at 80° C. for 10-15 minutes to remove moisture. MCC was added to DMAc and the mixture was stirred at 80° C. for 30 minutes. Then, 8 g of oven-dried LiCl was slowly added to the mixture and stirred at 80° C. or 3 hours. The temperature was decreased to 50° C. and the solution was stirred overnight at this temperature. The total time for the dissolution of MCC in DMAc/LiCl was 19 hours.

Electrospinning of the DMAc/LiCl cellulose solution. The electrospinning apparatus at the Department of Industrial, Manufacturing and System Engineering at Texas Tech University was utilized to electrospin cellulose solution. For these studies, the cellulose suspension was loaded into a 8 ml syringe placed inside the chamber of the electrospinning apparatus. A piece of aluminum foil was placed 10 cm away from the tip of the nozzle and a glass slide was placed on it to collect the fibers. Electrospinning of cellulose solution was conducted at 15 kV/10 cm and 16 kV/5.5 cm at room temperature. The materials that were spun onto the glass slide were examined using high resolution microscope.

Preparation of [$C_4C_1$im][Cl] and [$C_4C_1$im][OAc] cellulose solution. At room temperature [$C_4C_1$im][Cl] is a solid, whereas [$C_4C_1$im][OAc] is a liquid. [$C_4C_1$im][Cl] was melted by heating in an oven at 85° C. for 4 hours. Cotton was scoured and bleached, then ground using a Wiley mill to pass 20 mesh size. Then, cotton was dried at 105° C. overnight to remove the moisture. Cellulose suspensions of 1% (w/w) and 3% (w/w) were prepared. The cotton cellulose was first weighed and then slowly added to the glass jar that contained the ionic liquid. The mixture was heated in a microwave oven using 3-4 sec. pulses to reach the temperature of the solution to 90-100° C.

Electrospinning of the [$C_4C_1$im][Cl] cellulose solution. The cellulose suspension with 1% (w/w) cotton dissolved in [$C_4C_1$im][Cl] was spun at three different voltages; 18 kV/16 cm, 20 kV/23.2 cm, and 25 kV/16 cm. Spun materials were collected on glass slides that were placed on a grounded aluminum foil in a distilled water bath. The 3% (w/w) cotton cellulose in [$C_4C_1$im][Cl] was electrospun at a voltage range of 10-25 kV. The materials collected were examined using a high-resolution microscope. Electrospinning of cellulose solutions prepared in [$C_4C_1$im][OAc] was not successful, yielding only droplets.

Preparation of [$C_4C_1$im][(OMe)(H)$PO_2$] and 1-methylimidazole cellulose solution. Two solutions of 5% cotton cellulose in an equimolar mixture of [$C_4C_1$im][(OMe)(H)$PO_2$] and 1-methylimidazole were prepared. Cotton fibers were first scoured and bleached and then ground using a Willey mill to pass 20 mesh sizes. Ethanol treatment was performed to the resulting cotton powder by agitating it in absolute ethanol for 4 hours at room temperature. The ethanol-treated cotton powder was dried at 55° C. for 8 hours. An equimolar mixture of [$C_4C_1$im][(OMe)(H)$PO_2$] and 1-methylimidazole was prepared. The ethanol-treated cotton powder was slowly added to the solvents mixture and the suspension was heated to 90-100° C. in a microwave oven using 3-4 sec. pulses. The suspension was then transferred to a 90° C. oven and heated for 15 minutes. Cellulosic suspension was subjected to electrospinning to investigate its ability to form fibers.

Electrospinning of [$C_4C_1$im][(OMe)(H)$PO_2$] and 1-methylimidazole cellulose solution. Electrospinning was performed for the solution at the voltage of 18 kV/18 cm. The resulting fibers were collected on a glass slide. Other solution was prepared by adding 3-4 drops of Reactive Blue 19 Dye to 1-methylimidazole, mixing equi-molar amount of IL and dissolving cellulose. The dyed cellulose solution was spun into a water bath at the voltage of 15 kV/15 cm.

Preparation of [$C_4C_1$im][(OMe)(H)$PO_2$] and dimethylformamide cellulose solution. Ethanol treated cotton was dissolved in 1 to 1 molar ratio of IL and dimethylformamide (DMF) by heating to 90-100° C. in a microwave oven using 3-4 sec. pulses. The suspension was then transferred to an oven and heated at 90° C. to achieve complete dissolution.

Electrospinning of [$C_4C_1$im][(OMe)(H)$PO_2$] and dimethylformamide cellulose solution. Electrospinning was performed at the voltage of 18-20 kV and a flow rate of 3 ml/h. The resulting materials were collected and analyzed using a microscope.

Characterization of regenerated cellulose.

Scanning Electron Microscope (SEM). Air-dried, regenerated cellulose fibers were mounted on carbon discs with no coating. A Hitachi TM-1000 tabletop environmental scanning electron microscope, at an accelerating voltage of 15 kV, was used to record the images of regenerated cellulose fibers.

Fourier Transform Infrared Spectroscopy (FTIR). Air-dried-regenerated cellulose fibers and hot-dried ground cotton fibers were kept in the laboratory at 21±1° C. at 65±2% relative humidity for 2 days before FTIR analysis. The FTIR spectrum of regenerated cellulose samples were collected using an FTIR instrument equipped with an UATR accessory and ZnSe-Diamond. The ZnSe-Diamond crystal was cleaned using Milli-Q water and ethanol. Background spectra of the clean crystal was obtained prior to obtaining spectra of the samples. A small portion of each sample was placed on the ZnSe-Diamond crystal and a constant pressure was applied using a "pressure arm" to ensure a good contact between the sample and the IR beam. FTIR spectra of regenerated cellulose samples were collected in the mid-IR range from 650-4000 $cm^{-1}$ at a resolution of 4 $cm^{-1}$ with 32 co-added scans. Each spectrum was subjected to baseline correction and normalization using Perkin-Elmer software.

During the dissolution of cellulose in DMAc/LiCl, the suspension initially became cloudy. However, it became clear and less viscous solution after heating overnight at 50° C. When these solutions were electrospun, Taylor cone formation was not detected. The polymer solution was sprayed onto the glass slide. The microscopic images of the resulting materials are shown in FIGS. 36A and 36B. As depicted in the microscopic images, when electrospinning was performed at 15 kV/10 cm, the cellulose suspension was spattered unlike in the usual electrospinning process. As a result, fibers were not formed. However, lines of small sphere-like droplets of the solution were obtained. These droplets were not in regular size and appeared as individual droplets without being connected to each other.

In order to optimize the conditions, the voltage as well as the distance between the tip of the needle and the collector, were adjusted. After several adjustments, a voltage of 16 kV and a needle-collector distance of 5.5 cm, corresponding to an electric field strength of 3 kV/cm, gave optimum results. The morphology of the resulting materials after electrospinning were different for 15 kV/10 cm and 16 kV/5.5 cm, as illustrated in FIG. 36(A). In FIG. 36(B), it is clear that the solution was deposited on the glass slide as individual aggregates. Its morphology is similar to a non-uniform coating.

FIGS. 36A and 36B show microscopic images of the material deposited on the glass slide from 5% (w/v) MCC in DMAc/LiCl with voltage at: (FIG. 36A) 15 kV/10 cm; (FIG. 36B) 16 kV/5.5 cm.

During the electrospinning experiments of cellulose dissolved in $[C_4C_1im][Cl]$ (3% (w/w)), a Taylor cone formation was observed. Nonetheless, fibers were not spun into a continuous manner. This could be due to the slow flow rate of the cellulose solution caused by the temperature gradient between the upper and the lower points of the syringe. FIG. 37 shows microscopic images of electrospun fibers from 1% and 3% cellulose suspensions at different parameters 20 kV/23.2 cm and 25 kV/16 cm.

Figure 37A:
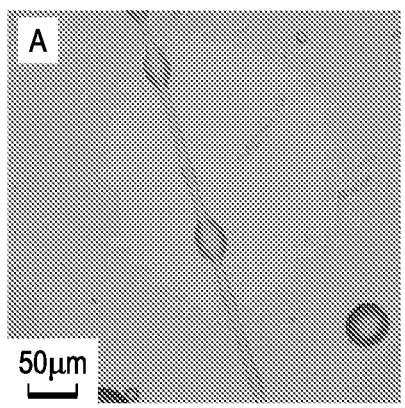
FIGS. 37A and 37B show microscopic images of electrospun fibers from cellulose solutions: (A) 1% (w/w) cotton dissolved in [$C_4C_1$im][Cl] at voltage of 20 kV/23.2 cm, and (B) 3% (w/w) cotton dissolved in [$C_4C_1$im][Cl] at voltage of 25 kV/16 cm.
Figure 37B:
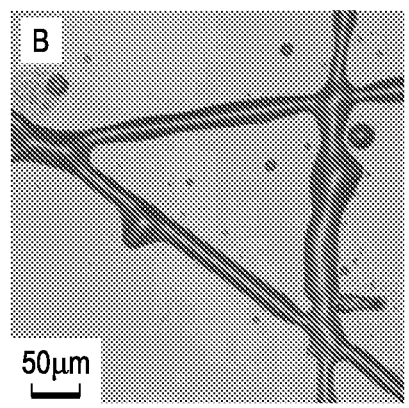

FIGS. 37A and 37B show microscopic images of electrospun fibers from cellulose solutions: (A) 1% (w/w) cotton dissolved in $[C_4C_1im][Cl]$ at voltage of 20 kV/23.2 cm, and (B) 3% (w/w) cotton dissolved in $[C_4C_1im][Cl]$ at voltage of 25 kV/16 cm.

As can be seen in microscopic image FIG. 37(A), when 1% cellulose solution was electrospun at 20 kV/23.2 cm, thinner and bead like fibers (diameter=11 pm) were formed. Those fibers were connected as a network but they appeared as individual fibers dispersed on the glass slide. In comparison, electrospinning 3% cellulose solution led to fibers having diameter in the range of 10-20 μm (FIG. 37(B)). When the parameters were altered for 1% cellulose solution (18 kV/16 cm), fibers were continuously spun to the aluminum foil and to the water bath. However, most of them were attached to the inner wall of the glass jar. This implies that the concentration of the solution, the viscosity, the voltage, and the distance affect the electrospinning of cellulose solutions. These multiple experiments with different concentrations enabled us to optimize the conditions for electrospinning cellulose solution.

The previous examples showed that the most effective cellulose solvent system was an equimolar mixture of 1-butyl-3-methylimidazolium phosphonate and 1-methtylimidazole. This solvent system was used to generate cellulose solutions for the current electrospinning process. The procedure for dissolving cellulose with this solvent system was described in the previous progress report. The solutions were electrospun at 18 kV/18 cm and the fibers were collected on a glass slide and analyzed with a microscope (FIG. 38). A continuous web of fibers was formed from the tip of the syringe that extended to the collector. Electrospinning of ethanol-treated (5% w/w) cotton fibers dissolved in 1:1 molar ratio of $[C_4C_1im][(OMe)(H)PO_2]$ and 1-methylimidazole. However, they were not deposited on the collector during the process. This could be due to the conductivity of cellulose solutions. However, when the applied voltage was turned off, fibers were deposited on the glass slide. The diameter of these fibers was approximately 1.8 μm. A non-uniform distribution of beads with different diameters were also formed.

Figure 38A:
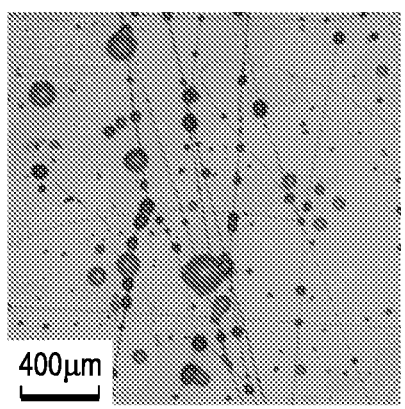
FIGS. 38A and 38B show microscopic images of electrospun fibers from cellulose solution: ethanol-treated (5% w/w) cotton fibers dissolved in 1:1 molar ratio of [$C_4C_1$im][(OMe)(H)$PO_2$] and 1-methylimidazole.
Figure 38B:
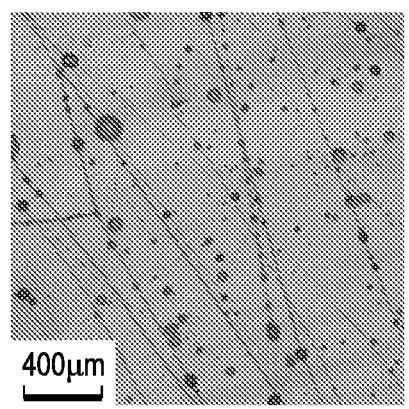

FIGS. 38A and 38B show microscopic images of electrospun fibers from cellulose solution: ethanol-treated (5% w/w) cotton fibers dissolved in 1:1 molar ratio of $[C_4C_1im][(OMe)(H)PO_2]$ and 1-methylimidazole.

Figure 39:
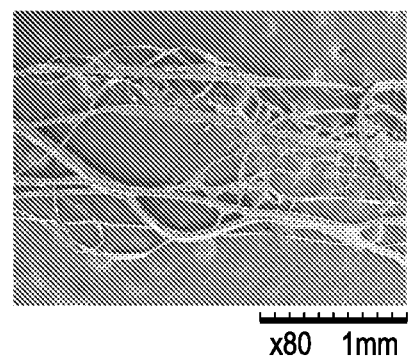
FIG. 39 is a SEM image of electrospun fibers from cellulose solution: Ethanol-treated (5% w/w) cotton fibers dissolved in 1:1 molar ratio of [$C_4C_1$im][(OMe)(H)$PO_2$] and 1-methylimidazole.

When the solution was electrospun in the water bath, a mesh of fibers was formed (FIG. 39). These fibers were collected, air dried, and characterized using SEM and FT-IR. As can be seen in the SEM image, the fibers were not separated, and they were entangled. The inventors attribute the entanglement to the presence of residual solvent, which is difficult to remove because of its low volatility. FIG. 39: SEM image of electrospun fibers from cellulose solution: Ethanol-treated (5% w/w) cotton fibers dissolved in 1:1 molar ratio of $[C_4C_1im][(OMe)(H)PO_2]$ and 1-methylimidazole.

Figure 40:
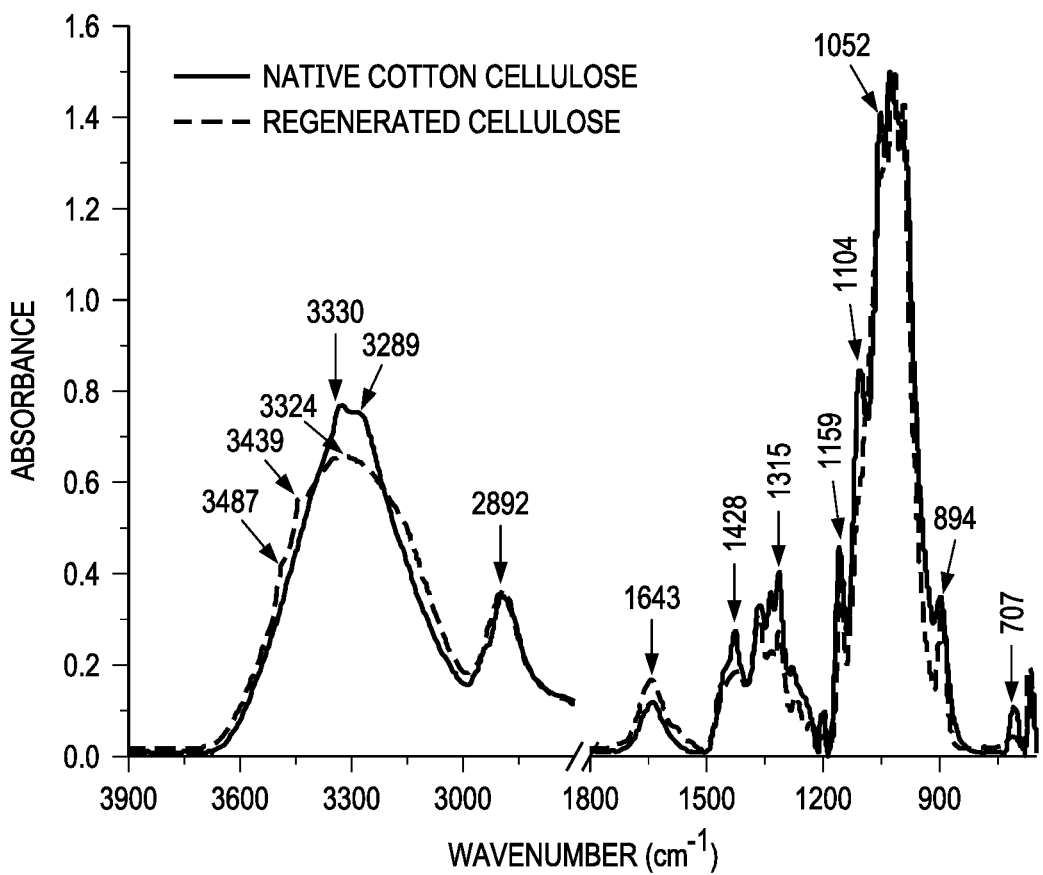
FIG. 40 is a graph of an FTIR spectra of hot-dried cotton fibers and air-dried cellulose fibers regenerated after dissolution in 1:1 molar ratio of 1-butyl-3-methylimidazolium phosphonate and 1-methylimidazole.

The FTIR spectra of regenerated cellulose fibers and hot-dried ground cotton fibers are shown in FIG. 40. The absorption bands in the FTIR spectrum of the regenerated cellulose were similar to the FTIR spectrum of the native cotton cellulose. No new absorption bands were observed indicating that no chemical reaction occurred during the dissolution and regeneration of cotton cellulose.

FIG. 40 is an FTIR spectra of hot-dried cotton fibers and air-dried cellulose fibers regenerated after dissolution in 1:1 molar ratio of 1-butyl-3-methylimidazolium phosphonate and 1-methylimidazole.

Few differences in the absorbance bands particularly at 3487, 3439, 1428, 1315 and 894 $cm^{-1}$ were observed. The absorbance bands at 3487 $cm^{-1}$ and 3439 $cm^{-1}$ are attributed to inter-molecular hydrogen bonding. The changes occurred in this region in regenerated cellulose indicate that the inter-molecular hydrogen bonding network was disrupted during the dissolution. Furthermore, the vibration 1428 $cm^{-1}$ (assigned to C—H symmetric bending at the $C_6$ position, which is referred to as the "crystalline band") is shifted to a lower wavenumber (1418 $cm^{-1}$) in the spectra of regenerated cellulose. This indicates that the regenerated cellulose has mainly an amorphous structure. The sharp peak at 894 $cm^{-1}$ corresponds to the C—O—C stretching (β-glycosidic linkage, which is also referred to as the "amorphous absorption band"). In regenerated cellulose fibers, this absorption band appears as a sharp peak at lower wavenumbers, indicating lower crystallinity of the regenerated fibers.

Figure 41A:
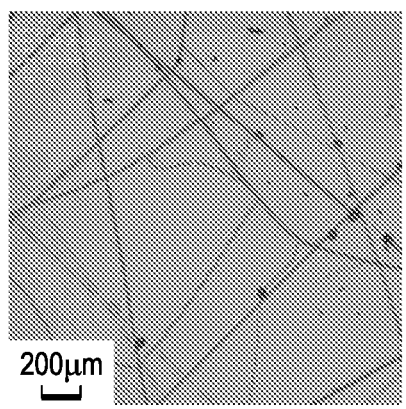
FIGS. 41A and 41B show microscopic images of the electrospun fibers from cellulose solution: ethanol-treated (5% w/w) cotton fibers dissolved in 1:1 molar ratio of [$C_4C_1$im][(OMe)(H)$PO_2$] and DMF.
Figure 41B:
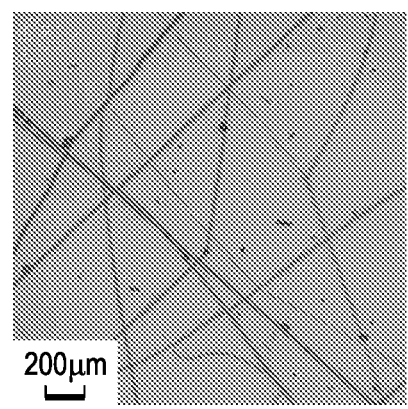

To lower the surface tension of the cellulose solution, the inventors used dimethylformamide (DMF) as a co-solvent. The protocol taught hereinabove was used with an equimolar mixture of IL and DMF to dissolve ethanol-treated 5% (w/w) cotton cellulose. Complete dissolution was achieved in 15 minutes as confirmed by PLM images. These solutions were electrospun, the product formed was collected on glass slides (ground aluminum foil), and the morphology was examined using a microscope (FIGS. 41A and 41B). FIGS. 41A and 41B show microscopic images of the electrospun fibers from cellulose solution: ethanol-treated (5% w/w) cotton fibers dissolved in 1:1 molar ratio of $[C_4C_1im][(OMe)(H)PO_2]$ and DMF.

Figure 42A:
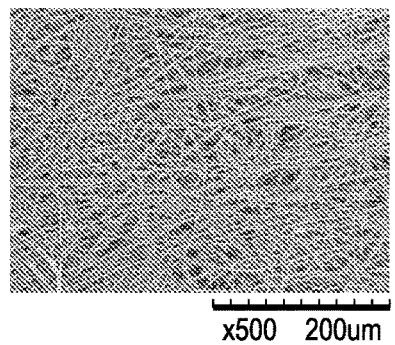
FIGS. 42A and 42B show SEM images of electrospun fibers from a cellulose solution: ethanol-treated (5% w/w) cotton fibers dissolved in 1:1 molar ratio of [$C_4C_1$im][(OMe)(H)$PO_2$] and DMF.
Figure 42B:
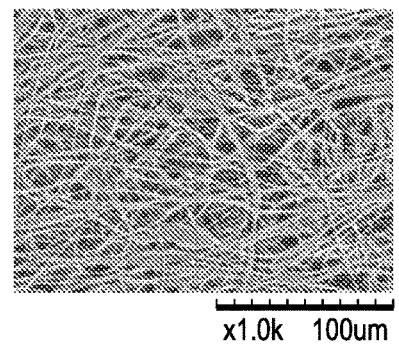

Further studies were performed and cotton cellulose was electrospun in water bath, regenerated, and air dried. FIGS. 42A and 42B show SEM images of the material. It is evident from these images that this solvent system leads to the formation of fibers that are not entangled as in previous experiments. This newly developed method can be optimized to generate nano-scale cellulose fibers, which can be useful in various biomedical applications.

FIGS. 42A and 42B show SEM image of electrospun fibers from a cellulose solution: ethanol-treated (5% w/w) cotton fibers dissolved in 1:1 molar ratio of $[C_4C_1im]$ $[(OMe)(H)PO_2]$ and DMF.

Wet spinning. A lab-scale wet spinning apparatus equipped with a syringe pump was used. Cotton cellulose was scoured and bleached, and then was dissolved in DMAc/LiCl at 1% and 3% concentrations. A syringe pump with a range of pumping rates (1 L/h to 1250 mL/h) and two syringe needles (G27 O.D. 0.45 µm and G22 0.7 µm) were used to produce regenerated cellulose fibers in DI water. The resulting fibers were immersed in 30% glycerol/DI water solution for 24 h and then were air-dried and freeze-dried. Scanning Electron Microscopy and Favimat were used to characterize the fibers.

A viscosity of the cellulose solutions for wet-spinning was between 100-400 Pa·s. Indeed, when the viscosity of the solution was >400 Pa·s, it was difficult to spin fibers using G27 needle with I.D. 0.21 mm (O.D. 0.45 mm). When the viscosity of the solution was <100 Pa-s, cellulose beads were formed. The pumping rate could be set at a value higher than 70 mL/h and the wet-spinning could continuously proceed to obtain unbroken fibers that may be winded onto a rotary drum collector.

Figure 43A:
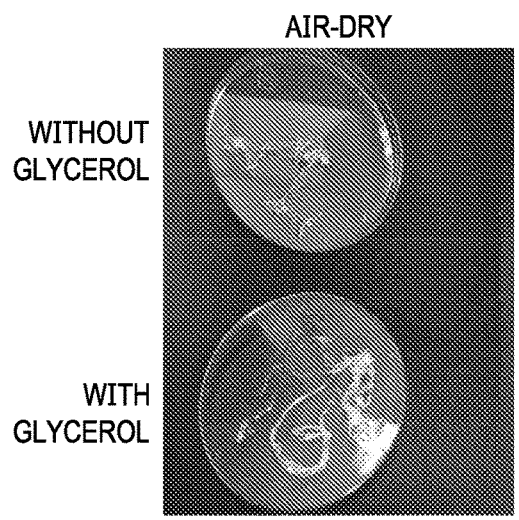
FIGS. 43A and 43B show wet-spun cellulose fibers with and without glycerol treatment air-dried and freeze-dried.
Figure 43B:
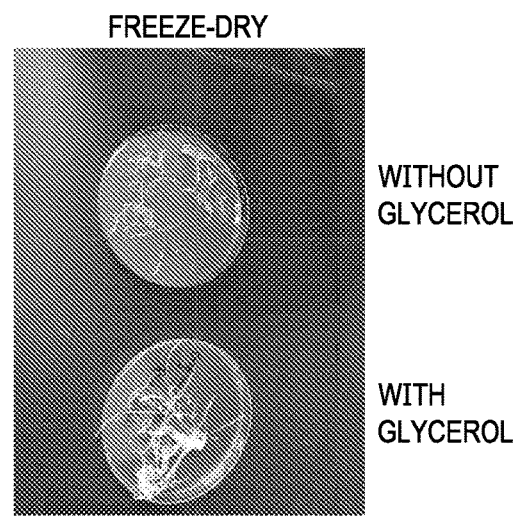
Figure 44A:
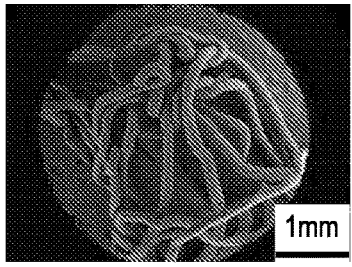
FIGS. 44A to 44L show SEM images of wet-spun fibers with and without glycerol treatment air-dried and freeze-dried.
Figure 44B:
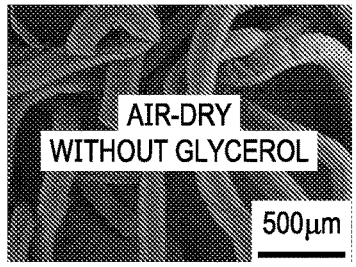
Figure 44C:
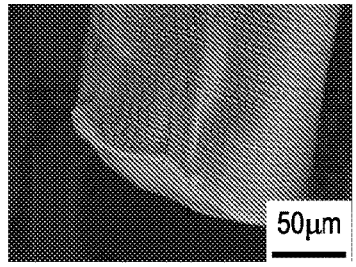
Figure 44D:
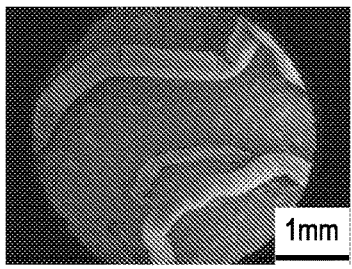
Figure 44E:
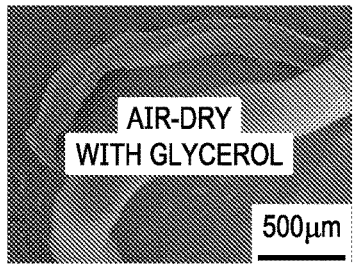
Figure 44F:
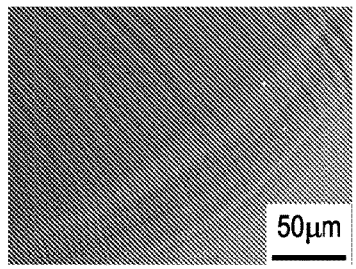
Figure 44G:
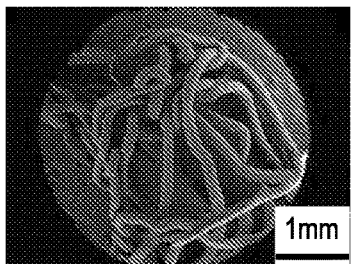
Figure 44H:
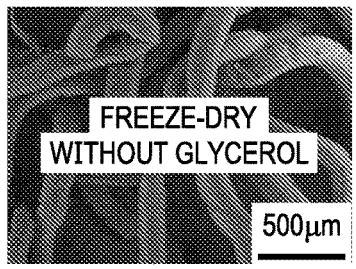
Figure 44I:
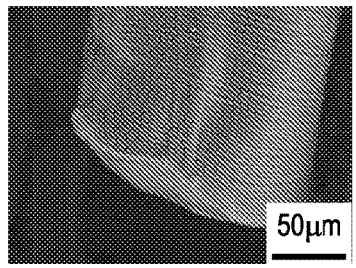
Figure 44J:
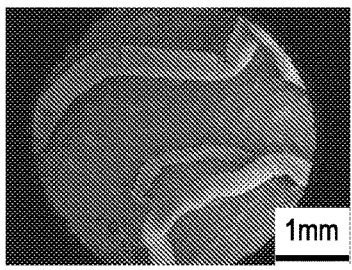
Figure 44K:
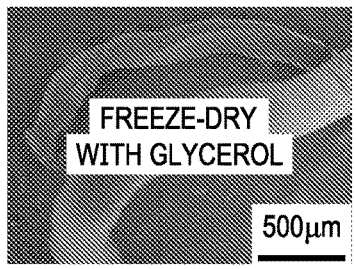
Figure 44L:
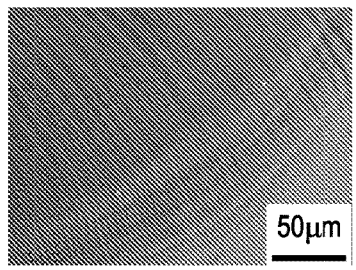

FIGS. 43A and 43B shows pictures of air-dried and freeze-dried fibers with and without glycerol treatment. The fibers obtained with freeze-drying without glycerol treatment exhibit better shape than other fiber products. SEM images in FIG. 44 show that the smallest fiber diameter was around 100 µm. Although the glycerol treatment could significantly reduce the surface roughness of the fibers, it increased the average fiber size as compared to fibers without glycerol treatment.

Figure 45A:
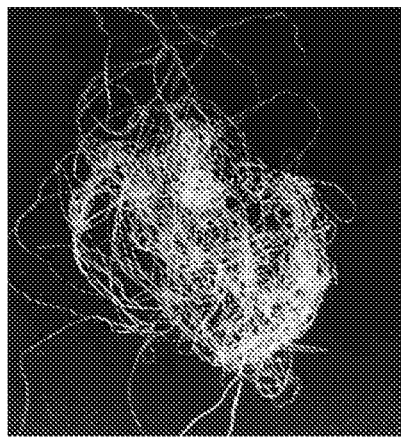
FIGS. 45A and 45B show fiber spun from a solution of cotton cellulose (2%). Left: air-dried, right: freeze-dried.
Figure 45B:
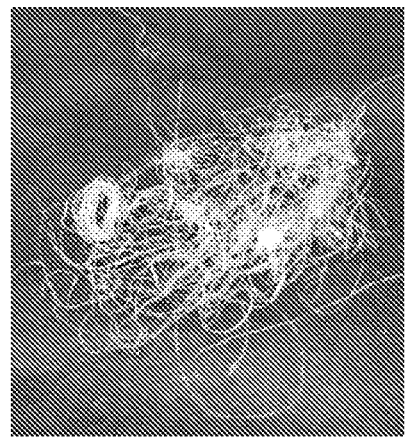
Figure 46A:
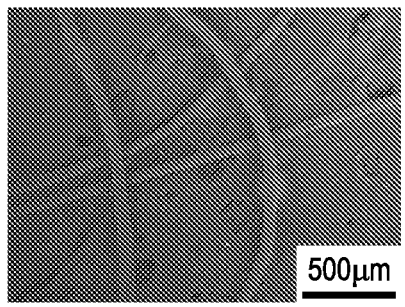
FIGS. 46A and 46B show scanning electron microscopy of fiber spun from a solution of cotton cellulose (2%). Air-dried.
Figure 46B:
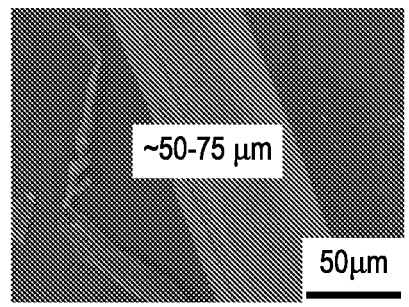
Figure 47A:
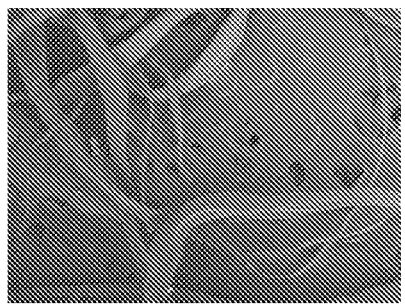
FIGS. 47A and 47B show scanning electron microscopy of fiber spun from a solution of cotton cellulose (2%). Freeze-dried.
Figure 47B:
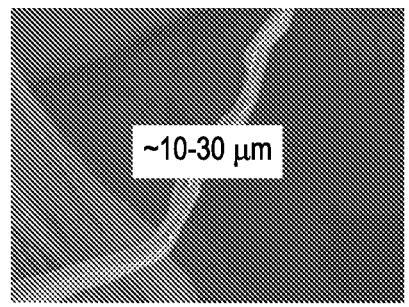

FIGS. 43A and 43B show wet-spun cellulose fibers with and without glycerol treatment air-dried and freeze-dried. FIGS. 44A to 44L. SEM images of wet-spun fibers with and without glycerol treatment air-dried and freeze-dried. FIGS. 45A and 45B: Fiber spun from a solution of cotton cellulose (2%). Left: air-dried, right: freeze-dried. FIGS. 46A and 46B: Scanning electron microscopy of fiber spun from a solution of cotton cellulose (2%). Air-dried. FIGS. 47A and 47B: Scanning electron microscopy of fiber spun from a solution of cotton cellulose (2%). Freeze-dried.

Next, 2% cotton fiber mixed with polyvinylpyrrolidone (PVP). 2% low micronaire (2.4) cotton fibers were dissolved in DMAc/LiCl until transparent solution was obtained. Once the cellulose was well dissolved, high molecular weight PVP (380,000) was added to the cellulose solution (1:1, w:w). The mixture was wet spun.

Figure 48A:
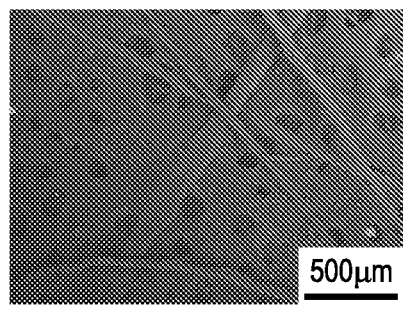
FIGS. 48A and 48B show scanning electron microscopy of fiber spun from a solution of cotton cellulose (2%) and polyvinylpyrrolidone. Air-dried.
Figure 48B:
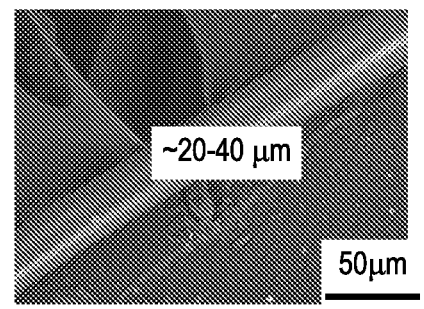
Figure 49A:
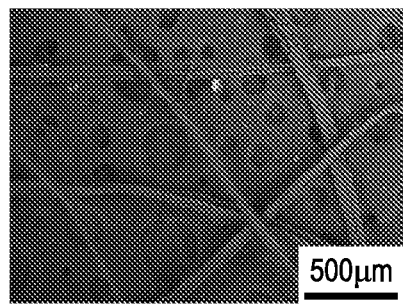
FIGS. 49A and 49B show scanning electron microscopy of fiber spun from a solution of cotton cellulose (2%) and polyvinylpyrrolidone. Freeze-dried.
Figure 49B:
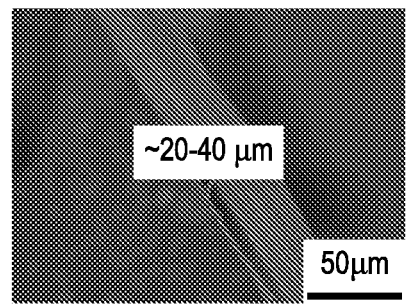

FIGS. 48A and 48B show scanning electron microscopy of fiber spun from a solution of cotton cellulose (2%) and polyvinylpyrrolidone. Air-dried. FIGS. 49A and 49B show scanning electron microscopy of fiber spun from a solution of cotton cellulose (2%) and polyvinylpyrrolidone. Freeze-dried.

These studies demonstrate that cellulose solutions generated from equimolar mixture of 1-butyl-3-methylimidazolium phosphonate and 1-methylimidazole was the most effective in the electrospinning process. The conductivity of the solution can be modified to enable better deposition of fibers on the collector. One of the drawbacks of commercially available solvent systems the inventors used in a comparative study was the viscosity of these solutions, which caused difficulties when the sample was being ejected from the syringe. Heating the syringe causes the process to be more effective. For cellulose solutions used for electrospinning experiments, the inventors determined a useful range of voltage to be between 15 to 24 kV and the distance between the nozzle and the collector to be between 7 and 18 cm. The flow can be adjusted in order to achieve continuous fiber formation. The skilled artisan will recognized that, using the present invention, it is possible to further optimize: the viscosity of the cellulose solution, the best voltage and the optimum distance to obtain submicron-scale cellulose fibers after electrospinning. These examples show that using DMF as a co-solvent with the IL resulted in better fiber formation using the parameters taught herein.

To scale up the wet spinning process, it is possible to use a two-step coagulation bath spinning plus a 20-liter feeding tank. The first step is cellulose regeneration while the second step is the removal of the solvent. Using the information taught herein, it is possible to vary processing parameters to scale up production. First, the viscosity of the cellulose solution can be significantly increased to higher more than 400 Pa·s. Therefore, the pumping speed would be able to be set at a value higher than 200 mL/h to offer a high pressure for pumping highly viscosity cellulose solution. Furthermore, a filtration step may be considered to add between the feeding tank and the spinneret to remove undissolved cellulose. The device and methods taught herein allow for more cellulose in the cellulose solution, and thus, creating fibers with higher strength for advanced applications.

Figure 50:
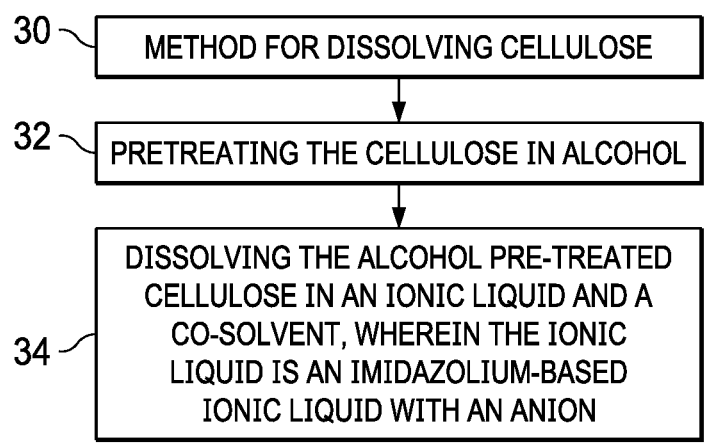
FIG. 50 is a flowchart that shows a method for dissolving cellulose.

FIG. 50 is a flowchart that shows a method for dissolving cellulose 30 by pretreating the cellulose in alcohol 32, and dissolving the alcohol pre-treated cellulose in an ionic liquid and a co-solvent, wherein the ionic liquid is an imidazolium-based ionic liquid with an anion 34.

Figure 51:
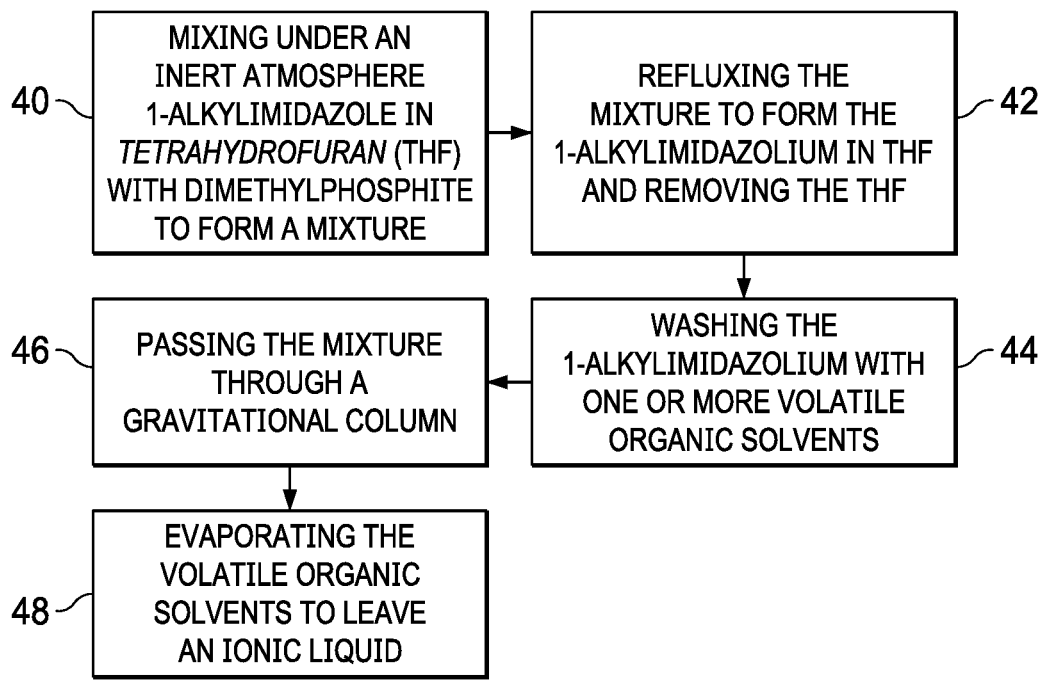
FIG. 51 is a flowchart that shows a method of making a 1-alkylimidazolium

FIG. 51 is a flowchart that shows a method of making a 1-alkylimidazolium by mixing under an inert atmosphere 1-alkylimidazole in tetrahydrofuran (THF) with dimethylphosphite to form a mixture (40); refluxing the mixture to form the 1-alkylimidazolium in THF and removing the THF (42); washing the 1-alkylimidazolium with one or more volatile organic solvents (44); passing the mixture through a gravitational column (46); and evaporating the volatile organic solvents to leave an ionic liquid (48).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least 1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Abe M, Fukaya Y, Ohno H (2010) Extraction of polysaccharides from bran with phosphonate or phosphinate-derived ionic liquids under short mixing time and low temperature Green Chemistry 12:1274-1280 doi:10.1039/c003976d Abidi N, Cabrales L, Haigler C H (2014) Changes in the cell wall and cellulose content of developing cotton fibers investigated by FTIR spectroscopy Carbohydrate Polymers 100:9-16 doi:10.1016/j.carbpol.2013.01.074

Abidi N, Hequet E, Cabrales L, Gannaway J, Wilkins T, Wells L W (2008) Evaluating cell wall structure and composition of developing cotton fibers using Fourier transform infrared spectroscopy and thermogravimetric analysis J Appl Polym Sci 107:476-486 doi:10.1002/app.27100

Dassanayake R S, Gunathilake C, Jackson T, Jaroniec M, Abidi N (2016) Preparation and adsorption properties of aerocellulose-derived activated carbon monoliths Cellulose 23:1363-1374 doi:10.1007/s10570-016-0886-1

Fukaya, Y., et al., Cellulose dissolution with polar ionic liquids under mild conditions: required factors for anions. Green Chemistry, 2008. 10(1): p. 44-46.

Gericke M, Fardim P, Heinze T (2012) Ionic Liquids—Promising but Challenging Solvents for Homogeneous Derivatization of Cellulose Molecules 17:7458-7502 doi:10.3390/molecules17067458

Gupta K M, Jiang J W (2015) Cellulose dissolution and regeneration in ionic liquids: A computational perspective Chem Eng Sci 121:180-189 doi:10.1016/j.ces.2014.07.025

Haigler C H, Betancur L, Stiff M R, Tuttle J R (2012) Cotton fiber: a powerful single-cell model for cell wall and cellulose research Front Plant Sci 3:7 doi:10.3389/fpls.2012.00104

Heinze T, Dom S, Schoebitz M, Liebert T, Koehler S, Meister F (2008) Interactions of ionic liquids with polysaccharides-2: Cellulose Macromol Symp 262:8-22 doi:10.1002/masy.200850202

Ilharco L M, Garcia A R, daSilva J L, Ferreira L F V (1997) Infrared approach to the study of adsorption on cellulose: Influence of cellulose crystallinity on the adsorption of benzophenone Langmuir 13:4126-4132 doi:10.1021/la962138u Kosan B, Michels C, Meister F (2008) Dissolution and forming of cellulose with ionic liquids Cellulose 15:59-66 doi:10.1007/s10570-007-9160-x Lan W, Liu C F, Yue F X, Sun R C, Kennedy J F (2011) Ultrasound-assisted dissolution of cellulose in ionic liquid Carbohydrate Polymers 86:672-677 doi:10.1016/j.carbpol.2011.05.013

Lau R M, Sorgedrager M J, Carrea G, van Rantwijk F, Secundo F, Sheldon R A (2004) Dissolution of *Candida antarctica* lipase B in ionic liquids: effects on structure and activity Green Chemistry 6:483-487 doi:10.1039/b405693k Li Y, Liu X M, Zhang S J, Yao Y Y, Yao X Q, Xu J L, Lu X M (2015) Dissolving process of a cellulose bunch in ionic liquids: a molecular dynamics study Phys Chem Phys 17:17894-17905 doi:10.1039/c5cp02009c Lindman B, Karlstrom G, Stigsson L (2010) On the mechanism of dissolution of cellulose J Mol Liq 156:76-81 doi:10.1016/j.molliq.2010.04.016

Lu B L, Xu A R, Wang J J (2014) Cation does matter: how cationic structure affects the dissolution of cellulose in ionic liquids Green Chemistry 16:1326-1335 doi: 10.1039/c3gc41733f Oh S Y et al. (2005a) Crystalline structure analysis of cellulose treated with sodium hydroxide and carbon dioxide by means of X-ray diffraction and FTIR spectroscopy Carbohydr Res 340:2376-2391 doi:10.1016/j.carres.2005.08.007

Oh S Y, Yoo D I, Shin Y, Seo G (2005b) FTIR analysis of cellulose treated with sodium hydroxide and carbon dioxide Carbohydr Res 340:417-428 doi:http://dx.doi.org/10.1016/j.carres.2004.11.027

Olsson C, Westman G (2013) Direct Dissolution of Cellulose: Background, Means and Applications Cellulose—Fundamental Aspects:143-178 doi:10.5772/52144

Phillips D M et al. (2004) Dissolution and regeneration of *Bombyx mori* Silk fibroin using ionic liquids J Am Chem Soc 126:14350-14351 doi:10.1021/ja046079f Pinkert A, Marsh K N, Pang S S, Staiger M P (2009) Ionic Liquids and Their Interaction with Cellulose Chem Rev 109:6712-6728 doi:10.1021/cr9001947

Rabideau B D, Agarwal A, Ismail A E (2014) The Role of the Cation in the Solvation of Cellulose by Imidazolium-Based Ionic Liquids J Phys Chem B 118:1621-1629 doi:10.1021/jp4115755

Ragauskas A J et al. (2006) The path forward for biofuels and biomaterials Science 311:484-489 doi:10.1126/science.1114736

Remsing R C, Hernandez G, Swatloski R P, Massefski W W, Rogers R D, Moyna G (2008) Solvation of carbohydrates in N,N'-dialkylimidazolium ionic liquids: A multinuclear NMR spectroscopy study J Phys Chem B 112:11071-11078 doi:10.1021/jp8042895

Remsing R C, Swatloski R P, Rogers R D, Moyna G (2006) Mechanism of cellulose dissolution in the ionic liquid 1-n-butyl-3-methylimidazolium chloride: a C-13 and Cl-35/37 NMR relaxation study on model systems Chem Commun:1271-1273 doi:10.1039/b600586c Rogers R D, Seddon K R (2003) Ionic liquids—Solvents of the future? Science 302:792-793 doi:10.1126/science.1090313

Salmen L, Bergstrom E (2009) Cellulose structural arrangement in relation to spectral changes in tensile loading FTIR Cellulose 16:975-982 doi:10.1007/s0570-009-9331-z Samir M, Alloin F, Dufresne A (2005) Review of recent research into cellulosic whiskers, their properties and their application in nanocomposite field Biomacromolecules 6:612-626 doi:10.1021/bm0493685

Schwanninger M, Rodrigues J C, Pereira H, Hinterstoisser B (2004) Effects of short-time vibratory ball milling on the shape of FT-IR spectra of wood and cellulose Vibrational Spectroscopy 36:23-40 doi:http://dx.doi.org/10.1016/j.vibspec.2004.02.003

Sun N, Rodriguez H, Rahman M, Rogers R D (2011) Where are ionic liquid strategies most suited in the pursuit of chemicals and energy from lignocellulosic biomass? Chem Commun 47:1405-1421 doi:10.1039/c0cc03990j Swatloski R P, Spear S K, Holbrey J D, Rogers R D (2002) Dissolution of cellose with ionic liquids J Am Chem Soc 124:4974-4975 doi:10.1021/ja025790m Vitz J, Erdmenger T, Haensch C, Schubert U S (2009) Extended dissolution studies of cellulose in imidazolium based ionic liquids Green Chemistry 11:417-424 doi:10.1039/b818061j Welton T (1999) Room-temperature ionic liquids. Solvents for synthesis and catalysis Chem Rev 99:2071-2083 doi:10.1021/cr980032t Xu A R, Wang J J, Wang H Y (2010) Effects of anionic structure and lithium salts addition on the dissolution of cellulose in 1-butyl-3-methylimidazolium-based ionic liquid solvent systems Green Chemistry 12:268-275 doi:10.1039/b916882f Xu H, Pan W X, Wang R X, Zhang D J, Liu C B (2012) Understanding the mechanism of cellulose dissolution in 1-butyl-3-methylimidazolium chloride ionic liquid via quantum chemistry calculations and molecular dynamics simulations J Comput-Aided Mol Des 26:329-337 doi:10.1007/s10822-012-9559-9

Yao Y Y, Li Y, Liu X M, Zhang X C, Wang J J, Yao X Q, Zhang S J (2015) Mechanistic study on the cellulose dissolution in ionic liquids by density functional theory Chin J Chem Eng 23:1894-1906 doi:10.1016/j.cjche.2015.07.018

Youngs T G A, Hardacre C, Holbrey J D (2007) Glucose solvation by the ionic liquid 1,3-dimethylimidazolium chloride: A simulation study J Phys Chem B 111:13765-13774 doi:10.1021/Jp076728k Youngs T G A et al. (2011) Neutron diffraction, NMR and molecular dynamics study of glucose dissolved in the ionic liquid 1-ethyl-3-methylimidazolium acetate Chem Sci 2:1594-1605 doi:10.1039/c1sc00241d Zhang H, Wu J, Zhang J, He J S (2005) 1-Allyl-3-methyl-imidazolium chloride room temperature ionic liquid: A new and powerful nonderivatizing solvent for cellulose Macromolecules 38:8272-8277 doi:10.1021/ma0505676

Zhang S J, Sun N, He X Z, Lu X M, Zhang X P (2006) Physical properties of ionic liquids: Database and evaluation J Phys Chem Ref Data 35:1475-1517 doi:10.1063/1.2204959

What is claimed is:

1. A method for dissolving cellulose comprising:
pretreating the cellulose with alcohol prior to the dissolving step;
drying the cellulose to remove alcohol for between 2 h to 8 h at temperatures between 15 and 105° C.; and
dissolving the cellulose in an ionic liquid and a co-solvent, wherein the ionic liquid is selected from an imidazolium-based ionic liquid with acetate anion or halide anion, wherein the imidazolium-based ionic liquid is selected from at least one of: 1-methylimidazolium, 1-ethylimidazolium, 1-propylimidazolium, 1-butylimidazolium, 1-(cyclohexylmethyl)-3-methylimidazolium, 1,3-dibenzylimidazolium, 1-(2-napthylmethyl)-3-methylimidazolium, 1,3-dibenzylimidazolium, 1-hepyl-3-methylimidazolium halide (X) ([$C_7C_1$im]X), 1-(cyclohexylmethyl)-3-methylimidazolium halide ([Cyhm$C_1$im]X), 1,3-dibenzylimidazolium halide ([(Bnz)$_2$im]X), and 1-(2-napthylmethyl)-3-methylimidazolium halide ([Napm$C_1$im]X), 1-methylimidazolium halide, 1-ethylimidazolium halide, 1-propylimidazolium halide, or 1-butylimidazolium halide, wherein the cellulose is untreated cotton cellulose.

2. The method of claim 1, wherein the co-solvent is selected from at least one of 1-methylimidazole, 1ethylimidazole, or 1-butylimidazole.

3. The method of claim 1, wherein the alcohol is ethanol, 1-propanol, iso-propanol, or tert-butanol.

4. The method of claim 1, further comprising pretreating is for 1, 2, 3, 4, 5, 6, 7, or 8 hours at a temperature between room temperature to 30° C.

5. The method of claim 1, wherein the co-solvent is selected from at least one of DMSO, DMF, DMI, DMAc, or N-methylimidazole (MIM).

6. The method of claim 1, wherein the imidazolium-based ionic liquid with acetate as the anion is selected from at least one of 1-(cyclohexylmethyl)-3-methylimidazolium acetate ([CyhmC$_1$im][OAc]), 1,3-dibenzylimidazolium acetate ([(Bnz)$_2$im][OAc]), and 1-(2-napthylmethyl)-3-methylimidazolium acetate ([NapmC$_1$im][OAc]).

7. The method of claim 1, further comprising the step of dissolving is at 90-100° C., or the step of dissolving is with microwave energy.

8. The method of claim 1, wherein the imidazolium-based ionic liquid with acetate as the anion is pre-heated to 70, 75, 80, 85, 90, 95, 96, 97, 97, 99, or 100° C.

9. The method of claim 1, wherein prior to dissolving the cellulose is at least one of raw, scoured, bleached, air-dried, heat-dried, or ground.

10. The method of claim 1, wherein the imidazolium-based ionic liquid with acetate as the anion is pre-heated until fluid.

11. A method for dissolving cellulose comprising:
pretreating the cellulose with alcohol prior to the dissolving step;
drying the cellulose to remove alcohol for between 2 h to 8 h at temperatures between 15 and 105° C.; and
dissolving the cellulose in an ionic liquid and a co-solvent, wherein the ionic liquid is selected from an imidazolium-based ionic liquid with acetate anion or halide anion, wherein the imidazolium-based ionic liquid is selected from at least one of: 1-(cyclohexylmethyl)-3-methylimidazolium acetate ([CyhmC$_1$im][OAc]), 1,3-dibenzylimidazolium acetate ([(Bnz)$_2$im][OAc]), and 1-(2-napthylmethyl)-3-methylimidazolium acetate ([NapmC$_1$im][OAc]).

12. The method of claim 11, wherein the alcohol is ethanol, 1-propoapanol, iso-propanol, or tert-utanol.

13. The method of claim 11, further comprising pretreating is for 1, 2, 3, 4, 5, 6, 7, or 8 hours at a temperature between room temperature to 30° C.

14. The method of claim 11, wherein the co-solvent is selected from at least one of DMSO, DMF, DMI, DMAc, or N-methylimidazole (MIM).

15. The method of claim 11, wherein the cellulose is untreated cotton cellulose.

16. The method of claim 11, further comprising the step of dissolving is at 90-100° C., or the step of dissolving is with microwave energy.

17. The method of claim 11, wherein the imidazolium-based ionic liquid with acetate as the anion is pre-heated to 70, 75, 80, 85, 90, 95, 96, 97, 97, 99, or 100° C.

18. The method of claim 11, wherein prior to dissolving the cellulose is at least one of raw, scoured, bleached, air-dried, heat-dried, or ground.

19. The method of claim 11, wherein the imidazolium-based ionic liquid with acetate as the anion is pre-heated until fluid.

* * * * *